United States Patent
Li et al.

(10) Patent No.: US 11,865,350 B2
(45) Date of Patent: Jan. 9, 2024

(54) SYSTEMS AND METHODS OF MONITORING WEAR COMPLIANCE OF A PATIENT WEARING AN AMBULATORY MEDICAL DEVICE

(71) Applicant: ZOLL Medical Corporation, Chelmsford, MA (US)

(72) Inventors: Pai Li, Pittsburgh, PA (US); Steven J. Szymkiewicz, Bethel Park, PA (US); Shane S. Volpe, Saltsburg, PA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 123 days.

(21) Appl. No.: 16/951,246

(22) Filed: Nov. 18, 2020

(65) Prior Publication Data

US 2022/0152406 A1 May 19, 2022

(51) Int. Cl.
| | |
|---|---|
| *A61N 1/00* | (2006.01) |
| *A61N 1/39* | (2006.01) |
| *A61B 5/352* | (2021.01) |
| *A61B 5/366* | (2021.01) |
| *A61B 5/00* | (2006.01) |
| *A61B 5/11* | (2006.01) |

(52) U.S. Cl.
CPC .......... *A61N 1/3904* (2017.08); *A61B 5/0006* (2013.01); *A61B 5/11* (2013.01); *A61B 5/352* (2021.01); *A61B 5/366* (2021.01); *A61B 5/4833* (2013.01); *A61B 5/7435* (2013.01); *A61N 1/3925* (2013.01); *A61N 1/3993* (2013.01)

(58) Field of Classification Search
CPC .............................. A61N 1/3904; A61B 5/352

USPC ......................................................... 607/142
See application file for complete search history.

(56) References Cited

U.S. PATENT DOCUMENTS

| | | | |
|---|---|---|---|
| 2017/0056650 A1 | 3/2017 | Cohen et al. | |
| 2017/0296056 A1* | 10/2017 | Hresko | A61B 5/0015 |
| 2018/0184933 A1* | 7/2018 | Sullivan | A61N 1/3904 |
| 2019/0298987 A1 | 10/2019 | Freeman et al. | |

(Continued)

OTHER PUBLICATIONS

International Search Report and Written Opinion for International Application No. PCT/US2021/059604 dated Mar. 3, 2022, 13 pages.

*Primary Examiner* — Nicole F Lavert
(74) *Attorney, Agent, or Firm* — Finch & Maloney PLLC

(57) ABSTRACT

Devices, systems, and methods for providing patient wear compliance information are provided. For example, a medical device includes a plurality of electrodes configured to be continuously coupled externally to a patient and to monitor electrical activity on the skin of the patient. The system also includes at least one motion sensor configured to generate a motion signal based upon movement of the patient. The system further includes a processor configured to receive an electrical signal based on the monitored electrical activity, record a wear onset event based on the electrical signal and the motion signal, record a wear offset event based on one or more of the electrical signal and the motion signal indicating that the patient is not wearing the medical device, and output a graphical representation including information regarding the patient's wear compliance based on the recorded wear onset event and the recorded wear offset event.

20 Claims, 25 Drawing Sheets

(56) References Cited

U.S. PATENT DOCUMENTS

2020/0030616 A1\* 1/2020 Gustavson ......... A61N 1/37211
2020/0221952 A1 7/2020 Kaib et al.

\* cited by examiner

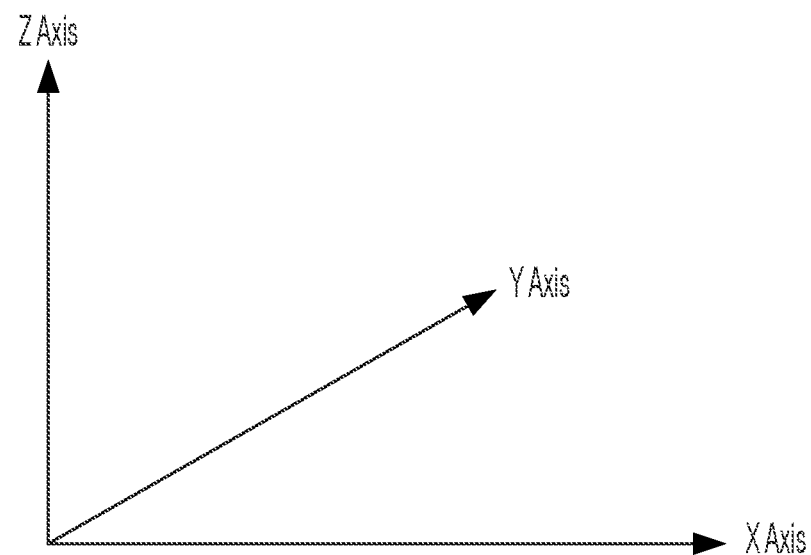
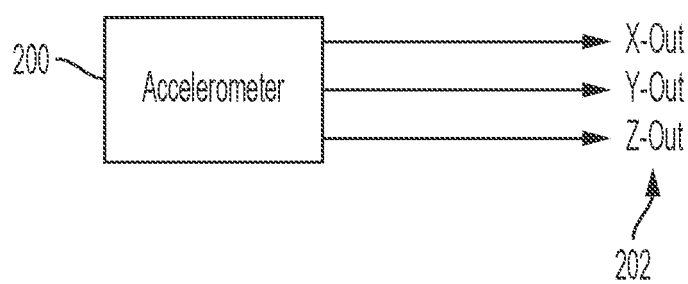
FIG. 2

900

Wear Compliance Settings for John Doe
(Patient ID XX-XXX-XXXX)
(Device ID ZXX-XXXX)

902 → Minimum Wear Compliance Information

Total Wear: [23 hrs/day]
904 → Number of Removal Periods: [2]   Max. Removal Time Per Period: [30 minutes] ← 903

Target Wear Compliance Information

Total Wear: [23.5 hrs/day]
906 → Number of Removal Periods: [1]   Max. Removal Time Per Period: [30 minutes] ← 905

Onset/Offset Event Criteria

908 → ● Use Default Criteria    ○ Use Custom Criteria ← 907

Alert Criteria ← 909

● Alert Each Day Min. Compliance Info. is Not Met
○ Alert After [3] Cons. Days Min. Compliance Info. is Not Met
○ Alert Each Day Target Compliance Info. is Not Met
● Alert After [3] Cons. Days Target Compliance Info. is Not Met
● Alert After [3] Cons. Days Target Compliance Info. is Met 910 → ( Submit )   ( Clear )   ( Cancel )

FIG. 9

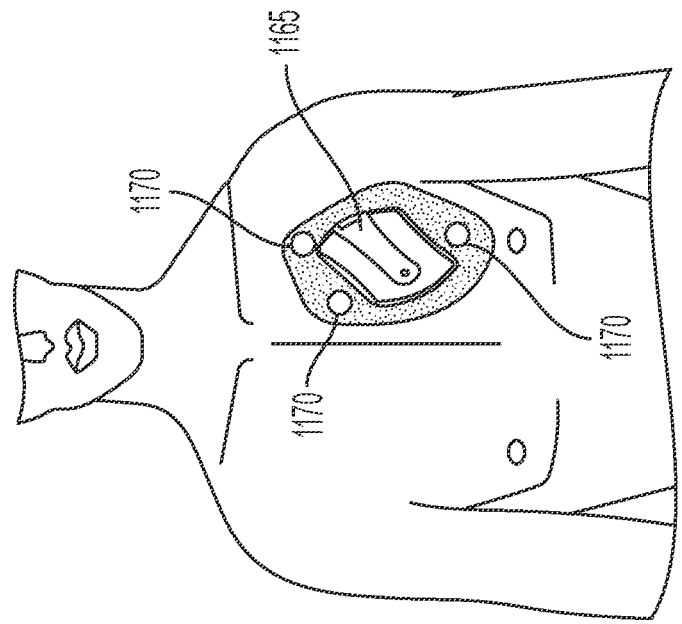
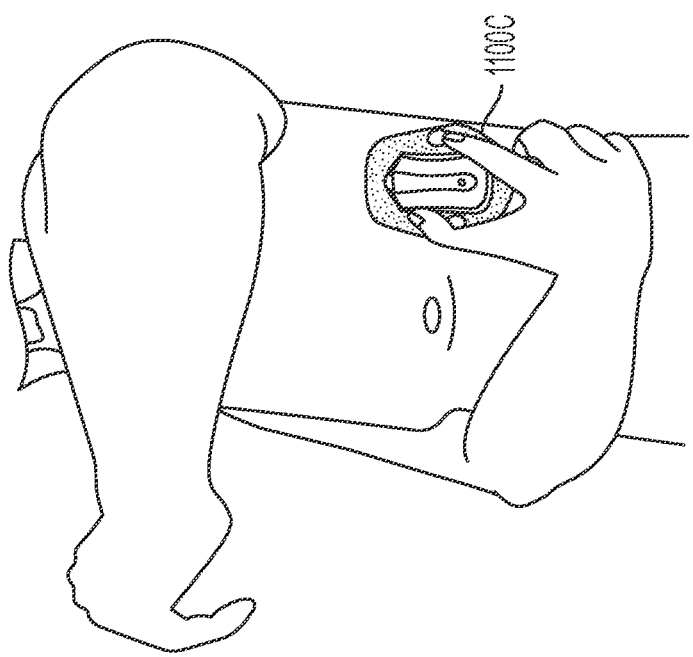
FIG. 11C

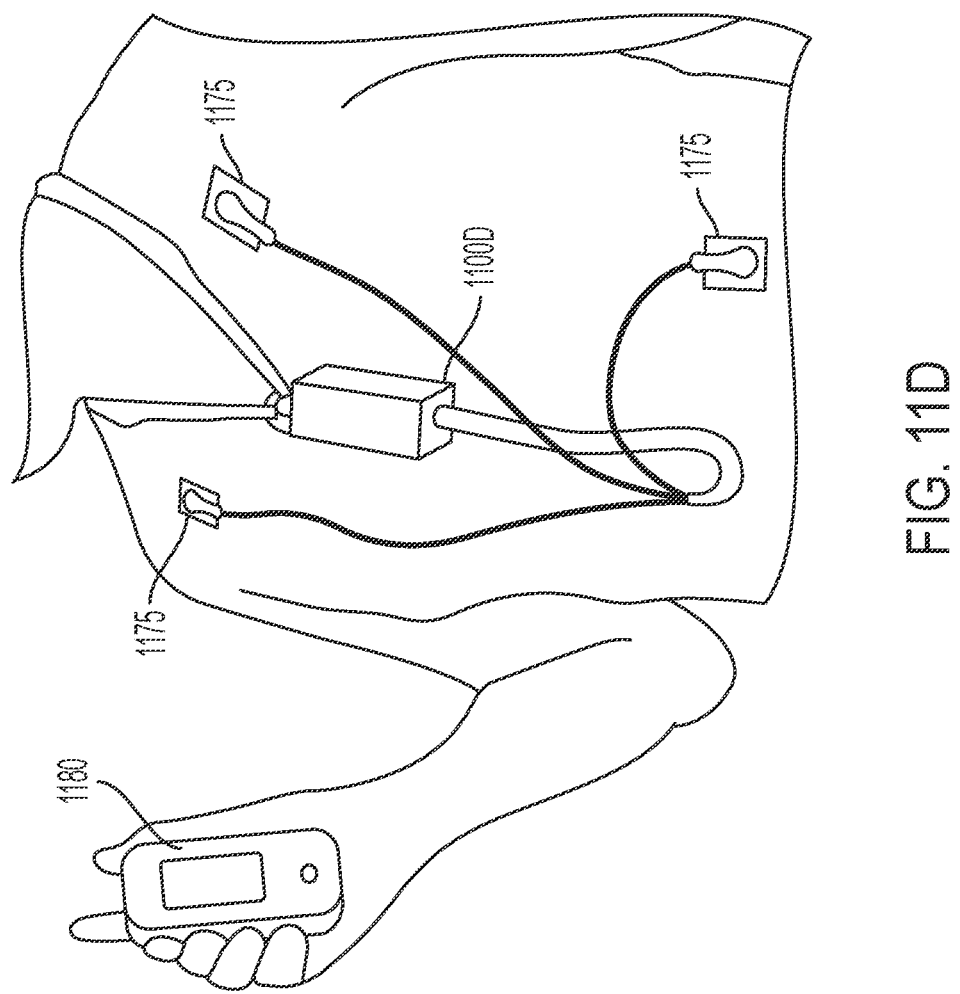

SYSTEMS AND METHODS OF MONITORING WEAR COMPLIANCE OF A PATIENT WEARING AN AMBULATORY MEDICAL DEVICE

BACKGROUND

The present disclosure is directed to monitoring a patient that is prescribed a wearable medical device for wear compliance.

Heart failure, if left untreated, can lead to certain life-threatening arrhythmias. Both atrial and ventricular arrhythmias are common in patients with heart failure. One of the deadliest cardiac arrhythmias is ventricular fibrillation, which occurs when normal, regular electrical impulses are replaced by irregular and rapid impulses, causing the heart muscle to stop normal contractions. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity), result in the heart providing insufficient levels of blood flow to the brain and other vital organs for the support of life. It is generally useful to monitor heart failure patients to assess heart failure symptoms early and provide interventional therapies as soon as possible.

Patients who are at risk, have been hospitalized for, or otherwise are suffering from, adverse heart conditions can be prescribed a wearable cardiac monitoring and/or treatment device. In addition to the wearable device, the patient can also be given a battery charger and a set of rechargeable batteries. As the wearable device is generally prescribed for continuous or near-continuous use (e.g., only to be removed when bathing), the patient wears the device during all daily activities such as walking, sitting, climbing stairs, resting or sleeping, and other similar daily activities. Maintaining continuous use of the device as prescribed cane promote better confidence in the data collected from monitoring patient progress as well as ensure better protection to the patient including providing treatment if needed.

SUMMARY

In at least one example, a wearable defibrillator for providing patient wear compliance information is provided. The wearable defibrillator includes a plurality of electrodes configured to be continuously coupled externally to a patient for an extended period of time, the plurality of electrodes configured to monitor electrical activity on a skin of the patient and provide a therapeutic shock to the patient in response to detection of a cardiac arrhythmia based on the monitored electrical activity; at least one motion sensor and associated circuitry configured to generate at least one motion signal based upon movement of the patient; and at least one processor operably coupled to the plurality of electrodes and the at least one motion sensor and associated circuitry. The at least one processor configured to receive at least one electrical signal based on the monitored electrical activity on the skin of the patient from the plurality of electrodes, record a wear onset event based on the at least one electrical signal and the at least one motion signal indicating that the patient is wearing the wearable defibrillator, record a wear offset event based on one or more of the at least one electrical signal and the at least one motion signal indicating that the patient is not wearing the wearable defibrillator, and output a graphical representation including information regarding the patient's wear compliance based on the recorded wear onset event and the recorded wear offset event.

Implementations of the wearable defibrillator can include one or more of the following features.

In examples, the wearable defibrillator can further include a display operably coupled to the at least one processor, and wherein the at least one processor is configured to provide, via the display, the graphical representation of the patient's wear compliance based on output information regarding the patient's wear compliance.

In examples, the wearable defibrillator can further include a network interface operably coupled to the at least one processor, and wherein the at least one processor is configured to transmit the information regarding the patient's wear compliance to a remote server.

In examples of the wearable defibrillator, the at least one processor can be further configured to detect an electrocardiogram (ECG) signal based on the at least one electrical signal and control the wearable defibrillator to provide the therapeutic shock to the patient in response to the detection of the cardiac arrhythmia based on the detected ECG signal.

In examples of the wearable defibrillator, to record the wear onset event includes to detect one or more ECG signals based on the at least one electrical signal, determine whether the one or more ECG signals satisfy one or more validity criteria, and, if the one or more ECG signals satisfy at least one criterion of the one or more validity criteria, record the wear onset event. In some examples, the one or more validity criteria include at least one ECG parameter derived from the one or more ECG signals satisfying a validity threshold. In some examples, the at least one ECG parameter includes R-peak amplitude and satisfying the validity threshold including identifying at least five consecutive R-peak amplitudes that each exceed an amplitude threshold. In some examples, the at least one ECG parameter includes QRS complex width and satisfying the validity threshold including measuring at least five consecutive QRS complex widths that are each between 0.05 seconds and 0.15 seconds. In some examples, the at least one processor can be further configured to determine the patient's wear compliance based on a first ECG signal of the one or more ECG signals satisfying the validity threshold.

In examples of the wearable defibrillator, to record the wear onset event can include to detect a skin-sensor interface impedance level based on the at least one electrical signal at one or more of the plurality of electrodes, determine whether the impedance level is within an acceptable impedance range, and if the impedance level is within the acceptable impedance range, record the wear onset event, and wherein to record the wear offset event can include to determine whether the impedance level is no longer within the acceptable impedance range and record the wear offset event based on determining that the impedance level is no longer within the acceptable impedance range. In some examples, the acceptable impedance range includes at least one of a range of 20 ohms to 250 ohms, a range of 250 ohms to 1 kiloohm, and a range of 1 kiloohm to 20 kiloohms.

In examples of the wearable defibrillator, to record the wear onset event can include to determine whether the motion signal indicates movement of the patient and the wearable defibrillator and, if the motion signal indicates movement of the patient and the wearable defibrillator, record the wear onset event.

In some examples, the at least one processor can be further configured to detect one or more ECG signals based on the at least one electrical signal if the motion signal indicates no movement of the patient and the wearable defibrillator and record the wear onset event based upon analysis of the one or more ECG signals. In some examples, the at least one processor can be further configured to detect one or more noise components in the at least one electrical signal and confirm no movement of the patient based upon analysis of the one or more noise components in at least one electrical signal.

In examples of the wearable defibrillator, to record the wear onset event can include to receive input from the patient specifying that the patient is wearing the wearable defibrillator and record the wear onset event based upon the input from the patient. In some examples, to record the wear onset event based upon the input from the patient includes to confirm the patient is wearing the wearable defibrillator based on the at least one electrical signal and the at least one motion signal and record the wear onset event.

In examples of the wearable defibrillator, to record the wear offset event can include to detect a change in the at least one electrical signal indicating an invalid ECG signal and record the wear offset event based upon the invalid ECG signal.

In examples of the wearable defibrillator, to record the wear offset event can include to detect a change in a skin-sensor interface impedance level at one or more of the plurality of electrodes, determine whether the impedance level exceeds an impedance threshold, and, if the impedance level exceeds the impedance threshold, record the wear offset event. In some examples, the impedance threshold can include one or more of 10 kiloohms, 100 kiloohms, 1 megaohm, 2 megaohms, 5 megaohms, and 10 megaohms.

In examples of the wearable defibrillator, to record the wear offset event can include to determine that one or more of the plurality of electrodes and the at least one motion sensor and associated circuitry have been disconnected from the wearable defibrillator and record the wear offset event upon determining that one or more of the plurality of electrodes and the at least one motion sensor and associated circuitry have been disconnected.

In examples of the wearable defibrillator, to record the wear offset event can include to detect that the patient has taken off the wearable defibrillator based upon analysis of the at least one motion signal, confirm that the at least one electrical signal indicates that the patient has taken off the wearable defibrillator, and record the offset event based upon confirmation that the patient has taken off the wearable defibrillator.

In examples of the wearable defibrillator, to record the wear offset event can include to receive input from the patient specifying that the patient is taking off the wearable defibrillator and record the wear offset event based upon the input from the patient. In some examples, to record the wear offset event based upon the input from the patient includes to confirm the patient has removed the wearable defibrillator based on the at least one electrical signal and the at least one motion signal and record the wear offset event.

In examples of the wearable defibrillator, the at least one processor can be further configured to determine a current time of day and record at least one of the wear onset event and the wear offset event based on one or more of the at least one motion signal, the at least one electrical signal, and the current time of day. In some examples, to determine the current time of day includes to determine whether the patient has historically been in an active state or an inactive state based upon the current time of day. In some examples, the at least one processor can be further configured to record at least one of the wear onset event and the wear offset event based upon the at least one electrical signal if the patient has historically been in an inactive state at the current time of day. In some examples, the at least one processor can be further configured to record at least one of the wear onset event and the wear offset event based upon the at least one electrical signal and the at least one motion signal if the patient has historically been in an active state at the current time of day. In some examples, the at least one processor can be further configured to determine whether the patient has historically been in an active state or an inactive state based upon the current time of day and historical patient activity information recorded by the wearable defibrillator.

In examples of the wearable defibrillator, the graphical representation can include an indication of patient wear compliance relative to patient wear non-compliance.

In examples of the wearable defibrillator, the graphical representation can include an indication of recorded changes in wear compliance for the patient.

In examples of the wearable defibrillator, the graphical representation can include a timeline illustrating recorded wear onset events and wear offset events. In some examples, the timeline further illustrates a total time the wearable defibrillator was worn by the patient and a total time the wearable defibrillator was not worn by the patient over a user-selectable period of time.

In examples of the wearable defibrillator, the graphical representation can include one or more user-selectable interface controls configured to provide access to recorded ECG information for one or more of a wear onset event, a wear offset event, and a period of time when the patient was wearing the wearable defibrillator.

In examples of the wearable defibrillator, the at least one processor can be further configured to output a notification of the patient's wear compliance. In some examples, to output the notification of the patient's wear compliance includes to compare the patient's wear compliance to one or more notification criteria and, if the patient's wear compliance satisfies at least one criterion of the one or more notification criteria, output the notification. In some examples, the one or more notification criteria can include the patient failing to wear the wearable defibrillator for a certain percentage of a period of time. In some examples, the one or more notification criteria can include a recorded change in the patient's wear compliance that exceeds a compliance change threshold. In some examples, the at least one processor can be further configured to output the notification of the patient's wear compliance to at least one of the patient, a caregiver associated with the patient, and a prescriber of the wearable defibrillator.

In another example, a method of providing wear compliance information as recorded by a wearable defibrillator worn by a patient is provided. The method includes receiving, by at least one processor, at least one electrical signal determined based on monitored electrical activity on a skin of the patient from a plurality of electrodes operably coupled to the at least on processor; receiving, by the at least one processor, at least one motion signal based upon movement of the patient and generated by at least one motion sensor and associated circuitry operably coupled to the at least one processor; recording, by the at least one processor, a wear onset event based on one or more of the at least one electrical signal and the at least one motion signal indicating that the patient is wearing the wearable defibrillator; recording, by the at least one processor, a wear offset event based on one or more of the at least one electrical signal and the at least one motion signal indicating that the patient is not wearing the wearable defibrillator; providing, by the at least one processor, a graphical representation of wear compliance of the patient based on the recorded wear onset event and the recorded wear offset event; receiving, by the at least one processor, one or more notification criteria from one or more of a caregiver of the patient and a prescriber of the wearable defibrillator; comparing, by the at least one processor, the patient's wear compliance and the one or more notification criteria; and outputting, by the at least one processor, a notification to one or more of the patient, the caregiver of the patient, and the prescriber of the wearable defibrillator if the patient's wear compliance satisfies at least one criterion of the one or more notification criteria.

Implementations of the method of providing wear compliance information as recorded by a wearable defibrillator worn by a patient can include one or more of the following features.

In some examples of the method, the method can further include outputting, by the at least one processor on a display operably coupled to the at least one processor, a graphical representation of the patient's wear compliance based on output information regarding the patient's wear compliance.

In some examples of the method, the method can further include transmitting, by the at least one processor, the information regarding the patient's wear compliance to a remote server operably coupled to the at least one processor via a network interface.

In some examples of the method, the method can further include detecting, by the at least one processor, an ECG signal based on the at least one electrical signal and controlling, by the at least one processor, the wearable defibrillator to provide a therapeutic shock to the patient in response to detection of a cardiac arrhythmia based on the detected ECG signal.

In the method, recording the wear onset event can include detecting, by the at least one processor, one or more ECG signals based on the at least one electrical signal; determining, by the at least one processor, whether the one or more ECG signals satisfy one or more validity criteria; and if the one or more ECG signals satisfy at least one criterion of the one or more validity criteria, recording, by the at least one processor, the wear onset event; and wherein recording the wear offset event includes determining, by the at least one processor, whether the impedance level is no longer within the acceptable impedance ranges and recording, by the at least one processor, the wear offset event based on determining that the impedance level is no longer within the acceptable impedance range. In some examples, the one or more validity criteria include at least one ECG parameter derived from the one or more ECG signals satisfying a validity threshold. In some examples, the at least one ECG parameter can include R-peak amplitude and satisfying the validity threshold can include identifying at least five consecutive R-peak amplitudes that each exceed an amplitude threshold. In some examples, the at least one ECG parameter can include QRS complex width and satisfying the validity threshold can include measuring at least five consecutive QRS complex widths that are each between 0.05 seconds and 0.15 seconds. In some examples, the method further includes determining, by the at least one processor, the patient's wear compliance based on a first ECG signal of the one or more ECG signals satisfying the validity threshold.

In the method, recording the wear onset event can include detecting a skin-sensor interface impedance level at one or more of the plurality of electrodes, determining whether the impedance level is within an acceptable impedance range, and, if the impedance level is within the acceptable impedance range, record the wear onset event. In some examples, the acceptable impedance range can include at least one of a range of 20 ohms to 250 ohms, a range of 250 ohms to 1 kiloohm, and a range of 1 kiloohm to 20 kiloohms.

In the method, recording the wear onset event can include determining, by the at least one processor, whether the motion signal indicates movement of the patient and the wearable defibrillator and, if the motion signal indicates movement of the patient and the wearable defibrillator, recording, by the at least one processor, the wear onset event. In some examples, the method can further include detecting, by the at least one processor, one or more ECG signals based on the at least one electrical signal if the motion signal indicates no movement of the patient and the wearable defibrillator and recording, by the at least one processor, the wear onset event based upon analysis of the one or more ECG signals. In some examples, the method can further include detecting, by the at least one processor, one or more noise components in the at least one electrical signal and confirming, by the at least one processor, no movement of the patient based upon analysis of the one or more noise components in at least one electrical signal.

In the method, recording the wear onset event can include receiving, by the at least one processor, input from the patient specifying that the patient is wearing the wearable defibrillator and recording, by the at least one processor, the wear onset event based upon the input from the patient. In some examples, recording the wear onset event based upon the input from the patient can include confirming, by the at least one processor, the patient is wearing the wearable defibrillator based on the at least one electrical signal and the at least one motion signal and recording, by the at least one processor, the wear onset event.

In the method, recording the wear offset event can include detecting, by the at least one processor, a change in the at least one electrical signal indicating an invalid ECG signal and recording, by the at least one processor, the wear offset event based upon the invalid ECG signal.

In the method, recording the wear offset event can include detecting, by the at least one processor, a change in a skin-sensor interface impedance level at one or more of the plurality of electrodes; determining, by the at least one processor, whether the impedance level exceeds an impedance threshold; and, if the impedance level exceeds the impedance threshold, recording, by the at least one processor, the wear offset event. In some examples, the impedance threshold can include one or more of 10 kiloohms, 100 kiloohms, 1 megaohm, 2 megaohms, 5 megaohms, and 10 megaohms.

In the method, recording the wear offset event can include determining, by the at least one processor, that one or more of the plurality of electrodes and the at least one motion sensor and associated circuitry have been disconnected from the wearable defibrillator and recording, by the at least one processor, the wear offset event upon determining that one or more of the plurality of electrodes and the at least one motion sensor and associated circuitry have been disconnected.

In the method, recording the wear offset event can include detecting, by the at least one processor, that the patient has taken off the wearable defibrillator based upon analysis of the at least one motion signal; confirming, by the at least one processor, that the at least one electrical signal indicates that the patient has taken off the wearable defibrillator; and recording, by the at least one processor, the offset event based upon confirmation that the patient has taken off the wearable defibrillator.

In the method, recording the wear offset event can include receiving, by the at least one processor, input from the patient specifying that the patient is taking off the wearable defibrillator and recording, by the at least one processor, the wear offset event based upon the input from the patient. In some examples, recording the wear offset event based upon the input from the patient can include confirming, by the at least one processor, the patient has removed the wearable defibrillator based on the at least one electrical signal and the at least one motion signal and recording, by the at least one processor, the wear offset event.

In some examples of the method, the method can further include determining, by the at least one processor, a current time of day and recording, by the at least one processor, at least one of the wear onset event and the wear offset event based on one or more of the at least one motion signal, the at least one electrical signal, and the current time of day. In some examples, determining the current time of day can include determining, by the at least one processor, whether the patient has historically been in an active state or an inactive state based upon the current time of day. In some examples, the method can further include recording, by the at least one processor, at least one of the wear onset event and the wear offset event based upon the at least one electrical signal if the patient has historically been in an inactive state at the current time of day. In some examples, the method can further include recording, by the at least one processor, at least one of the wear onset event and the wear offset event based upon the at least one electrical signal and the at least one motion signal if the patient has historically been in an active state at the current time of day. In some examples, the method can further include determining, by the at least one processor, whether the patient has historically been in an active state or an inactive state based upon the current time of day and historical patient activity information recorded by the wearable defibrillator.

In the method, the notification can include an indication of patient wear compliance relative to patient wear non-compliance.

In the method, the notification can include an indication of recorded changes in wear compliance for the patient.

In the method, the notification can include a timeline illustrating recorded wear onset events and wear offset events. In some examples, the timeline can further illustrate a total time the wearable defibrillator was worn by the patient and a total time the wearable defibrillator was not worn by the patient over a user-selectable period of time.

In the method, the notification can include one or more user-selectable interface controls configured to provide access to recorded ECG information for one or more of a wear onset event, a wear offset event, and a period of time when the patient was wearing the wearable defibrillator.

In the method, outputting the notification of the patient's wear compliance can include comparing, by the at least one processor, the patient's wear compliance to one or more notification criteria and, if the patient's wear compliance satisfies at least one criterion of the one or more notification criteria, outputting, by the at least one processor, the notification. In some examples, the one or more notification criteria can include the patient failing to wear the wearable defibrillator for a certain percentage of a period of time. In some examples, the one or more notification criteria can include a recorded change in the patient's wear compliance that exceeds a compliance change threshold.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples and are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIG. 2 illustrates the output of a sample accelerometer, in accordance with an example of the present disclosure.

FIG. 9 illustrates a sample view of a user interface that a physician can access to modify compliance monitoring settings, in accordance with an example of the present disclosure.

FIGS. 11A-11D illustrate sample ambulatory medical devices that may be prescribed to a heart failure patient, in accordance with an example of the present disclosure.

DETAILED DESCRIPTION

Figure 1A:
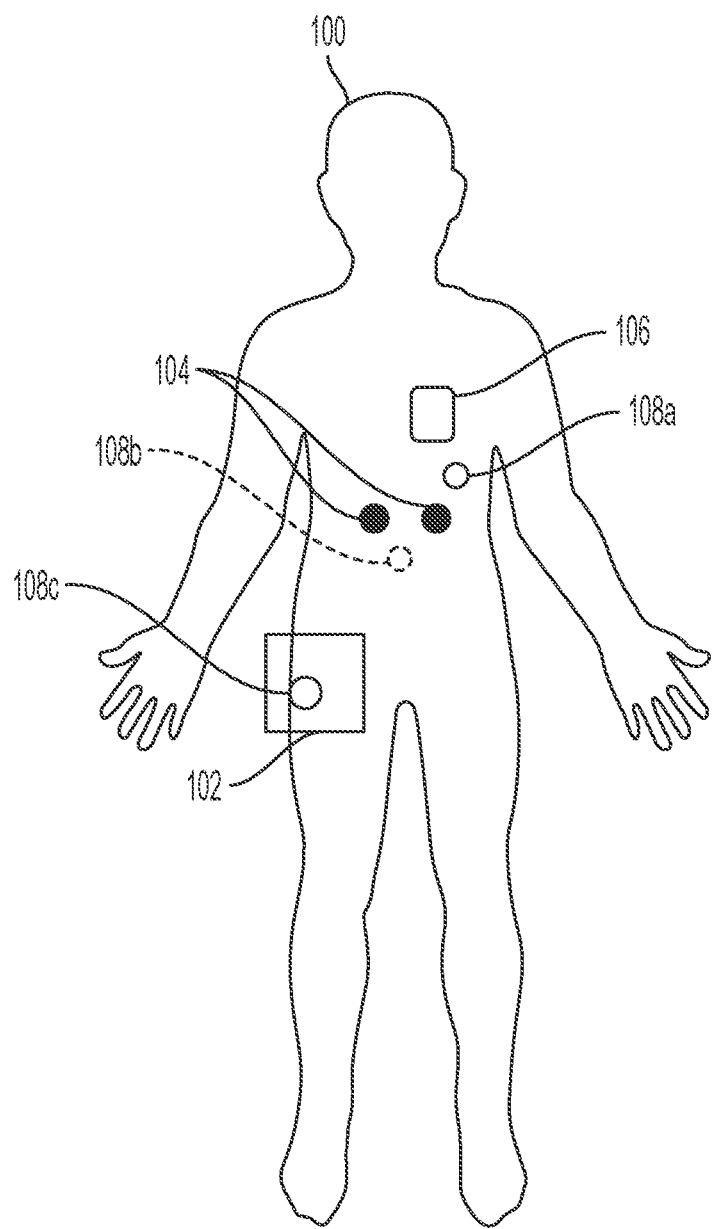
FIGS. 1A and 1B illustrate sample sensor arrangements for a patient, in accordance with an example of the present disclosure.

Wearable medical devices, such as cardiac event monitoring and/or treatment devices, are used in clinical or outpatient settings to monitor and/or record various ECG and other physiological signals of a patient. These ECG and other physiological signals can be used to monitor for arrhythmias, and, in example devices described herein, provide treatment such as defibrillation or pacing shocks in the event of life-threatening arrhythmias. An example cardiac monitoring and treatment device that can implement the wear compliance features and/or processes described herein includes a wearable defibrillator, also called wearable cardioverter defibrillator (WCDs). Another example cardiac monitoring and treatment device that can implement the wear compliance features and/or processes described herein includes a hospital wearable defibrillator (HWD).

To effectively monitor and, if needed, provide treatment to a patient, it is desirable that the patient wear the device as close to continuously as possible. To such an end, monitoring patient wear compliance information can provide feedback to both the patient's physician as well as the patient themselves. By adjusting patient habits regarding wearing of the medical device, the overall effectiveness of the cardiac monitor to the patient and the likelihood that treatment will be delivered to the patient when needed are both increased.

This disclosure relates to improved wear time monitoring techniques in order to provide the patient and/or caregiver with reliable patient compliance information, including wear time start and end times, for determining overall patient wear compliance information. In implementations as described herein, wear compliance is determined using one or more electrical signals from the patient, from which ECG information and/or body impedance measurements can be derived. The one or more electrical signals can be analyzed alone or in combination with patient motion information and/or one or more additional physiological signals to more precisely determine wear compliance.

For example, a processor in the wearable medical device as described herein can be configured to monitor for a wear compliance onset event that indicates that the patient is wearing the medical device. Following determination of the onset event, the processor can further monitor for an offset event that indicates the patient is no longer wearing the medical device. The time between onset events and corresponding offset events can be recorded and analyzed to determine overall wear compliance information for a patient over a period of time such as one day, one week, two weeks, one month, and other periods of time as described herein. In examples as described herein, the wear compliance onset and offset events can be based on physiological signals and other information including, for example, ECG signals, body impedance measurements, patient motion information, time of day information, and/or other physiological signals and collected/observed information. With respect to the physiological signals including ECG signals, the systems and methods as described herein evaluate such signals to determine that they are from patient wear, e.g., the underlying physiological and/or ECG sensors are in contact with the patient's skin.

In examples, the processor can be configured to monitor physiological signals, such as ECG signals and body impedance measurements, cardio-vibrational signals, and/or radio-frequency (RF) based physiological signals, collected by sensors associated with the medical device to determine a wear onset event. Rather than relying only on whether the medical device is on or off, or solely on patient movement information, at least some implementations herein use some combination of medical device on/off status, patient movement information, ECG signals, body impedance measurements, cardio-vibrational signals, and/or RF-based physiological information. Each of these can be weighted appropriately in a predetermined manner. For example, a wear onset event can be based on a combination where ECG signals are weighted more than patient movement information (60% ECG signals and 40% patient movement information). For example, the processor can monitor the physiological signals received from physiological sensors and combine the physiological signals with motion signals received from motion sensors to identify changes that may be indicative of an onset event. Once an onset event has been detected, the processor can continue to monitor the signals for changes that may indicate an offset event. Once an offset event has been detected, the processor can process or otherwise generate information related to the patient's wear compliance for presentation to, for example, the patient's physician or healthcare provider (HCP), the patient, or another person associated with providing care for the patient.

Wear compliance monitoring as described herein provides for various advantages and benefits. In some examples as described herein, by monitoring one or more types of patient-derived physiological signals (e.g., ECG signals, cardio-vibrational signals, RF-based signals, and/or bio-impedance signals) alone or in combination with other signals such as patient motion information for onset and offset events, the processor can accurately obtain wear compliance information indicating that the patient is actually wearing the medical device. Signals such as ECG signals, cardio-vibrational signals, bioimpedance signals, and RF-based signals are received directly from a patient wearing the medical device. If the patient is not wearing the medical device, such signals would not be available. For example, in one scenario, implementations herein use both ECG signal information and patient movement information to determine wear compliance. A system using patient movement information can be enhanced and made more reliable by implementing features described herein. As a result, implementations herein are less error-prone in determining patient wear compliance information (e.g., less likely to indicate that the patient is wearing the medical device when in fact the patient is not).

Additionally, by providing the improved wear compliance information to the patient's physician, the physician can be quickly alerted to any non-compliance by the patient. In view of the reliability of the underlying wear compliance information as described herein, physicians can act with a higher degree of confidence. In response to such an alert, the physician can take actions to correct the non-compliance before any potential adverse events happen to the patient that could have otherwise been avoided if the patient followed the wear compliance information associated with the wearable medical device.

In some examples, the systems and methods as described herein provide the improved wear compliance information to the patient. For example, the patient can access their wear compliance information or receive alerts regarding certain conditions that may or may not be met based on the improved wear compliance information. For example, if a patient is deemed to not have worn the medical device for a pre-configured period of four hours, the patient can receive a prompt on his or her phone to wear the medical device. Accordingly, by providing the improved wear compliance information, or a portion of the improved wear compliance information, to the patient, the patient can monitor and adjust their own compliance while limiting or avoiding necessary follow-up from their physician.

To address these and other aspects that enhance execution of wear compliance monitoring of a patient, systems and processes configured to accurately record wear compliance information are described herein. For example, a wearable defibrillator for providing patient wear compliance information can include a plurality of electrodes configured to monitor electrical activity of the patient and provide a therapeutic shock to the patient in response to detection of a cardiac arrhythmia based on the monitored electrical activity. Similarly, the wearable defibrillator can include at least one motion sensor and associated circuitry configured to generate at least one motion signal based upon movement of the patient. The wearable defibrillator can further include at least one processor operably coupled to the plurality of electrodes and the at least one motion sensor and associated circuitry. In some examples, the at least one processor is configured to receive at least one electrical signal based on the monitored electrical activity from the plurality of electrodes and record a wear onset event based on the ECG signals sensed from the patient's skin and the at least one motion signal indicating that the patient is wearing the wearable defibrillator. The at least one processor can be further configured to record a wear offset event based on one or more of the at least one electrical signal and the at least one motion signal indicating that the patient is not wearing the wearable defibrillator. The process can be configured to process wear compliance information based on the onset event and the offset event and output a graphical representation of the wear compliance information.

In a similar example, the processor can be configured to detect an electrocardiogram (ECG) signal from the one or more electrical signals and determine one or more of the onset event and offset event based upon changes in the ECG signal. In some examples, the processor can be configured to detect a skin-sensor impedance level at one or more of the electrodes and determine one or more of onset event and offset event based upon changes in the impedance level. In some examples, the processor can be configured to determine or confirm an onset event and/or an offset event based upon the motion signals indicating patient movement. In another example, the processor can be configured to update onset event criteria and offset event criteria based upon a measured time of day.

These examples, and various other similar examples of benefits and advantages of the techniques, processes, and approaches as provided herein, are described in additional detail below.

A patient having an elevated risk of sudden cardiac death, unexplained syncope, prior symptoms of heart failure, an ejection fraction of less than 45%, less than 35%, or other such threshold deemed of concern by a physician, and other similar patients in a state of degraded cardiac health can be prescribed specialized cardiac monitoring and treatment devices. The wear compliance monitoring features and/or processes described herein in reference to a WCD can be applied in a substantially similar manner in an HWD.

The various monitoring processes as described herein are implemented in either the WCD or HWD device itself or in data processing devices such as remote server systems that are in communication with or otherwise associated with the WCD or HWD. For example, at least some steps of the processes described herein can be executed on a server and one or more of the results of such steps can be implemented by the device.

In one example, a WCD as described herein can include the LifeVest® Wearable Cardioverter Defibrillator from ZOLL Medical Corporation (Chelmsford, MA). As described in further detail below, such a device includes a garment that is configured to be worn about the torso of the patient. The garment can be configured to house various components such as ECG sensing electrodes, therapy electrodes, one or more accelerometers configured to measure motion data for the patient, one or more audio and/or vibrational sensors configured to record vibrational signals such as cardiovibrational signals for the patient, and one or more RF sensors configured to measure RF-based physiological signals. The components in the garment can be operably connected to a monitoring device disposed within a separate housing (e.g., that may be waterproof and/or protected from ingress of dirt or other physical particles) that is configured to receive and process signals from the ECG sensing electrodes to determine a patient's cardiac condition and, if necessary, to control provision of treatment to the patient via the therapy electrodes.

An HWD can include two or more adhesive ECG sensing and/or therapy electrodes that are coupled via cables to a monitoring device disposed within a housing similar to one described above for a WCD.

The monitoring device of the WCD described herein is configured to monitor for wear onset events and wear offset events as described herein and calculate wear compliance information based upon the monitored events.

Figure 1B:
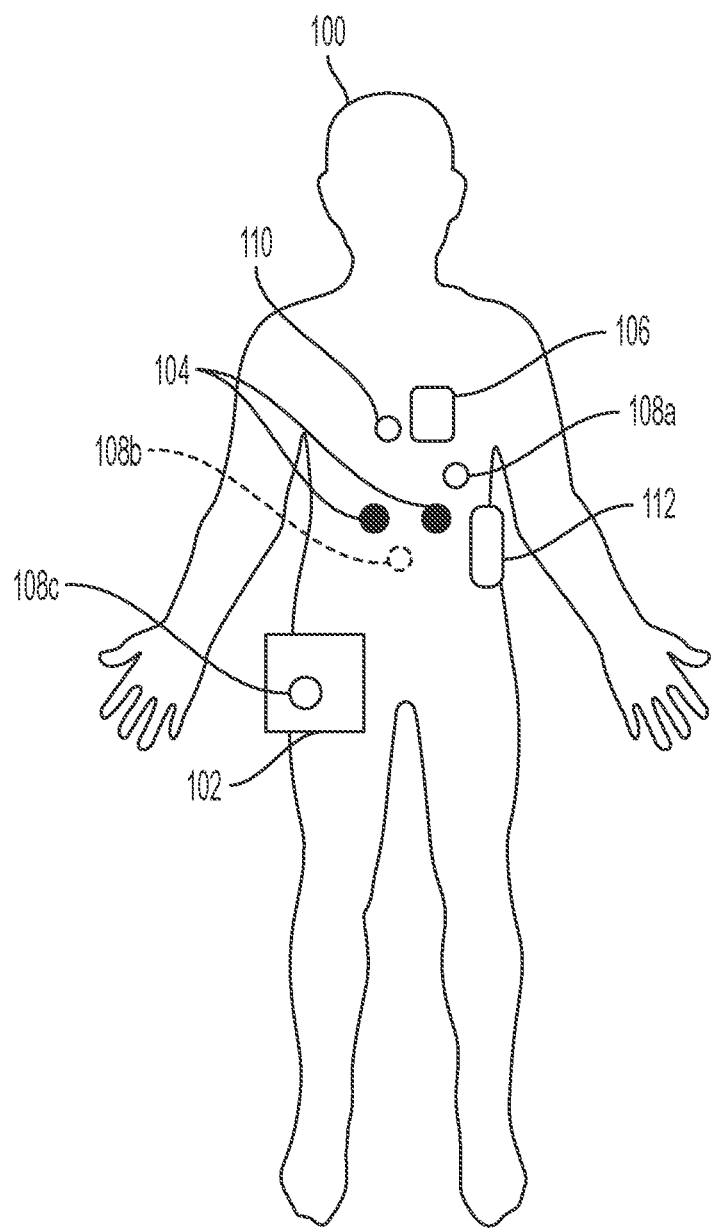

FIGS. 1A and 1B illustrate various examples of a patient 100 wearing one or more sensors such as sensing electrodes, accelerometers, audio and/or vibrational sensors, RF sensors, stretch or pressure sensors embedded in the garment, and other similar sensors as described herein. Accelerometers are described herein as examples of motion sensors for illustrative purposes only. In certain implementations, additional motion sensors such as gyroscopes, magnetic sensors, pressure-based motion sensors, and other similar motion sensors can be used.

As shown in FIG. 1A, a patient can be prescribed an ambulatory medical device such as a WCD (or, for an in-patient hospital, an HWD). The WCD can include a controller 102 that is operably connected to one or more sensing electrodes 104 and therapy electrodes 106. Additional details of examples of the controller 102, sensing electrodes 104, and the therapy electrodes 106 can be found in the discussion of FIG. 3 below.

The WCD can also include one or more accelerometers or other motion sensors. As shown in FIG. 1A, the WCD can include three accelerometers 108a, 108b, and 108c (collectively referred to as accelerometers 108) positioned at various places on the body of patient 100. For example, accelerometer 108a can be positioned on the front of chest of the patient 100, the accelerometer 108b can be positioned on the back of the patient, and the accelerometer 108c can be integrated into the controller 102. Each of the accelerometers 108 can be configured to measure movement associated with the patient 100 and to output an electrical signal indicating a direction and magnitude of the movement of the patient.

The number and arrangement of the accelerometers 108 as shown in FIG. 1 is by way of example only. In certain implementations, the number and position of the accelerometers 108 can vary. Additionally, when included in a device such as a WCD, one or more of the accelerometers 108 can be integrated into components of the WCD. For example, as noted above, the accelerometer 108c can be integrated into a controller 102 of the WCD. Similarly, one or more of accelerometers 108a and 108b can be integrated into one or more components of a WCD. For example, the front accelerometer 108a can be integrated into, for example, the therapy electrode 106, which is operably connected to the controller 102 and configured to provide a therapeutic shock to patient 100. In some implementations, the accelerometer 108a can be integrated into one of the sensing electrodes 104, which are configured to measure electrical signals produced by patient 100 and indicative of cardiac activity of the patient. Similarly, accelerometer 108b can be integrated into one or more components of a WCD such as a connection node, at least one sensing electrode 104, the therapy electrode 106, and other similar components of a WCD as described herein. Alternatively or additionally, the one or more accelerometers 108 can be distinct components of the WCD.

In HWD implementations, the accelerometers can be integrated into one or more of the adhesive ECG sensing and/or therapy electrode patches. For example, a first accelerometer can be integrated into a first adhesive ECG sensing and/or therapy electrode patch and a second accelerometer can be integrated into a second adhesive ECG sensing and/or therapy electrode patch. Additional accelerometers can be disposed within a controller (similar to controller 102 of a WCD) associated with the HWD.

In addition to accelerometers associated with a WCD as described above in regard to FIG. 1A, a patient such as patient 100 can also wear additional sensors. As shown in FIG. 1B, patient 100 can wear a vibrational sensor 110 that is configured to record bio-vibrational signals of the patient. For example, the vibrational sensor 110 can be configured to detect a patient's vibrations associated with, for example, heart and lung activity. In certain implementations, the vibrational sensor 110 can be configured to detect cardiovibrational values including any one or all of S1, S2, S3, and S4. From these cardiovibrational values, certain heart vibration metrics or combinational metrics may be calculated, including any one or more of electromechanical activation time (EMAT), left ventricular systolic time (LVST), or percentage of left ventricular systolic time (% LVST). In some examples, the vibrational sensor 110 can include a vibration sensor configured to detect vibrations from a patient's cardiac system and provide an output signal responsive to the detected cardiovibrational values. The vibrational sensor 110 can also include a multi-channel accelerometer, for example, a three-channel accelerometer configured to sense movement in each of three orthogonal axes such that patient movement/body position can be detected and correlated to detected cardiovibrational values. The vibrational sensor 110 can transmit information descriptive of the cardiovibrational values to, for example, a sensor interface for subsequent analysis as described below.

Additionally, the patient 100 can wear an RF sensor 112. For example, the RF sensor 112 can be configured to use RF-based techniques to assess fluid levels and accumulation in a patient's body tissue. For example, the RF sensor 112 can be configured to measure fluid content in the lungs, typically for diagnosis and follow-up of pulmonary edema or lung congestion in heart failure patients. Similarly, the RF sensor can be configured to measure thoracic fluid content for a patient. In certain implementations, the RF sensor 112 can include one or more antennas configured to direct radio frequency waves through a patient's tissue and measure output radio frequency signals in response to the waves that have passed through the tissue. In certain implementations, the output radio frequency signals include parameters indicative of a fluid level in the patient's tissue. The RF sensor 112 can transmit information descriptive of the tissue fluid levels to a sensor interface for subsequent analysis as described below.

It should be noted that the placement and number of sensors as shown in FIGS. 1A and 1B are shown by way of example only. In actual implementation of the wear compliance monitoring systems and methods as described herein, the number and position of the sensors can vary based upon the type of patient monitoring and/or treatment to be performed and other various factors.

To properly acquire and output a signal indicative of a patient's movement or lack thereof, an accelerometer such as those described above can be configured to output one or more output signals indicative of any detected movement or motion. For example, as shown in FIG. 2, an accelerometer 200 can be configured to measure movement in three axes: the x-axis, the y-axis, and the z-axis. Depending upon the orientation of the accelerometer 200 and the output configuration of the accelerometer, the individual axes can define movement of the accelerometer in a specific direction.

Additionally, as shown in FIG. 2, the accelerometer 200 can be configured to provide one or more outputs 202. In this example, the outputs 202 can include an X-out (i.e., a signal indicative of measured movement along the x-axis), a Y-out (i.e., a signal indicative of measured movement along the y-axis), and a Z-out (i.e., a signal indicative of measured movement along the z-axis).

In some implementations, an accelerometer such as accelerometer 200 can be configured to output an electrical signal on each output 202 having one or more controlled characteristics such as voltage. For example, the accelerometer 200 can be configured to output a signal on each output 202 between 0 and 5 volts. In some examples, the output voltage on each output 202 can be directly proportional to measured motion on the corresponding axis. For example, if the accelerometer 200 is configured to measure movement of acceleration as a measure of gravitational forces, the accelerometer can be configured to measure a specific range of g-forces such as −5 g to +5 g. In such an example, the output voltage on each output 202 can be directly proportional to the measured g-force on each axis. For example, if no g-forces are measured (i.e., the accelerometer 200 is at rest), each output signal 202 can be measured at 2.5 volts. If a movement having a positive g-force along an axis is measured, the voltage on the corresponding output 202 can increase. Conversely, if a movement having a negative g-force along an axis is measured, the voltage on the corresponding output 202 can decrease. Based upon these outputs 202, a processor such as those described herein can determine one or more motion parameters for a patient to be used when determining whether the patient is actively wearing a medical device. Additional details regarding such processes are provided below.

Table 1 below shows sample voltage output levels for an accelerometer configured to measure between −5 g and +5 g and output a signal between 0 and 5 volts.

TABLE 1

| Measured G-Force | Output Voltage |
| --- | --- |
| −5 g | 0 volts |
| −4 g | 0.5 volts |

TABLE 1-continued

| Measured G-Force | Output Voltage |
| --- | --- |
| −3 g | 1.0 volts |
| −2 g | 1.5 volts |
| −1 g | 2.0 volts |
| 0 g | 2.5 volts |
| 1 g | 3.0 volts |
| 2 g | 3.5 volts |
| 3 g | 4.0 volts |
| 4 g | 4.5 volts |
| 5 g | 5.0 volts |

Sample g-force and voltage ranges as described above and shown in Table 1 are provided by way of example only for illustrative purposes and are not intended to represent the only way in which the concepts as described herein can be implemented. Depending upon the design and capabilities of the accelerometers used, the g-force ranges measured, and the corresponding output voltages, can vary accordingly. For example, an output voltage of 10 volts can correspond to a measured G-force of 5 g. For example, an output voltage of 15 volts can correspond to a measured G-force of 5 g. For example, an output voltage of 20 volts can correspond to a measured G-force of 5 g. Likewise, an output voltage of 2 volts can correspond to a measured G-force of 1 g. For example, an output voltage of 4 volts can correspond to a measured G-force of 1 g. For example, an output voltage of 6 volts can correspond to a measured G-force of 1 g.

Figure 3:
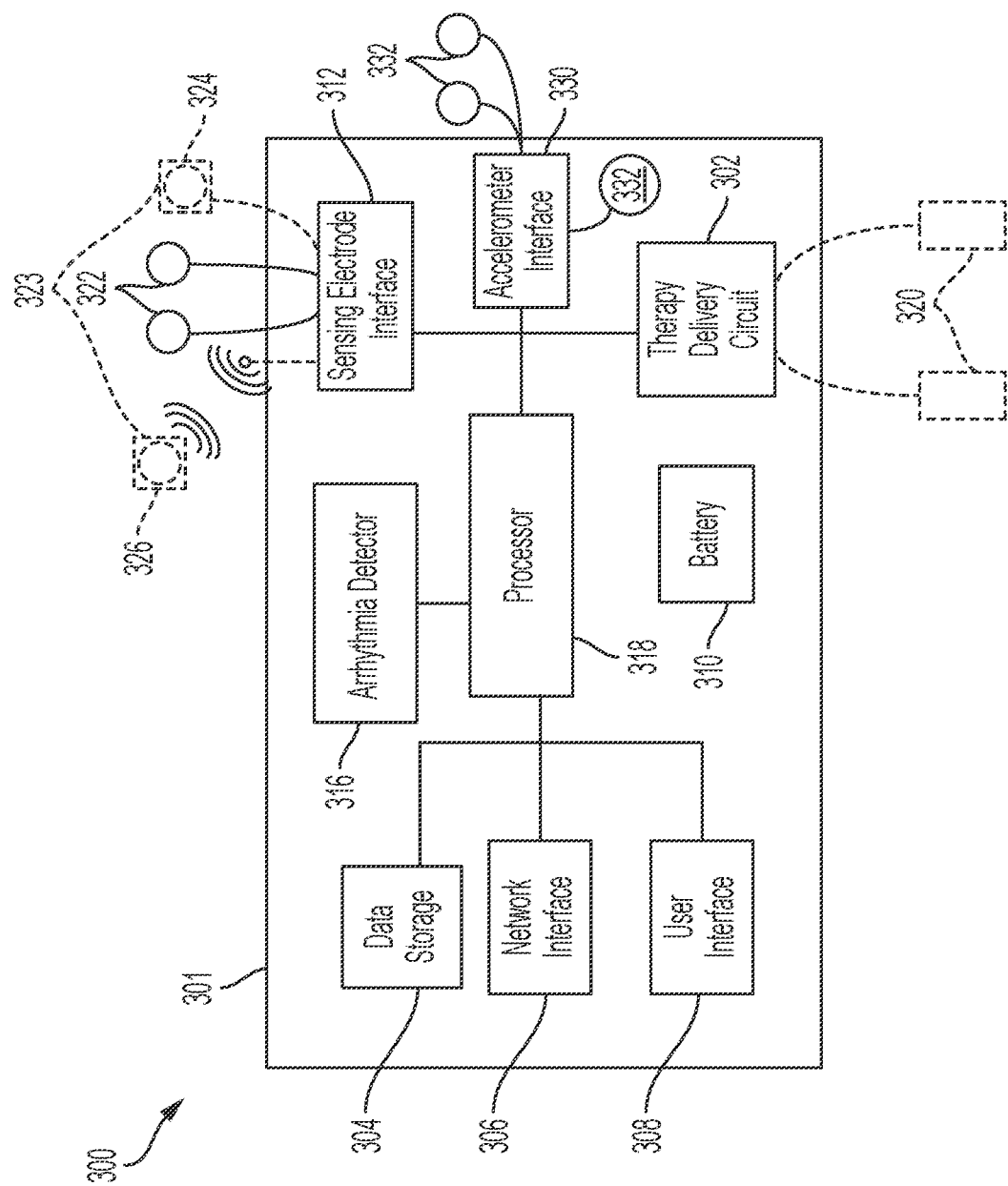
FIG. 3 illustrates a schematic view of a sample controller for a wearable medical device, in accordance with an example of the present disclosure.

FIG. 3 illustrates an example component-level view of the medical device controller 300 included in, for example, a wearable medical device such as a WCD or an HWD as described herein. The medical device controller 300 is one example of the controller 102 shown in FIGS. 1A and 1B and described above. As shown in FIG. 3, the medical device controller 300 can include a housing 301 configured to house a therapy delivery circuitry 302 configured to provide one or more therapeutic shocks to the patient via at least two therapy electrodes 320 (e.g., therapy electrode 106 as described above), a data storage 304, a network interface 306, a user interface 308, at least one rechargeable battery 310 (e.g., within a battery chamber configured for such purpose), a sensor interface 312 (e.g., to interface with both ECG sensing electrodes 322 (e.g., sensing electrodes 104 as described above) and non-ECG physiological sensors 323 such as vibrational sensors (e.g., vibrational sensor 110), lung fluid sensors (e.g., RF sensor 112), infrared and near-infrared-based pulse oxygen sensor, blood pressure sensors, among others), a cardiac event detector 316, and least one processor 318.

In some examples, the patient monitoring medical device can include a medical device controller 300 that includes like components as those described above but does not include the therapy delivery circuitry 302 and the therapy electrodes 320 (shown in dotted lines). That is, in certain implementations, the medical device can include only ECG monitoring components and not provide therapy to the patient. In such implementations, the construction of the patient monitoring medical device is similar in many respects as the medical device controller 300 but need not include the therapy delivery circuitry 302 and associated therapy electrodes 320.

As further shown in FIG. 3, the controller 300 can further include an accelerometer interface 330 and a set of accelerometers 332. The accelerometer interface 330 can be operably coupled to each of the accelerometers 332 and configured to receive one or more outputs from the accelerometers. The accelerometer interface 330 can be further configured to condition the output signals by, for example, converting analog accelerometer signals to digital signals (if using an analog accelerometer), filtering the output signals, combining the output signals into a combined directional signal (e.g., combining each x-axis signal into a composite x-axis signal, combining each y-axis signal into a composite y-axis signal, and combining each z-axis signal into a composite z-axis signal). In some examples, the accelerometer interface 330 can be configured to filter the signals using a high-pass or band-pass filter to isolate the acceleration of the patient due to movement from the component of the acceleration due to gravity.

Additionally, the accelerometer interface 330 can configure the output for further processing. For example, the accelerometer interface 330 can be configured to arrange the output of an individual accelerometer 332 as a vector expressing the acceleration components of the x-axis, the y-axis, and the z-axis as received from each accelerometer. The accelerometer interface 330 can be operably coupled to the processor 318 and configured to transfer the output signals from the accelerometers 332 to the processor for further processing and analysis.

As described above, one or more of the accelerometers 332 (e.g., accelerometers 108 as described above) can be integrated into one or more components of a medical device. For example, as shown in FIG. 3, an accelerometer 332 (e.g., accelerometer 108c as described above) can be integrated into the controller 300. In some examples, an accelerometer 332 can be integrated into one or more of a therapy electrode 320, a sensing electrode 322, a physiological sensor 323, and into other components of a medical device. When controller 300 is included in an HWD, an accelerometer can be integrated into an adhesive ECG sensing and/or therapy electrode patch.

Figure 4:
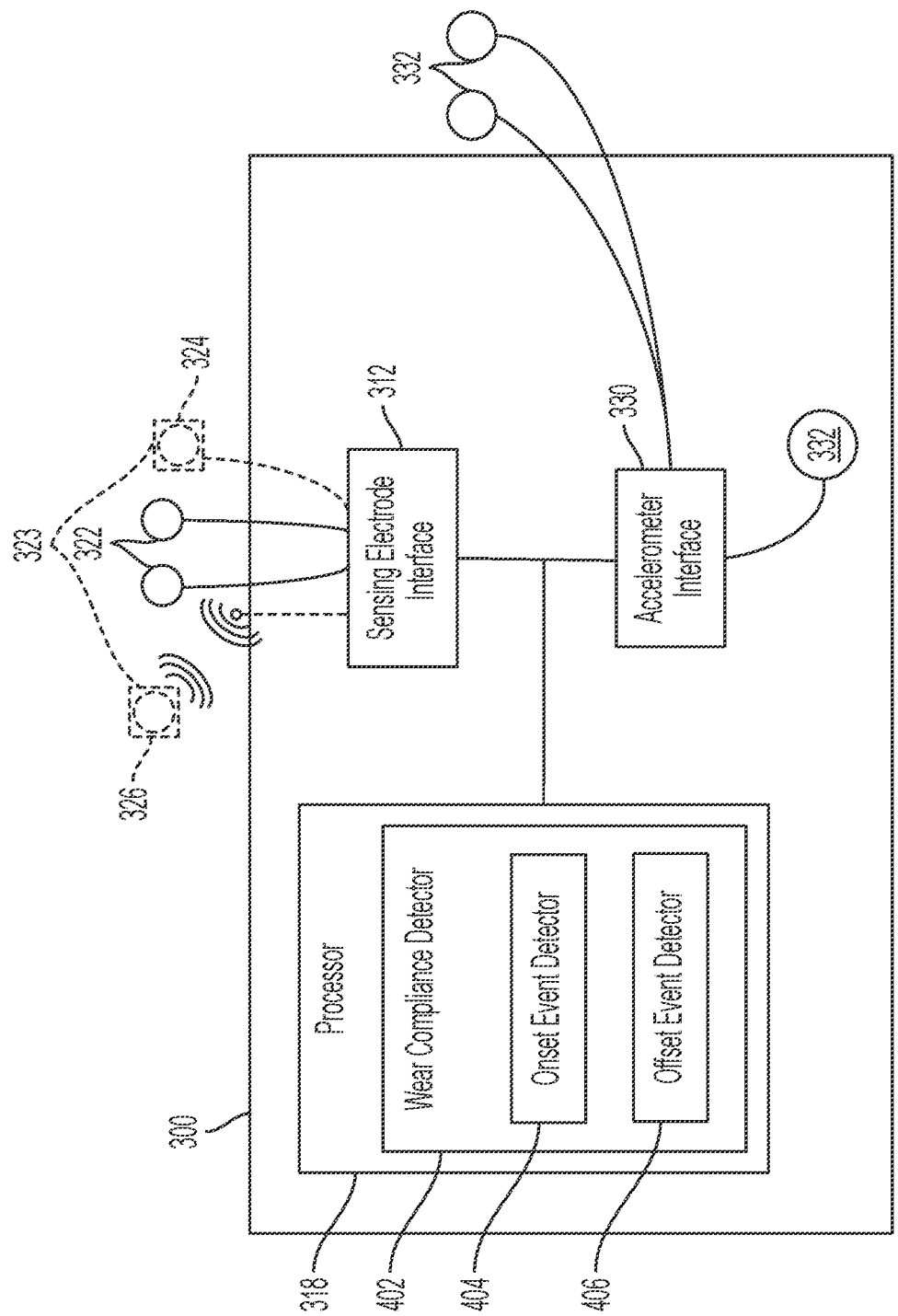
FIG. 4 illustrates a sample controller configured to monitor for wear compliance by a patient, in accordance with an example of the present disclosure.

As described herein, and noted above, the present disclosure includes monitoring medical device wear compliance for a patient. More specifically, the wear compliance information as monitored herein includes an accurate overview of what portion or percentage of a certain time period the patient has worn the medical device and how this compares to expected wear for the patient as prescribed, for example, by their healthcare provider when being prescribed the medical device. FIG. 4 illustrates an example reduced component-level view of a medical device controller 300 that includes a processor 318 that is configured to monitor wear compliance information for a patient as described herein. For example as shown in FIG. 4, the processor 318 can include a wear compliance detector 402. It should be noted that the wear compliance detector 402 is shown as integrated into processor 318. However, such a design is shown by way of example only. In certain implementations, the wear compliance detector 402 can be integrated as a separate processing component operably coupled to the processor 318. The wear compliance detector 402 can be implemented as a dedicated microprocessor and associated circuitry disposed on a printed circuit board (PCB) along with other components as described herein. The wear compliance detector 402, when implemented in a dedicated microprocessor or integrated into processor 318, can be based on a series of processor-readable instructions configured to be executed by the dedicated microprocessor or processor 318. For example, the instructions can be implemented in a programming language such as C, C++, assembly language, machine code, HDL, or VHDL. In examples, the dedicated microprocessor can be an Intel-based microprocessor such as an X86 microprocessor or a Motorola 68020 microprocessor, each of which can use a different set of binary codes and/or instructions for similar functions. The dedicated microprocessor or processor 318 can be configured to implement wear onset event detection and wear offset event detection as set forth in FIGS. 5-7.

As further shown in FIG. 4, the wear compliance detector 402 can include an onset event detector 404 and an offset event detector 406. As described above, the wear compliance detector 402 can be a dedicated microprocessor and associated circuitry disposed on a PCB along with other components as described herein. In implementations, a first microprocessor can be implemented as the onset event detector 404, and a second microprocessor can be implemented as the offset event detector 406. In some implementations, both the onset event detector 404 and offset event detector 406 can be implemented in the same microprocessor as described above. The onset event detector 404 and/or offset event detector 406, when implemented in a dedicated microprocessor or integrated into processor 318, can be based on a series of processor-readable instructions configured to be executed by the dedicated microprocessor or processor 318. For example, the instructions can be implemented in a programming language such as C, C++, assembly language, machine code, HDL, or VHDL. In examples, the dedicated microprocessor can be an Intel-based microprocessor such as an X86 microprocessor or a Motorola 68020 microprocessor, each of which can use a different set of binary codes and/or instructions for similar functions. The dedicated microprocessor or processor 318 can implement the wear onset event detection and/or wear offset event detection as set forth in FIGS. 5-7.

As noted above, when a patient puts on the medical device, a wear onset event can be determined based upon analysis of signals received from one or more of the sensors as described herein. For example, based upon monitoring of signals output by the ECG sensing electrodes as well as signals output by the accelerometers 332, the onset event detector 404 can determine an onset event indicative of the patient putting on or otherwise wearing the medical device. Similarly, the offset event detector 406 can determine an offset event indicative of the patient turning off, removing, or otherwise stopping the medical device from monitoring. Based upon the measured onset and offset events, the wear compliance detector 402 and/or the processor 318 can determine wear compliance information for the patient. Example operations executed by the processor 318, wear compliance detector 402, and the onset event detector 404 and the offset event detector 406 are described in additional detail in the following discussion of FIGS. 5-7.

Figure 5:
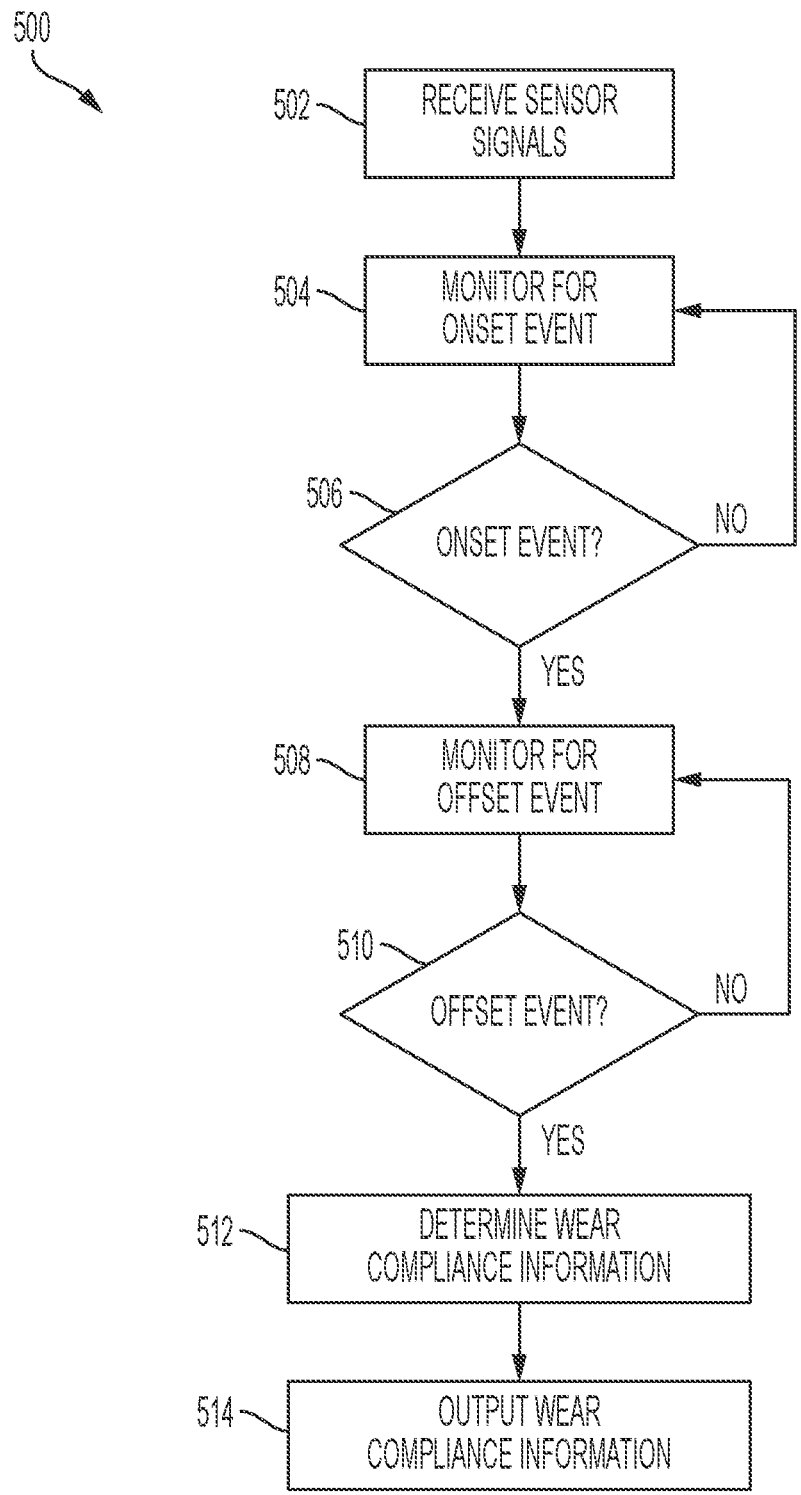
FIG. 5 illustrates a sample process flow for monitoring wear compliance of a patient, in accordance with an example of the present disclosure.

FIG. 5 illustrates a sample process flow for monitoring for and outputting patient wear compliance information as described herein. For example, the sample process 500 as shown in FIG. 5 can be implemented by a processor such as processor 318 of medical device controller 300 as described above.

As shown in FIG. 5, the processor can receive 502 one or more sensor signals from one or more patient sensors. For example, the sensor signals can include signals from one or more physiological sensors such as an ECG sensor, an RF-based physiological sensor, a bio-acoustic sensor, and other similar sensors. The sensor signals can also include signals from one or more motion sensors such as accelerometers. In some examples, the signals can also include electrical signals from one or more sensors from which various electrical parameters such as impedance measurements can be measured.

The processor can monitor 504 the received signals for an indication of a wear compliance onset event. As described herein, a wear compliance onset event, or simply an onset event, is a change in one or more monitored signals that indicates that the patient has transitioned from not wearing a wearable medical device to wearing the wearable medical device. For example, as noted herein, when a predetermined threshold based on ECG signal information is met, the patient is deemed to be wearing the wearable medical device. As an illustration, the below is an example implementation of such a feature, reproduced as a sample functional specification listing various functions and/or requirements for implementation by, for example, the processor of the medical device controller:

Find the QRS complex based on the dual criteria of the amplitude and duration of the QRS complex. In an example, use the Pan Tompkins algorithm to detect QRS. After a predetermined duration of time, called, for example, "WearTimePreOnPeriod" (e.g., 5 seconds of QRS signals or other pre-configured value, or dynamically changing value) initiate wear time (e.g., "wearTimeStart").

Dynamic changes to WearTimePreOnPeriod duration: If the signal is noisy (as indicated by, for example, variable ECGnoiseFlagMask), then the predetermined duration of time can be extended. For example, extended to around 10 seconds to allow for more ECG samples to be collected.

Dynamic changes to predetermined duration Wear TimePreOnPeriod: If QRS samples are detected for a preset portion of the WearTimePreOnPeriod duration. For example, the preset portion may be set to 80%. This means that if during 80% of the WearTimePreOnPeriod the dual criteria is met, then compliance tracking is initiated (WearTimeStart). Otherwise, the WearTimePreOnPeriod duration is extended by an additional period, for example, 3 seconds. The above dynamic check is then repeated for the extended WearTimePreOnPeriod duration. The WearTimePreOnPeriod resets when the total duration reaches a predetermined maximum (e.g., 15 seconds).

In certain implementations, the processor can be configured to receive a user input indicating that the patient has put on the wearable medical device. Depending upon the implementation, the processor can monitor one or more additional signals to confirm that the patient has put on the medical device as described herein.

During monitoring 504, the processor can determine 506 whether an onset event has occurred. If the processor determines 506 that an onset event has not occurred, the processor can continue to monitor 504 the electrical signals for an onset event. Conversely, if the processor does determine 506 that an onset event has occurred, the processor can record the onset event and monitor 508 the electrical signals for a wear compliance offset event. For example, as described herein, a wear compliance offset event, or simply offset event, is a change in one or more monitored signals that indicates that the patient has transitioned from wearing the wearable medical device to not wearing the wearable medical device.

As further shown in FIG. 5, during monitoring 508, the processor can determine 510 whether an offset event has occurred. If the processor determines 510 that an offset event has not occurred, the processor can continue to monitor the electrical signals for an offset event. Conversely, if the processor does determine 510 that an offset event has occurred, the processor can determine 512 wear compliance information for the period of time between the onset event and the offset event. The processor can then output 514 the wear compliance information to, for example, a remote server for storage and analysis. Additionally, the processor can be configured to output 514 at least a portion of the wear compliance information in a notification to the patient, a caregiver of the patient, and the prescribing physician. In such an example, the output notification can include any recorded changes in the patient's wear compliance that exceeds, for example, a compliance change threshold. For example, if a patient's wear compliance percentage changes by more than a particular amount in a day (e.g., between 5% and 15% between consecutive days), the notification can include information about the change in wear compliance.

In order to properly record the compliance information, the processor can record event information in a table or other similar data structure. For example, for each onset event and offset event measured during a particular time period, the processor can record an associated occurrence time associated with the events. The processor can further calculate and record total wear compliance time by calculating the time between an onset event and a subsequent offset event. Similarly, the processor can further calculate and record total wear non-compliance time by calculating the time between an offset event and a subsequent onset event. When computing wear compliance on a daily basis, the processor may record an offset event at midnight as time transitions from one day to another and immediately record an onset event at midnight as well. Such recording provides a demarcation between days without recording any non-compliant periods of time.

Figure 6A:
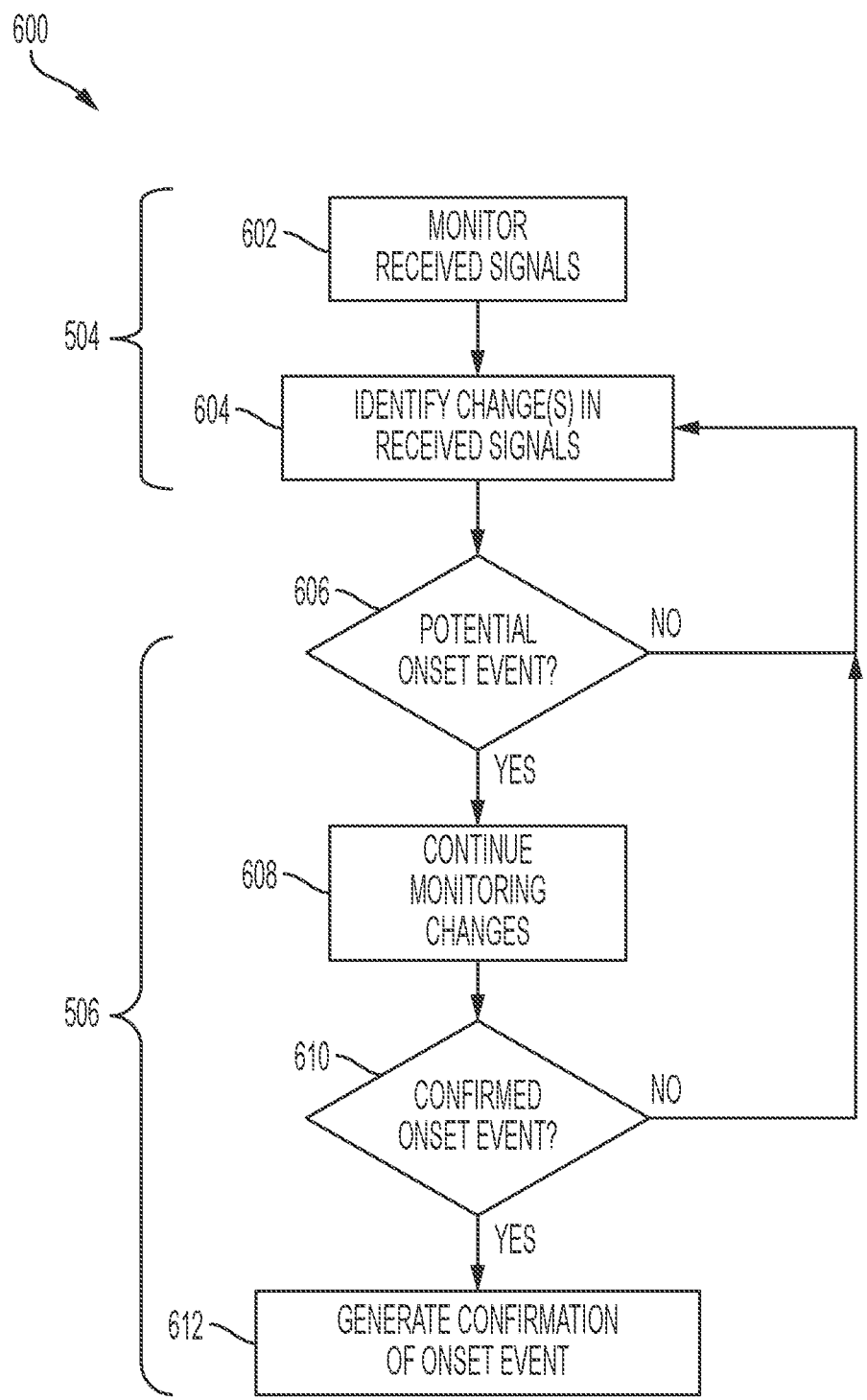
FIG. 6A illustrates a sample process flow of monitoring for and confirming an onset event, in accordance with an example of the present disclosure.

Table 2 below illustrates a sample data structure for recording wear compliance information as described herein. As shown, Table 2 includes wear compliance information calculated daily and, as such, includes an offset and onset event pair at midnight of each day. Table 2 also includes total time between events (segment on time) as well as total overall daily wear measurements (cumulative day on time, cumulative day off time, and total daily compliance %).

for an indication of an onset event. Process 640 as shown in FIG. 6C includes a more specific implementation where one or more motion signals are monitored for an indication of an onset event. Process 660 as shown in FIG. 6D includes a more specific implementation where one or more skin-sensor interface impedance levels are monitored for an indication of an onset event.

As noted above, process 600 as shown in FIG. 6A illustrates a more detailed process flow for monitoring 504 and determining 506 as shown in FIG. 5 and described above. As shown in FIG. 6A, the processor can monitor 602 the received signals. The processor can identify 604 any changes in the received signals that may indicate an occurrence of an onset event. The processor can determine 606 if the changes are indicative of an onset event by, for example, comparing the changes in the received signals against one or more onset event criteria. Examples of specific onset event criteria are described in the following discussions of FIGS. 6B-6C.

As further shown in FIG. 6A, if the processor determines 606 that the changes in the received signals are not indicative of an onset event, the processor can continue to search for and identify 604 changes in the received electrical signals. If, however, the processor does determine 606 that the changes in the received signals are indicative of an onset event, the processor can continue to monitor 608 the changes. For example, depending upon the type of onset event criteria used to determine an occurrence of an onset event, the changes to an electrical signal must be maintained or observed over a particular period of time such as, for example, five seconds. The processor can determine 610 if the potential onset event is a confirmed onset event based upon the extended monitoring of the changes. If the processor does not determine 610 that the potential onset event is a confirmed onset event, the processor can continue to search for and identify 604 changes in the received signals. Conversely, if the processor does determine 610 that the potential onset event is a confirmed onset event, the processor can generate 612 confirmation of the onset event and

TABLE 2

| Day | Onset Event Time | Offset Event Time | Segment On Time | Cumulative Day On Time | Cumulative Day Off Time | Total Daily Compliance % |
|---|---|---|---|---|---|---|
| 1 | 0:00 | 9:35 | 9:35 | 9:35 | 0:00 | 39.9% |
| 1 | 10:05 | 17:35 | 7:30 | 17:05 | 0:30 | 71.1% |
| 1 | 18:00 | 24:00 | 6:00 | 23:05 | 0:55 | 96.1% |
| 2 | 0:00 | 9:15 | 9:15 | 9:15 | 0:00 | 38.5% |
| 2 | 9:40 | 18:15 | 8:35 | 17:50 | 0:25 | 74.3% |
| 2 | 18:30 | 24:00 | 5:30 | 23:20 | 0:40 | 97.2% |
| 3 | 0:00 | 8:15 | 8:15 | 8:15 | 0:00 | 34.4% |
| 3 | 9:00 | 16:30 | 7:30 | 15:45 | 0:45 | 65.6% |
| 3 | 17:15 | 24:00 | 6:45 | 22:30 | 1:30 | 93.7% |

As noted above, the processor can be configured to monitor one or more electrical signals for an occurrence of an onset event. However, in certain implementations, the processor can be configured to monitor for and rely upon changes in particular signals for an indication of an onset event. For example, process 600 as shown in FIG. 6A includes a more detailed process flow for monitoring 504 sensor signals and determining 506 whether an onset event has occurred. In certain implementations, the sensor signals can include a combination of signals such as physiological signals as well as motion signals. Process 620 as shown in FIG. 6B includes a more specific implementation where one or more physiological signals of the patient are monitored record, for example, the onset event in a data structure such as Table 2 as described above.

In some examples, the wearable medical device can include a user interface that provides the patient with the option to input various information. For example, the user interface can provide the user with an input indicating that they have put on the wearable medical device. In response to such an input, the processor can confirm the onset event using a process similar to that as shown in FIG. 6A by analyzing at least one of the one or more physiological signals and/or motion signals and record the onset event. In some examples, the processor can record the onset event solely based upon the patient input.

As noted above, process 600 as shown in FIG. 6A is directed to detection of an onset event by monitoring generally received signals from one or more sensors as described herein. Process 620 as shown in FIG. 6B illustrates a more detailed process flow for monitoring 504 and determining 506 as shown in FIG. 5 and described above wherein physiological information for the patient is monitored and analyzed to determine, for example, an onset event occurrence. As shown in FIG. 6B, the processor can receive 622 signals from, for example, one or more physiological sensors and associated circuitry such as ECG sensors as described herein that are configured to output one or more electrical signals indicative of cardiac activity of the patient. The processor can derive 624 one or more physiological metrics from the received physiological signals. For example, the physiological metrics can include ECG metrics including, for example, heart rate (such as average, median, mode, or other statistical measure of the heart rate, and/or maximum, minimum, resting, pre-exercise, and post-exercise heart rate values and/or ranges), heart rate variability metrics, premature ventricular contraction (PVC) burden or counts, atrial fibrillation burden metrics, pauses, heart rate turbulence, QRS height, QRS width, changes in a size or shape of morphology of the ECG information, cosine R-T, artificial pacing, QT interval, QT variability, T wave width, T wave alternans, T-wave variability, and ST segment changes. ECG metrics are described herein by way of example only and additional physiological metrics such as those described, for example, in the detailed discussion of FIG. 3 below can be processed by the process as well.

Figure 6B:
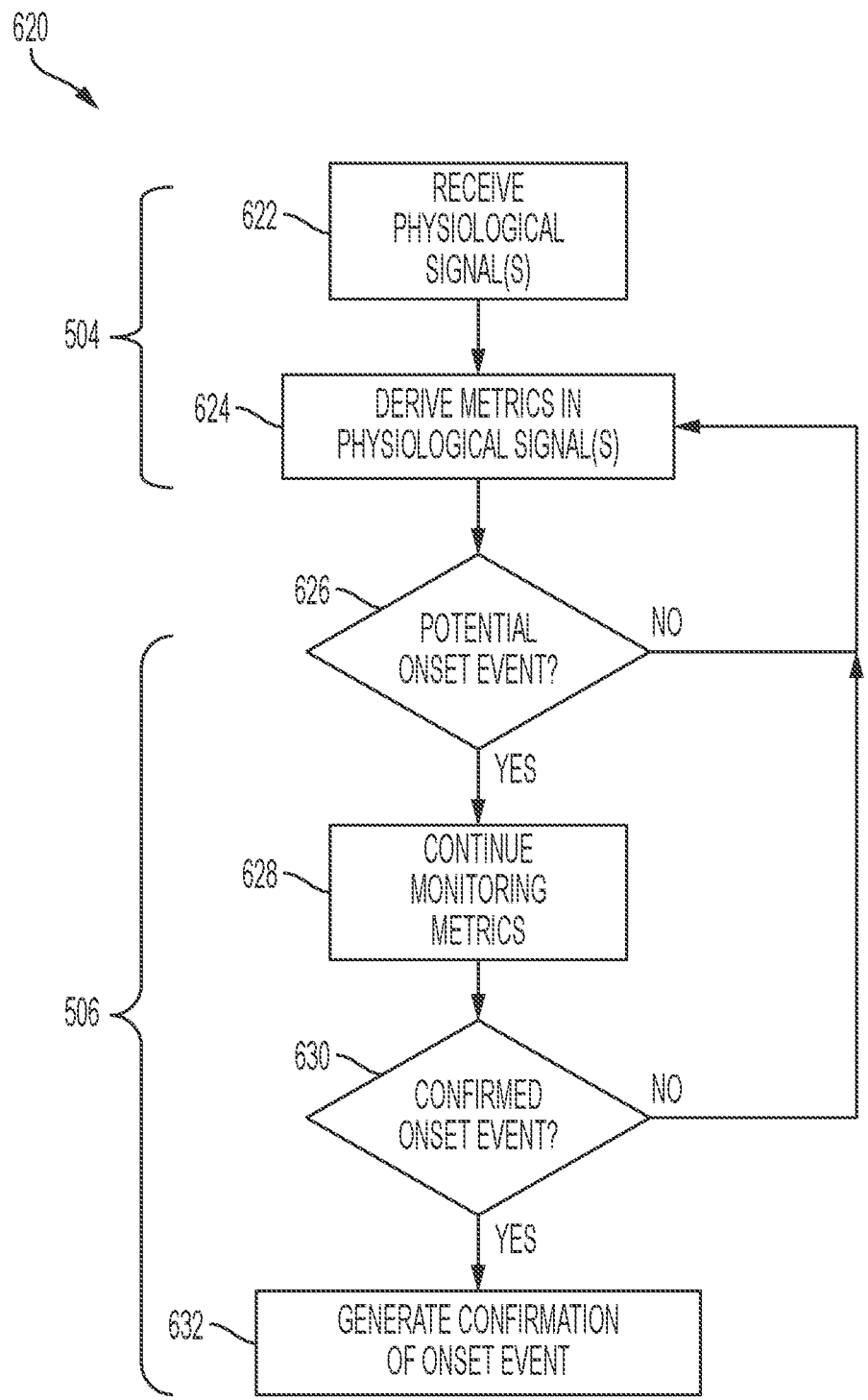
FIG. 6B illustrates a sample process flow of monitoring for and confirming an onset event by identifying changes in one or more physiological signals, in accordance with an example of the present disclosure.
Figure 6C:
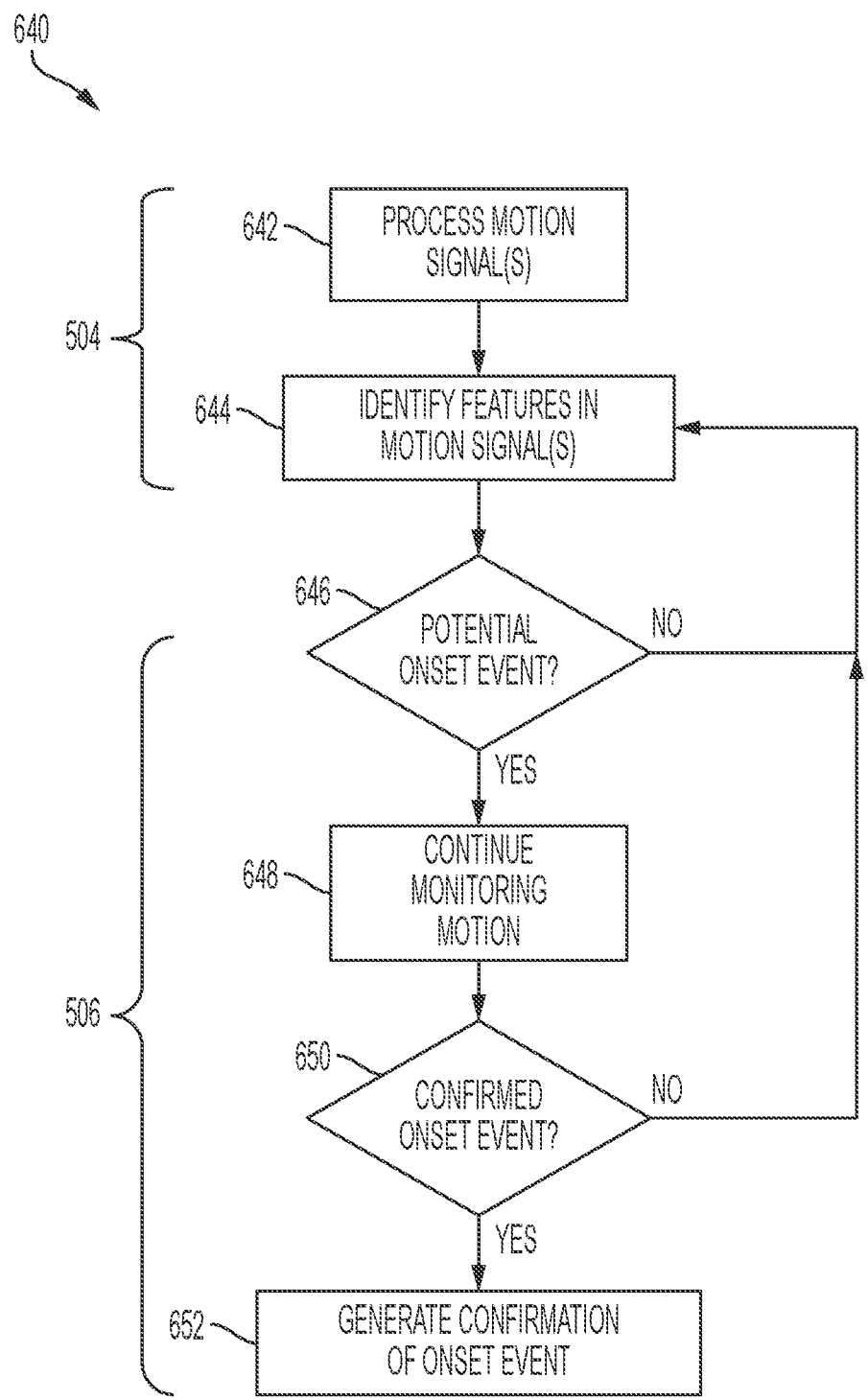
FIG. 6C illustrates a sample process flow of monitoring for and confirming an onset event by identifying changes in one or more motion signals, in accordance with an example of the present disclosure.
Figure 6D:
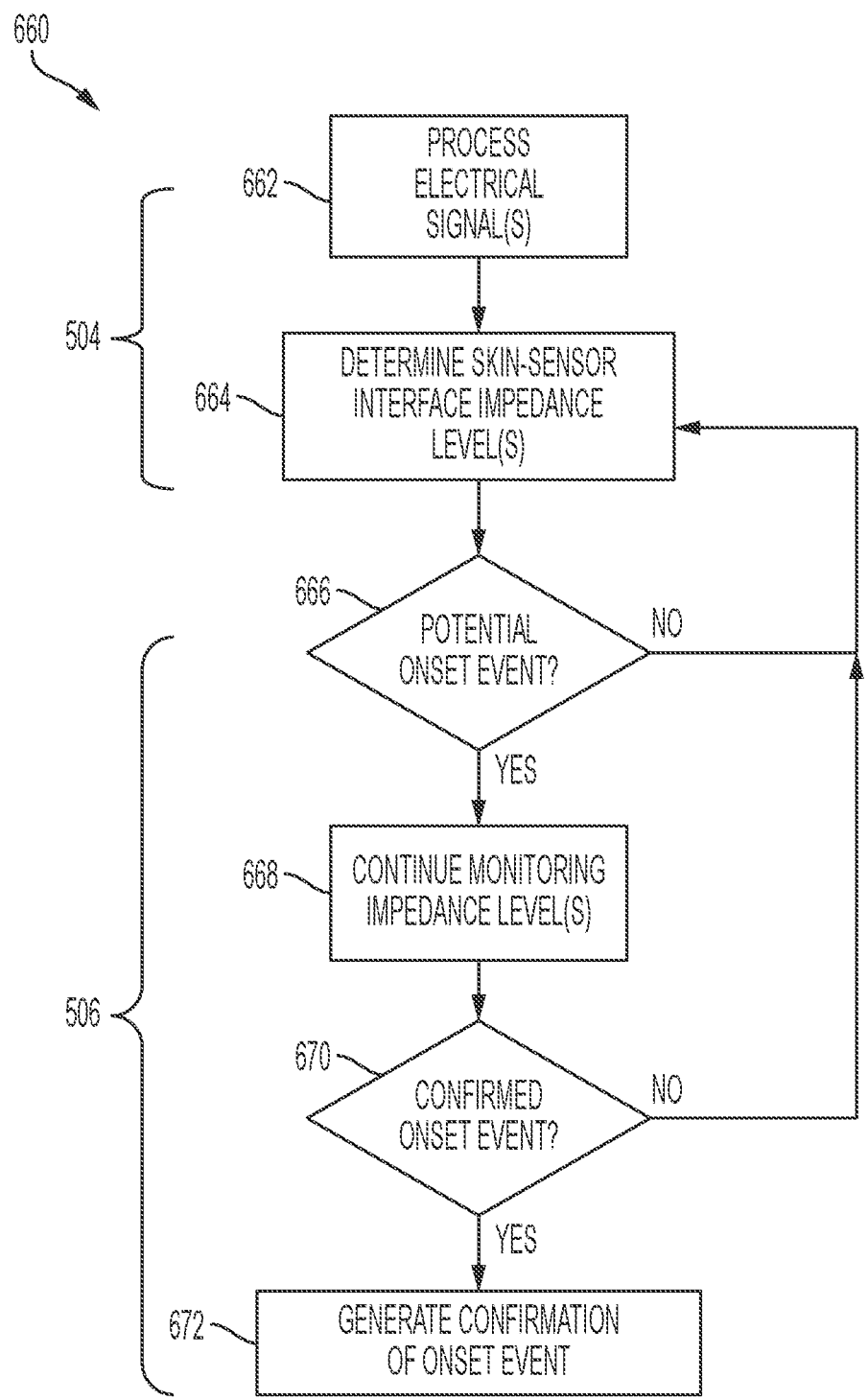
FIG. 6D illustrates a sample process flow of monitoring for and confirming an onset event by identifying changes in impedance at one or more electrodes, in accordance with an example of the present disclosure.

As further shown in FIG. 6B, the processor can determine 626 if the derived metrics are indicative of an onset event by, for example, comparing the metric changes and/or patterns in the received signals against one or more onset event criteria. For example, one onset event criteria that may be indicative of an onset event is an ECG signal that is determined to be valid for a particular period of time. In certain implementations, at least one ECG parameter as derived from the ECG signal should satisfy a validity threshold for the ECG signal to be determined as valid. The processor can use example criteria to satisfy the validity threshold as described in the following examples. For example, the ECG parameter can include a set of at least five consecutive R-peaks having an R-peak amplitude that satisfies an R-peak amplitude threshold. For example, the R-peak amplitude threshold can be between about 0.75 millivolts and 1.50 millivolts. In some examples, the R-peak amplitude threshold can be selected from about 0.50 millivolts to about 1.0 millivolt. In another example, the at least one ECG parameter can include QRS complex width. In such an example, a validity threshold for a valid ECG signal can include 5 or more consecutive QRS complexes having a width between about 0.05 seconds and 0.15 seconds. As an illustration, the below is an example sample functional specification listing various functions and/or requirements for implementation by the processor of the medical device:

Find the QRS complex based on the dual criteria of the amplitude and duration of QRS complex. In an example, use the Pan Tompkins algorithm to detect a QRS complex. After a predetermined duration of time, e.g., Wear TimePreOnPeriod (e.g., 5 seconds of QRS signals or other pre-configured value, or dynamically changing value) initiate wear time (wearTimeStart) (validity criteria is met), The below are options for determining when the validity criteria is met:

Set of at least five consecutive R-peaks having an R-peak amplitude that satisfies an R-peak amplitude threshold.

R-peak amplitude threshold can be between about 0.75 millivolts and 1.50 millivolts. Optionally, R-peak amplitude threshold can be selected from about 0.50 millivolts to about 1.0 millivolt.

QRS complex width of a user-defined value can be set. 5 or more consecutive QRS complexes having a width between about 0.05 seconds and 0.15 seconds.

As further shown in FIG. 6B, if the processor determines 626 that the derived metrics are not indicative of an onset event (e.g., the validity criteria is not met), the processor can continue to derive 624 metrics from the received physiological signals. If, however, the processor does determine 626 that the derived metrics in the received physiological signals are indicative of an onset event (e.g., the validity criteria is met), the processor can continue to monitor 628 the derived metrics. As noted above, in this example, in order to satisfy a set of example validity criteria, five consecutive R-peak amplitudes should exceed an R-peak amplitude threshold. The processor can determine 630 if the derived metrics indicate confirmation of an onset event. If the processor does not determine 630 that the potential onset event is a confirmed onset event, the processor can continue to derive metrics based upon the received physiological signals. Conversely, if the processor does determine 630 that the potential onset event is a confirmed onset event, the processor can generate 632 confirmation of the onset event and record, for example, the onset event in a data structure such as Table 2 as described above.

Process 640 as shown in FIG. 6C illustrates a more detailed process flow for monitoring 504 and determining 506 as shown in FIG. 5 and described above wherein motion information for the patient is monitored and analyzed to determine, for example, an onset event occurrence. As shown in FIG. 6C, the processor can receive 642 signals from, for example, one or more motion sensors and associated circuitry such as accelerometers as described herein that are configured to output one or more electrical signals indicative of physical activity or motion of the patient. The processor can identify 644 one or more features in the motion signals that are indicative of a particular movement of the patient. For example, motion signals can provide an indication that the patient is walking, running, climbing stairs, sitting up, standing up, sitting down, laying down, and performing other similar physical activities.

As further shown in FIG. 6C, the processor can determine 646 if the identified motion features are indicative of an onset event by, for example, determining whether the motion features are consistent with movement of the wearable medical device when being worn by the patient. For example, the output of the accelerometers may be compared against historic motion information for the patient. If the motion features match the historic motion information, the patient may be considered to be wearing the wearable medical device.

As further shown in FIG. 6C, if the processor determines 646 that the identified features in the motion signals are not indicative of an onset event, the processor can continue to identify 644 features in the received motion signals. If, however, the processor does determine 646 that the identified features in the motion signals are indicative of an onset event, the processor can continue to monitor 648 the motion signals. For example, in order to be considered valid motion, the motion signals may be required to indicate consistent movement of the patient and the wearable medical device for a period of time such as five seconds. The processor can determine 650 if the motion signals, and the identified features therein, indicate confirmation of an onset event. If the processor does not determine 650 that the potential onset event is a confirmed onset event, the processor can continue to identify 644 features in the received motion signals. Conversely, if the processor does determine 650 that the potential onset event is a confirmed onset event, the processor can generate 652 confirmation of the onset event and record, for example, the onset event in a data structure such as Table 2 as described above.

In addition to physiological signal and motion signal analysis as described above, additional signal analysis can be performed by the processor to determine an onset event. For example, the processor can measure a skin-sensor interface impedance level for each of the sensors coupled to the patient's body. An acceptable impedance range can selected by a user such as a device technician when the medical device is initially configured or otherwise programmed. For example, the acceptable impedance range can be chosen by design to be between about 20 ohms to about 250 ohms, between about 20 ohms to about 10 kiloohms, between about 20 ohms to about 20 kiloohms, between about 250 ohms to about 1 kiloohm, or between about 1 kiloohm to about 20 kiloohms. Other acceptable impedance ranges may be implemented during a design phase, a programming phase, a testing phase, and other similar evaluation periods as illustrated in the below example implementation of sample pseudocode for the processor of the medical device controller:

Measure skin-electrode interface impedance.
After a predetermined duration of time in which the impedance value stays within a 5% range of a user defined value, e.g., WearTimePreOnPeriod (e.g., 5 seconds) initiate wear time (e.g., wearTimeStart) (validity criteria is met). The below are options for determining when the validity criteria is met:
Measured skin-electrode interface impedance is within a user defined impedance range between about 20 ohms to about 250 ohms,
Measured skin-electrode interface impedance is within a user defined impedance range between about 20 ohms to about 10 kiloohms,
Measured skin-electrode interface impedance is within a user defined impedance range between about 20 ohms to about 20 kiloohms,
Measured skin-electrode interface impedance is within a user defined impedance range between about 250 ohms to about 1 kiloohm, OR
Measured skin-electrode interface impedance is within a user defined impedance range between about 1 kiloohm to about 20 kiloohms.

Based upon measurement of changes of the impedance level, the processor can determine whether an onset event has occurred. For example, in an implementation depending on certain design choices, when a sensor is not in contact with a patient's skin, the impedance can exceed 10 kiloohms. When the sensor is in contact with the patient's skin, the impedance can drop significantly. As such, if the processor measures a skin-sensor interface impedance level between about 20 ohms and about 250 ohms, the processor can determine that the sensor is in contact with the patient's skin and that an onset event has occurred. In some examples, the impedance level can be between about 10 ohms and about 300 ohms to detect an onset event. In actual implementation, the impedance level can be determined based upon the materials used to construct the sensor and the location of the placement of the sensor on the patient. For example, depending upon the type of sensors used, the impedance level during an onset event can be between an acceptable impedance range, e.g., between about 250 ohms and about 1 kiloohm, or between about 1 kiloohm and about 20 kiloohms.

More specifically, FIG. 6D illustrates a sample process flow 660 for monitoring 504 and determining 506 as shown in FIG. 5 and described above wherein a skin-sensor interface impedance level is monitored and analyzed for one or more sensors coupled to the patient's body to determine, for example, an onset event occurrence. As shown in FIG. 6D, the processor can receive 662 electrical signals from, for example, one or more sensors and associated circuitry contained therein such as conditioning and/or skin-sensor interface modeling circuitry as described in, for example, U.S. patent application Ser. No. 15/381,206 titled "Electrode Falloff Detection," filed Dec. 16, 2016, the content of which incorporated herein by reference in its entirety. Based upon the received electrical signals, the processor can determine 664 a skin-sensor interface impedance level for each of the one or more sensors coupled to the patient body.

As further shown in FIG. 6D, the processor can further determine 666 if the skin-sensor interface impedance levels for the one or more sensors are indicative of an onset event by, for example, determining whether a current skin-sensor interface impedance level at one or more of the sensors are indicative that the sensor is currently in contact with the skin of the patient. For example, as noted above, if the current skin-sensor interface impedance level for a sensor is between about 20 ohms and about 250 ohms, the processor can determine 666 that the sensor is in contact with the patient's skin and that an onset event may have occurred. Conversely, if the current skin-sensor interface impedance level for a sensor is outside the above-identified impedance range and/or exceeds a certain impedance value such as 10 kiloohms or 20 kiloohms, the processor can determine 666 that the sensor is not in contact with the patient's skin and that no onset event is likely to have occurred. In such an example, the processor can continue to determine 664 updated skin-sensor interface impedance levels for each of the one or more sensors.

As further shown in FIG. 6D, if the processor does determine 666 that the current skin-sensor interface impedance levels are indicative of a potential onset event, the processor can continue to monitor 668 the skin-sensor interface impedance levels. For example, the processor can continue to monitor the skin-sensor interface impedance levels for a set period of time such as two seconds, five seconds, 10 seconds, 15 seconds, 20 seconds, and/or 30 seconds. During the set period of time, the processor can determine 670 if the skin-sensor interface impedance levels for the one or more sensors, and any changes to the skin-sensor interface impedance levels monitored during the set period of time, indicate confirmation of an onset event. For example, if the monitored skin-sensor interface impedance levels for each of one or more sensors remains within a range of about 20 ohms to about 250 ohms for the entire set period of time, the processor can determine 670 and confirm that an onset event has occurred. Conversely, if the monitored skin-sensor impedance level for each of the one or more sensors falls outside of the above-identified impedance range during the set period of time, the processor can determine 670 that a confirmed onset event has not occurred, and the processor can continue to determine 664 skin-sensor interface impedance levels as described above. If the processor does determine 670 that the potential onset event is a confirmed onset event, the processor can generate 672 confirmation of the onset event and record, for example, the onset event in a data structure such as Table 2 as described above.

Figure 7A:
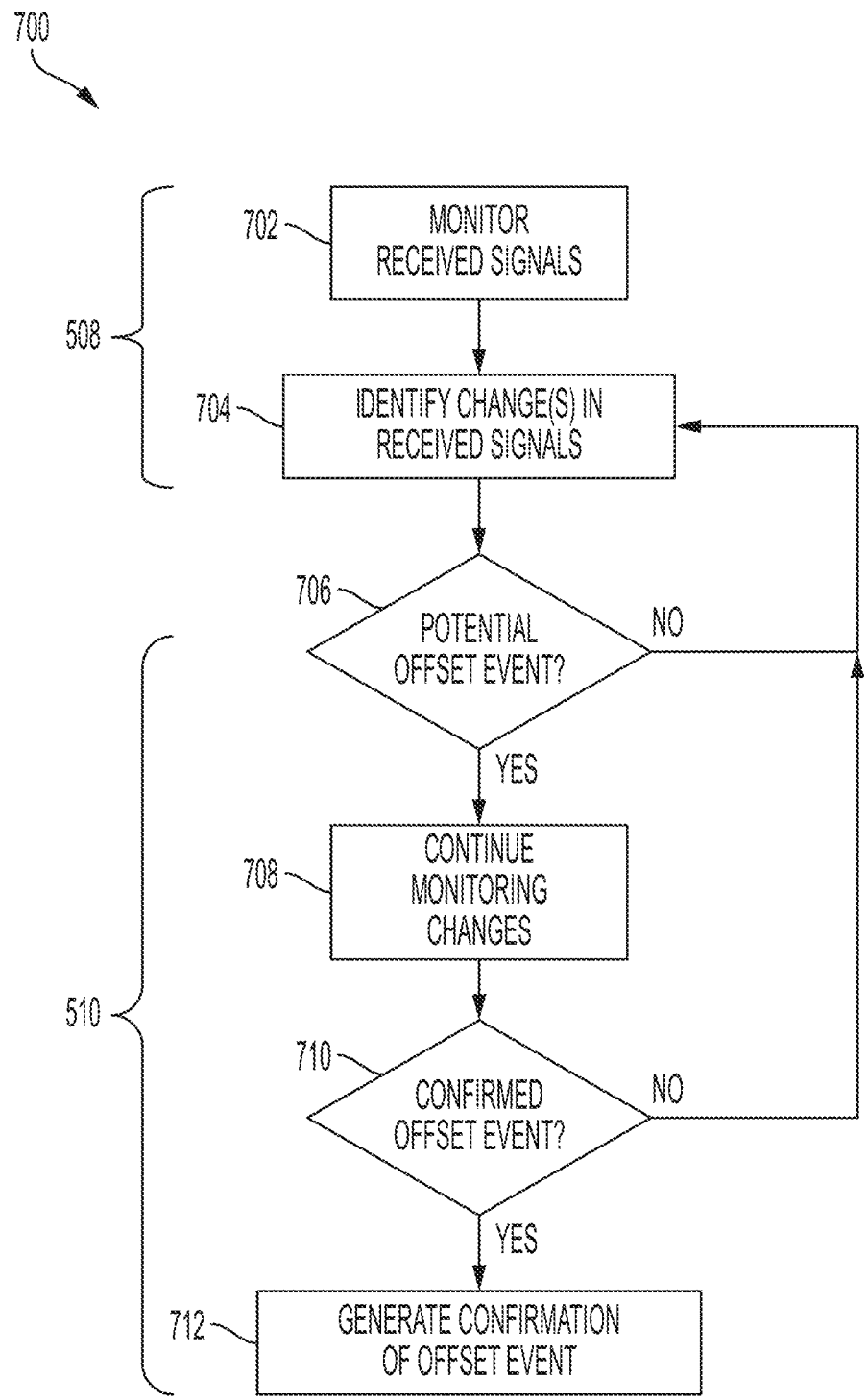
FIG. 7A illustrates a sample process flow of monitoring for and confirming an offset event, in accordance with an example of the present disclosure.

Process 700 as shown in FIG. 7A illustrates a more detailed process flow for monitoring 508 and determining 510 an offset event as shown in FIG. 5 and described above. As shown in FIG. 7A, the processor can monitor 702 the received signals. The processor can identify 704 any changes in the received signals that may indicate an occurrence of an offset event. The processor can determine 706 if the changes are indicative of an offset event by, for example, comparing the changes in the received signals against one or more offset event criteria.

As further shown in FIG. 7A, if the processor determines 706 that the changes in the received signals are not indicative of an offset event, the processor can continue to search for and identify 704 changes in the received electrical signals. If, however, the processor does determine 706 that the changes in the received signals are indicative of an offset event, the processor can continue to monitor 708 the changes. For example, depending upon the type of offset event criteria used to determine an occurrence of an offset event, the changes to an electrical signal must be maintained or observed over a particular period of time such as, for example, five seconds. The processor can determine 710 if the potential offset event is a confirmed offset event based upon the extended monitoring of the changes. If the processor does not determine 710 that the potential offset event is a confirmed offset event, the processor can continue to search for and identify 704 changes in the received signals. Conversely, if the processor does determine 710 that the potential offset event is a confirmed offset event, the processor can generate 712 confirmation of the offset event and record, for example, the offset event in a data structure such as Table 2 as described above.

In certain examples of the process 700 as shown in FIG. 7A, the criteria for determining an offset event can vary. For example, if a valid ECG signal transitions to an invalid ECG signal indicative of removal of the wearable medical device, the processor can record the offset event. Similarly, if the processor detects a change in the skin-sensor interface impedance level that exceeds an impedance threshold and is indicative of removal of the sensors from the patient's skin, or the skin-sensor interface impedance level is no longer within an acceptable impedance range, the processor can record an offset event. In some examples, the impedance threshold can include at least one of 10 kiloohms, 20 kiloohms, 100 kiloohms, one megaohm, two megaohms, five megaohms, and 10 megaohms. In some examples, if the processor stops receiving a signal from the one or more motion sensors, the processor can determine that the one or more motion sensors and associated circuitry have been disconnected and record an offset event accordingly. The processor can further determine that changes in the one or more motion signals indicate that the patient has removed the wearable medical device and can record an offset event accordingly. In some examples, the processor can receive an input from the patient indicating that the patient has removed the wearable medical device. The processor can confirm that the patient has removed the wearable medical device based upon changes in the one or more physiological signals and the one or more motion signals and record an offset event accordingly.

In certain implementations, determination of an onset event can be based upon a combination of signals. As such, the examples shown in FIGS. 6B, 6C, and 6D are shown by way of example only. For example, as shown in FIG. 6A, the processor can be configured to monitor both one or more physiological signals as well as one or more motion signals in concert to determine whether an onset event has occurred or not. For example, the processor can determine a valid ECG signal as described in FIG. 6B. However, prior to confirming that an onset event has occurred, the processor can further analyze the one or more motion signals as described in FIG. 6C to confirm that the one or more motion signals also provide indication of an onset event. Conversely, if the processor detects no indicated movement in the motion signals, or a high level of noise in the motion signals, the processor can record an onset event based solely upon analysis of the one or more physiological signals. Similarly, the processor can further monitor skin-sensor interface impedance levels as described in FIG. 6D in concert with monitoring physiological signals and/or motion signals to determine and confirm an onset event. Conversely, if the processor determines changes in skin-sensor impedance levels that are indicative of potential noise and/or other similar interference at one or more sensors, the processor can rely upon further analysis of the one or more physiological signals and/or motion signals to confirm an onset event as described herein. Similarly, the processor can analyze different types and combinations of signals before confirming an offset event as shown in FIG. 7A.

However, in certain examples, additional variables can impact the reliability of one or more signals. For example, at particular times of the day, patient movement may be limited. For example, at night, patient movement may be limited and, as such, the criteria used for onset and offset event determination can be adjusted accordingly. In such an example, the processor can be configured to record an onset and/or offset event based upon one or more physiological signals, one or more motion signals, and the time of day.

Figure 7B:
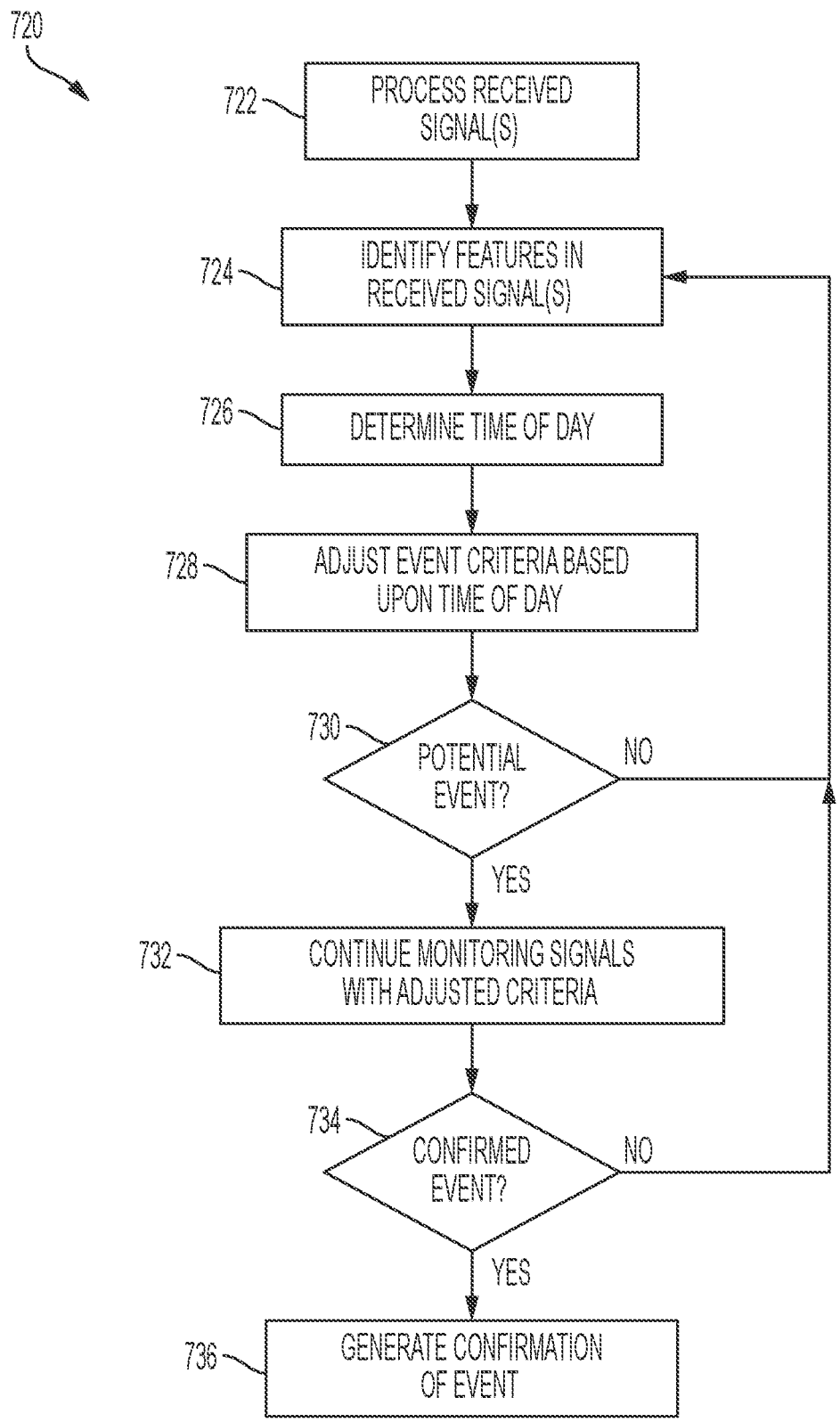
FIG. 7B illustrates a sample process flow for monitoring for and confirming an event based upon time of day, in accordance with an example of the present disclosure.

Process 720 as shown in FIG. 7B includes consideration of the time of day and adjusts event criteria accordingly. As shown in FIG. 7B, the processor can monitor 722 the received signals. The processor can identify 724 any changes in the received signals that may indicate an occurrence of either an onset or offset event. Additionally, the processor can determine 726 the time of day and compare the time of day against, for example, historical patient activity data or other similar settings information that may indicate whether the patient is typically active or inactive at that time of day. Based upon the determined time of day, and the patient's activity information, the processor can adjust 728 the event criteria used to determine an onset or offset event occurrence. For example, if the time of day indicates that the patient is generally in an inactive state, the processor can lower the reliance on or completely ignore the one or more motion signals when determining event occurrence. Conversely, if the determined time of day indicates that the patient is generally in an active state, the processor can rely on a combination of both one or more physiological signals and one or more motion signals when determining event occurrence.

As further shown in FIG. 7B, the processor can determine 730 if the changes are indicative of an event by, for example, comparing the changes in the received signals against one or more event criteria such as the adjusted event criteria determined above. If the processor determines 730 that the changes in the received signals are not indicative of an event, the processor can continue to search for and identify 724 changes in the received electrical signals. If, however, the processor does determine 730 that the changes in the received signals are indicative of an event, the processor can continue to monitor 732 the changes using, in some examples, the adjusted event criteria. The processor can determine 734 if the potential event is a confirmed event based upon the extended monitoring of the changes. If the processor does not determine 734 that the potential event is a confirmed event, the processor can continue to search for and identify 724 changes in the received signals. Conversely, if the processor does determine 734 that the potential event is a confirmed event, the processor can generate 736 confirmation of the event and record, for example, the event in a data structure such as Table 2 as described above. In certain implementations, the processor can be further configured to provide an indication in the data structure that the event was recorded using adjusted event criteria based upon the time of day of the event occurrence.

It should be noted that, in the above discussions of FIGS. 5-7B, onset and offset event detection and confirmation can be performed by monitoring one or more received electrical signals for a physiological signal such as an ECG signal. Based upon validity of the ECG signal, a processor as described herein can determine whether an onset or offset event has occurred. However, during normal operation of a wearable medical device as described herein, the processor can also be continuously monitoring the patient for a cardiac arrhythmia. In certain implementations, when a cardiac arrhythmia occurs, the processor may interpret the resulting ECG as being invalid. For example, when a patient is experiencing ventricular fibrillation (VF), the QRS complex timing as detected in the patient's ECG signal may be altered such that the ECG signal is considered invalid for determining wear compliance as described herein. In such an example, the processor can be programmed or otherwise adjusted to prioritize arrhythmia detection over onset and/or offset event detection and ignore or otherwise stop detecting onset and/or offset events until after the arrhythmia detection has stopped (e.g., if no arrhythmia was detected) or until after the patient has been treated and has returned to normal (or within an acceptable range of normal) cardiac activity.

Figure 8:
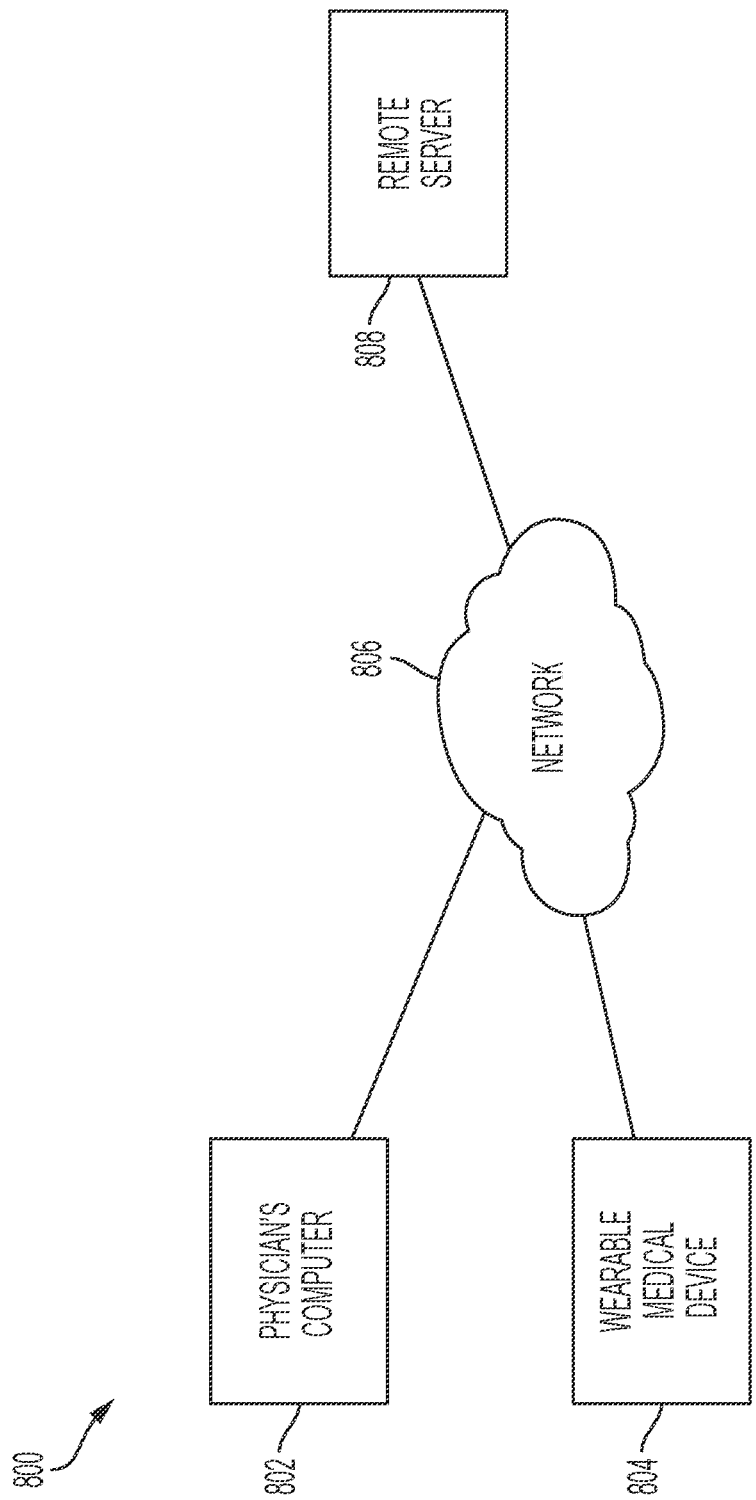
FIG. 8 illustrates a sample network overview, in accordance with an example of the present disclosure.

As described herein, a wearable medical device can be operably connected to one or more additional remotely located computing devices such as a remote server. For example, FIG. 8 illustrates a sample network 800 in which a wearable medical device (e.g., a medical device including medical device controller 300 as shown in FIG. 3) can be operably connected to a remote server. As described above in connection with FIG. 3, the wearable medical device controller 300 can include a network interface 306 for transmitting data over a wireless link such as a Bluetooth® wireless link (e.g., via a "hotspot" or other base station or intermediate device), a broadband cellular link, or a Wi-Fi™ communications link based on the IEEE 802.11 standard. As shown in FIG. 8, a physician's computer 802 and a wearable medical device 804 can be operably connected to a monitoring server 808 through network 806. In certain implementations, while being worn, the wearable medical device 804 can collect information related to the patient such as various patient metrics and parameters as described herein. For example, the wearable medical device 804 can collect physiological and ECG data related to the patient, RF-based measurement information, and wear compliance information for the period of time that the patient has been prescribed the wearable medical device. The wearable medical device 804 can also collect accelerometer data indicative of motion information associated with the patient such as number of steps taken during a time period such as 30 minutes, one hour, two hours, six hours, or one day, as well as duration information related to periods of activity such as how often and how long a patient exercises. Depending upon the connection to network 806, and the programming of wearable medical device 804, the wearable medical device can be configured to regularly transmit the collected information to the monitoring server 808 for storage and further processing and analysis. The network 806 may be a private, secure network configured to allow for intercommunication between authorized devices 804, computer 802, and server 808. For example, the private network may be implemented as a virtual private network (VPN) that can be formed using a plurality of encrypted communication techniques, including the creation of secure communication channels (called "tunnels") within a public network. As an example, a device 804 or computer 802 may implement a temporary or permanent dedicated communication software application to securely communicate with the server 808 via such a tunnel. The dedicated communication software application can encrypt and send and messages to the server 808 and receive and decrypt messages received from the server 808. Some types of such dedicated communication software applications can embed encrypted messages in formatted data packets, so that the encrypted messages are unreadable from outside of the secure communication channel.

When prescribing a wearable medical device as described herein, the prescribing physician or healthcare provider can be given one or more options to adjust various settings or parameters of the wear compliance monitoring process. For example, FIG. 9 illustrates a sample view of a user interface screen 900 that can be accessed and utilized by a physician and/or other HCP to modify one or more wear compliance monitoring settings for a particular patient. The physician can access an application such as a browser or gateway application executed by, for example, a processor integrated into the physician's computer 802 as described above to interact with the user interface screen 900.

As illustrated in FIG. 9, the user interface screen 900 includes user interface controls 902, 904, 906, 908, and 910. In some examples, the user interface screen 900 provides access to patient specific information such as the patient's name, an identifier associated with the patient, and information about the prescribed device such as a device identifier. In certain implementations, the patient identifier can be a medical records number associated with the patient, an insurance identification number associated with the patient, a number that directly identifies the patient such as a social security number, or another similar identification number. Based upon the patient specific information, the processor can access the patient's medical record. Based upon information contained in the medical record such as patient condition information, historical patient information, demographic information, and rehabilitation baselining information, the processor can generate a set of default wear compliance monitoring parameters without additional information from the physician.

In some examples, the processor can present the physician with the option to customize the wear compliance monitoring parameters. For example, the user interface control 902 can provide access to specific information related to minimum wear compliance monitoring parameters. The user interface controls 902 can include one or more additional controls 903 that can include one or more user-interactive or selectable inputs for receiving additional information related to the minimum wear compliance monitoring parameters. For example, additional controls 903 can include a total wear time field, a number of approved removal periods, and a maximum removal time allowed per removal period. For example, as shown in FIG. 9, additional controls 903 include a combination of text fields and a drop-down menu. However, the specific implementations of additional controls 903 is shown by way of example only. In this example, the additional controls 903 have received a physician input of 23 hours per day of total wear, 2 allowed removal periods, and a maximum time of 30 minutes per removal period. Specific inputs and the sample numbers included in additional controls 903 are provided by way of example only.

As noted above, user interface screen 900 can further include user interface control 904. The user interface control 904 can provide access to specific information related to target wear compliance monitoring parameters. For example, the target wear compliance monitoring parameters can include goals set by the physician for the patient to achieve during the time the wearable medical device is prescribed to the patient. The user interface controls 904 can include one or more additional controls 905 that can include one or more user-interactive or selectable inputs for receiving additional information related to the target wear compliance monitoring parameters. For example, additional controls 905 can include a total wear time field, a number of approved removal periods, and a maximum removal time allowed per removal period. For example, as shown in FIG. 9, additional controls 905 include a combination of text fields and a drop-down menu. However, the specific implementations of additional controls 905 is shown by way of example only. In this example, the additional controls 905 have received a physician input of 23.5 hours per day of total wear, one allowed removal periods, and a maximum time of 30 minutes per removal period. However, it should be noted that specific inputs and the sample numbers included in additional controls 905 are provided by way of example only.

As noted above, user interface screen 900 can further include user interface control 906. The user interface control 906 can provide access to specific information related to onset and offset event detection criteria as described herein. The user interface controls 906 can include one or more additional controls 907. In some examples, the one or more additional controls 907 can include one or more user-interactive or selectable inputs for receiving additional information related to the onset and offset event detection criteria. For example, additional controls 907 can include a user-selectable input for using default criteria or a user-selectable input for using custom criteria.

As noted above, user interface screen 900 can further include user interface control 908. The user interface control 908 can provide access to specific information related to alert criteria for alerting one or more people such as the physician, another HCP, the patient, and other similar people about the patient's wear compliance information. The user interface controls 908 can include one or more additional controls 909. In some examples, the one or more additional controls 909 can include one or more user-interactive or selectable inputs for indicating what criteria should be met before an alert is generated. For example, the additional controls 909 include a set of user-selectable inputs for receiving an alert each day that the minimum compliance information is not met, receiving an alert after a set number of consecutive days have passed that the minimum compliance information has not been met, receiving an alert each day that the target compliance information is not met, receiving an alert after a set number of consecutive days have passed that the target compliance information is not met, and receiving an alert after a set number of consecutive days have passed that the target compliance information has been met. Certain inputs in additional controls 909 include a combination of user-selectable input as well as a customizable field that the physician can use to provide additional information such as a number of days as shown in FIG. 9. However, the number, arrangement, and labels of the additional controls 909 as shown in FIG. 9 is by way of example only.

As further shown in FIG. 9, the user interface control 910 includes a set of selectable buttons. In response to receiving a selection of the "submit" button, the processor can update a set of wear compliance parameters for the patient. In response to receiving a selection of the "clear" button, the processor can delete existing selections and/or entered information from the user interface screen 900. In response to receiving a selection of the "cancel" button, the processor can abort updating the wear compliance parameters as described above.

As described herein, wear compliance information as generated by a wearable medical device can be transmitted to a remote server for additional processing and access by, for example, the patient's physician for review. Additionally, the wear compliance information can be presented to the patient on a user interface integrated into the wearable medical device (e.g., user interface 308 as shown in FIG. 3 and described herein) or via a personal computing device assigned to or otherwise accessed by the patient such as a smartphone.

Figure 10A:
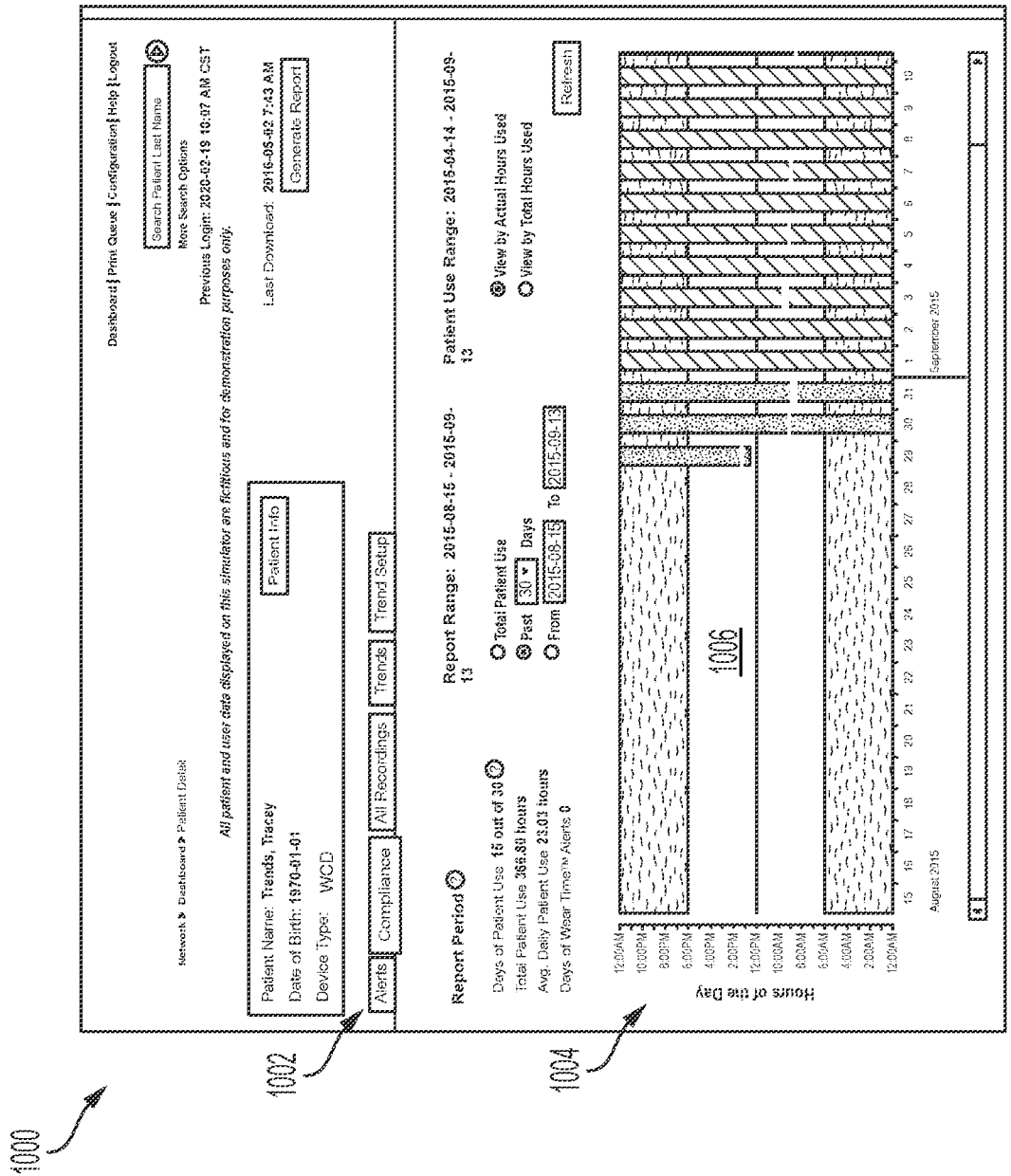
FIGS. 10A-10F illustrate sample views of a user interface including graphical feedback related to a patient's wear compliance information, in accordance with an example of the present disclosure.
Figure 10B:
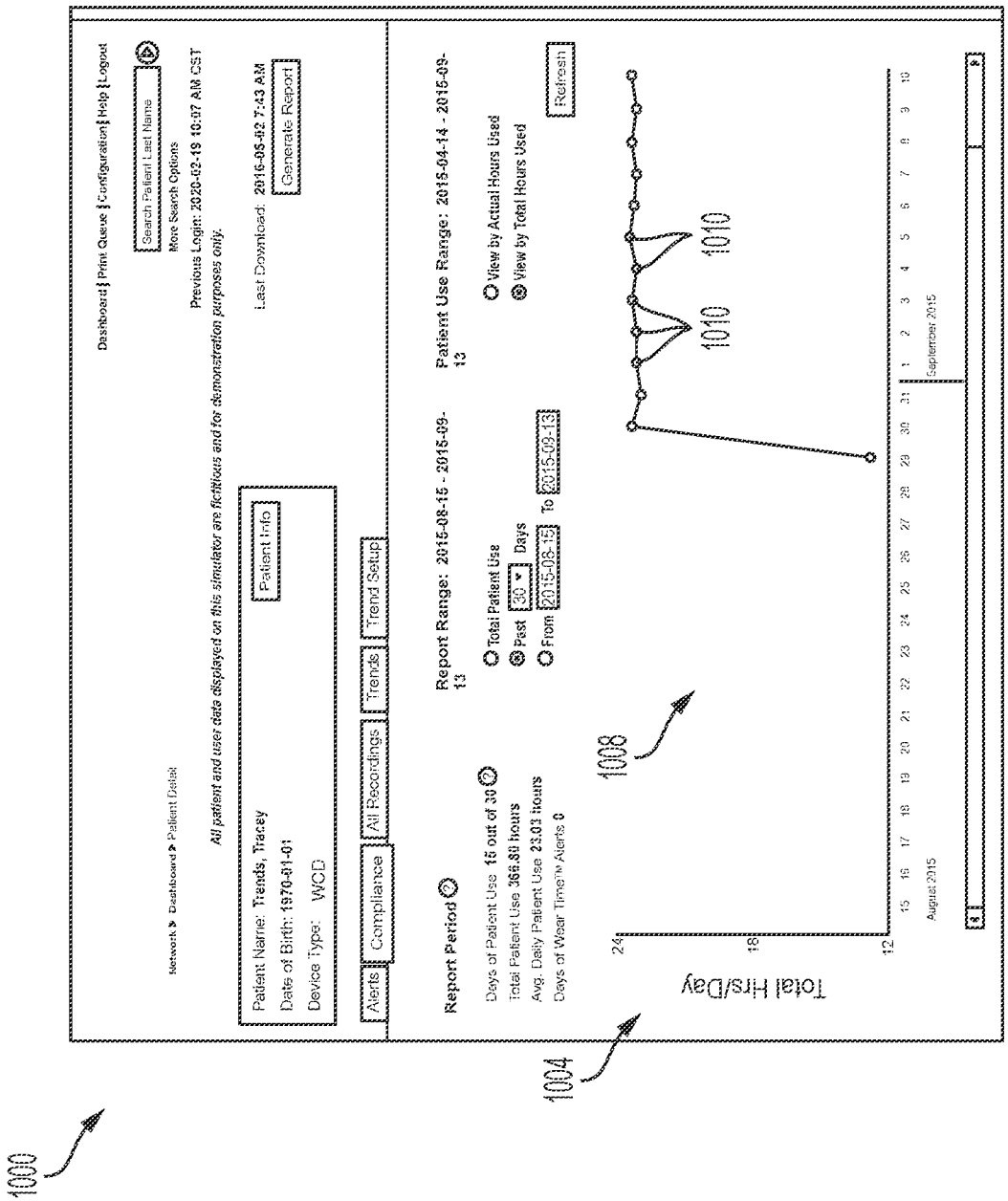
Figure 10C:
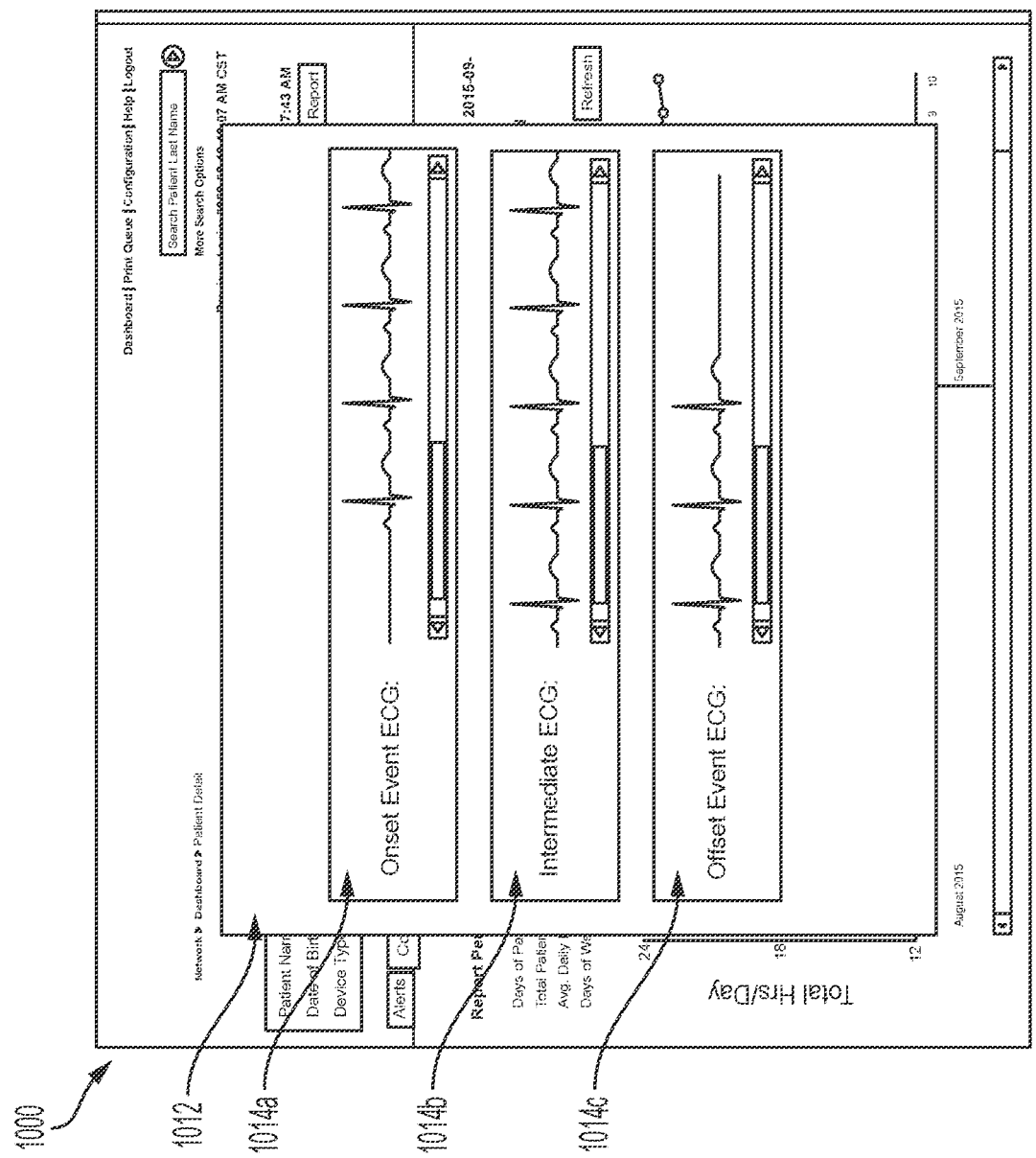

In certain implementations, the wear compliance information can be presented to caregivers via a network-based portal such as a physician's web portal. For example, the portal can be accessed on a variety of electronic devices such as a portable computing device assigned to or otherwise accessed by a physician or a computer such as physician's computer 802 as shown in FIG. 8 and described herein. It is desirable to provide pertinent information regarding a patient's wear compliance to the physician in an easy to understand format. Further, as noted above, a physician may wish to set alerts regarding a patient's deviation from minimum or target wear compliance guidelines. FIGS. 10A-10C describe one or more interfaces for delivering wear compliance information to a physician including, for example, a summary screen (or portion of a screen) with presentation of key compliance data for a quick glance, and a more detailed screen (or portion of a screen) with very detailed information underlying the key compliance data presented on the summary screen.

For example, FIG. 10A illustrates sample user interface screen 1000 that includes a sample set of fictitious patient data for demonstration purposes only. The user interface screen 1000 can include a set of data such as patient information, login information, and other similar overall data. The user interface screen 1000 can further include a set of tabs 1002 that include more specific summary information for the patient. As shown in FIG. 10A, a compliance tab has been selected and a set of summary wear compliance data is presented. For example, the summary wear compliance information includes report period information, report range information, and patient use range information. As shown in FIG. 10A, the report period information includes information about days of patient use, total patient use information, average daily patient use information, and days of alerts. Similarly, as shown in FIG. 10A, the report range information includes user-selectable inputs for adjusting the total period of time illustrated in the user interface screen 1000. The patient use range includes user-selectable inputs for adjusting how additional, detailed information is presented in user interface screen 1000.

As further shown in FIG. 10A, the user interface screen 1000 can include a detailed portion 1004 that includes more specific wear compliance information for the patient. The user-selectable input for patient use range has been set to view by actual hours used. In light of this user-selection, the data included in detailed portion 1004 is formatted based upon total hours used per day as organized in a bar graph 1006 where hours of the day is provided on the y-axis and the date is provided on the x-axis. As shown in FIG. 10A, the bar graph 1006 can further include an indication of patient wear compliance as compared to patient wear non-compliance.

It should be noted that providing the information in the detailed portion 1004 is shown as bar graph 1006 in FIG. 10A by way of example only. Upon receiving an indication that the user-selectable input for patient use range has been changed, a processor generating the user interface screen 1000 can update the detailed portion 1004 accordingly. For example, as shown in FIG. 10B, the user-selectable input for patient use range has been changed to "View by Total Hours Used," the detailed portion 1004 can be updated to include a line graph 1008. As shown in FIG. 10B, line graph 1008 includes total hours worn per day on the y-axis and date on the x-axis. As such, line graph 1008 provides a quick view of the total number of hours the patient wore the medical device each day as well as any trends in total wear compliance for the patient such as recorded changes in wear compliance for the patient.

In some examples, a graphical representation such as bar graph 1006 and line graph 1008 can include a view of wear compliance information covering an entire period that the patient has been prescribed the wearable medical device. For example, the patient can be prescribed the device for 90 days. At the end of the 90 day prescription period, the physician can view the wear compliance information for the entire period in a single graphical representation. In some examples, the prescription period can be altered. For example, the prescription period can be seven days, 14 days, 30 days, 60 days, 180 days, one year, and other similar periods. In certain implementations, the physician can modify the graphical representation to view a portion of the wear compliance information. For example, if the prescription period is 90 days, the physician can modify one or both of bar graph 1006 and line graph 1008 to show a portion of the period such as five days, one week, two weeks, or 30 days.

In certain implementations, the user interface screen can further include one or more user-selectable interface controls configured to provide access to recorded ECG information for one or more of an onset event, an offset event, and a period of time when the patient was wearing the wearable medical device. For example, each of bar graph 1006 and line graph 1008 can include one or more user-selectable interface controls for accessing the recorded ECG information. For example, as shown in FIG. 10B, the line graph 1008 can include one or more user-selectable interface controls 1010 embedded into the graphical representation of the wear compliance information. Upon receiving selection of one of the controls 1010, the user interface screen can updated to include additional information such as recorded ECG information. For example, as shown in FIG. 10C, window 1012 can be overlaid on user interface screen 1000 including additional information related to a selected control 1010. For example, the window 1012 can include ECG recording information 1014a recorded during an initial onset event, intermediate ECG recording information 1014b recorded between the onset and an offset event, and ECG recording information 1014c recorded at the offset event. The recorded ECG information shown in FIG. 10C is included by way of example only and, in some implementations, additional information such as information derived from one or more motion signals as described herein, impedance information, ECG metric information, time of day information, and other similarly recorded information can be displayed or otherwise provided in user interface screen 1000.

Figure 10D:
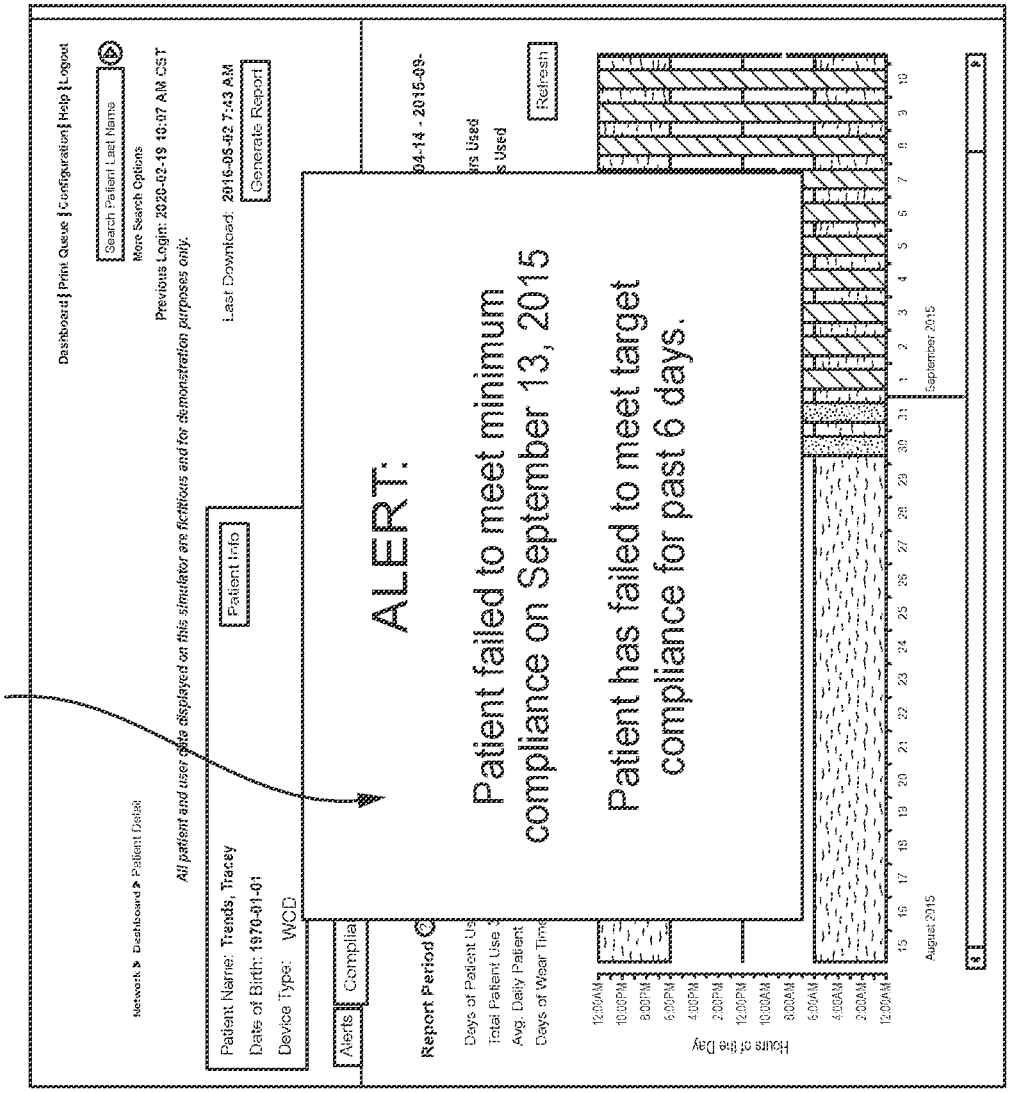

As described above in the discussion of FIG. 9, the physician can set one or more alert criteria for receiving an alert about patient wear compliance information. As shown in FIG. 10D, the user interface screen 1000 can also display an overlaid alert 1016 indicating one or more alerts about the patient's wear compliance information. For example, as shown in FIG. 10D, the alert 1016 indicates that the patient failed to meet the minimum compliance information on Sep. 13, 2015 and has failed to meet the target compliance information for the past six days. It should be noted that the overall alert including location on screen 1000 and information included herein as shown in FIG. 10D is provided by way of example only. Depending upon the physician settings, the information contained in the alert can vary accordingly.

In addition to providing wear compliance information to a caregiver such as a physician, it can be desirable to provide wear compliance information to the patient themselves. By providing the patient with instant, immediate, or readily available feedback on the patient's wear compliance, non-compliance can be recognized immediately by the patient, thereby providing the patient with the opportunity to correct compliance deficiencies without physician intervention. Additionally, positive feedback can provide the patient with added motivation to continue to excel in their wear compliance.

Figures 10E, 10F:
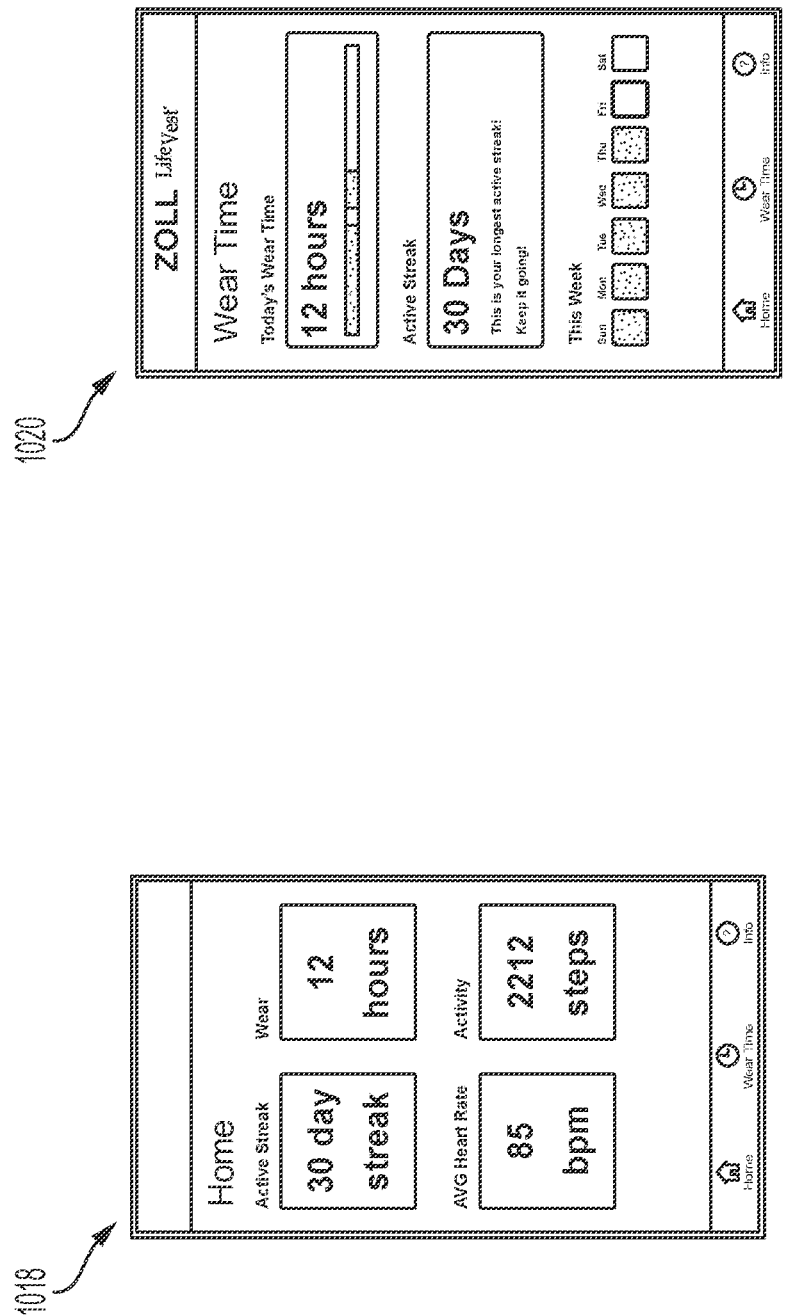

FIGS. 10E and 10F illustrate sample feedback that can be provided to the patient regarding the patient's wear compliance information. The feedback can be transmitted to a personal computing device such as the patient's smartphone for processing and display. For example, a processor integrated into the personal computing device can process and cause the feedback information to be displayed on a display of the personal computing device. For example, as shown in FIG. 10E, the device can display user interface screen 1018. User interface screen 1018 can include a high-level overview of the patient's information. For example, as shown in FIG. 10E, the user interface screen 1018 can include wear compliance streak information, today's wear information, average daily heart rate information, and activity information for the patient.

In certain implementations, the device can further provide additional information related to wear compliance. For example, as shown in FIG. 10F, the device can display user interface screen 1020 that includes additional and more specific wear compliance information for the patient. For example, the user interface screen 1020 can include a graph of today's wear time, including a highlighted portion of time where the device has been worn and time when the device was not worn. The user interface screen 1020 can further include active streak information such as total number of days in a row that the patient has been compliant with the wear requirements as well as historical information about how the current streak compares to past wear compliance streaks. The user interface screen 1020 can also include information such as wear compliance information for the current week.

Wear compliance information shown in FIGS. 10E and 10F is provided by way of example only. In certain implementations, the type of information provided to the patient can vary based upon, for example, input from the patient's physician, type of wearable medical device prescribed to the patient, expected compliance criteria for the patient, and other similar parameters.

It should also be noted that providing wear compliance information in a graphical representation accessible via, for example, a web portal as described above, is provided by way of example only. In certain implementations, providing wear compliance information (e.g., outputting 514 wear compliance information as shown in FIG. 5 and described above) can also include generating a report that can be sent electronically to one or more recipients such as the patient's physician. The report can include various data as described herein that has been filtered based upon set criteria by, for example, the patient's physician. The report can be organized daily, weekly, monthly, or according to other similar periods of time and include wear compliance information for the patient over those periods of time. The report can also include charts and/or graphs similar to those as shown in FIGS. 10A and 10B and described above.

The teachings of the present disclosure can be generally applied to external medical monitoring and/or treatment devices that include one or more sensors as described herein. Such external medical devices can include, for example, ambulatory medical devices as described herein that are capable of and designed for moving with the patient as the patient goes about his or her daily routine. An example ambulatory medical device can be a wearable medical device such as a WCD, a wearable cardiac monitoring device, an in-hospital device such as an in-hospital wearable defibrillator (HWD), a short-term wearable cardiac monitoring and/or therapeutic device, mobile cardiac event monitoring devices, and other similar wearable medical devices.

The wearable medical device can be capable of continuous use by the patient. In some implementations, the continuous use can be substantially or nearly continuous in nature. That is, the wearable medical device can be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless be considered continuous use. For example, the wearable medical device can be configured to be worn by a patient for as many as 24 hours a day. In some implementations, the patient can remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other HCP provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, cardio-vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other non-ECG physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the ambulatory medical devices described herein can be pacing-enabled, e.g., capable of providing therapeutic pacing pulses to the patient. In some examples, the ambulatory medical devices can be configured to monitor for and/or measure ECG metrics including, for example, heart rate (such as average, median, mode, or other statistical measure of the heart rate, and/or maximum, minimum, resting, pre-exercise, and post-exercise heart rate values and/or ranges), heart rate variability metrics, PVC burden or counts, atrial fibrillation burden metrics, pauses, heart rate turbulence, QRS height, QRS width, changes in a size or shape of morphology of the ECG information, cosine R-T, artificial pacing, QT interval, QT variability, T wave width, T wave alternans, T-wave variability, and ST segment changes.

As noted above, FIG. 3 illustrates an example component-level view of a medical device controller 300 included in, for example, a wearable medical device. As further shown in FIG. 3, the therapy delivery circuitry 302 can be coupled to one or more electrodes 320 configured to provide therapy to the patient. For example, the therapy delivery circuitry 302 can include, or be operably connected to, circuitry components that are configured to generate and provide an electrical therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuitry and under control of one or more processors (e.g., processor 318) to provide, for example, at least one therapeutic shock to the patient including one or more pacing, cardioversion, or defibrillation therapeutic pulses.

Pacing pulses can be used to treat cardiac arrhythmia conditions such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). In some examples, the capacitors can include a single film or electrolytic capacitor as a series connected device including a bank of the same capacitors. These capacitors can be switched into a series connection during discharge for a defibrillation pulse. For example, a single capacitor of approximately 140 uF or larger, or four capacitors of approximately 650 uF can be used. The capacitors can have a 1600 VDC or higher rating for a single capacitor, or a surge rating between approximately 350 to 500 VDC for paralleled capacitors and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuitry 302 can be configured to perform the switching and pulse delivery operations, e.g., under control of the processor 318. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

In certain examples, the therapy delivery circuitry 302 can be configured to deliver a set of cardioversion pulses to correct, for example, an improperly beating heart. When compared to defibrillation as described above, cardioversion typically includes a less powerful shock that is delivered at a certain frequency to mimic a heart's normal rhythm.

The data storage 304 can include one or more of non-transitory computer-readable media, such as flash memory, solid state memory, magnetic memory, optical memory, cache memory, combinations thereof, and others. The data storage 304 can be configured to store executable instructions and data used for operation of the medical device controller 300. In certain examples, the data storage can include executable instructions that, when executed, are configured to cause the processor 318 to perform one or more operations. In some examples, the data storage 304 can be configured to store information such as ECG data as received from, for example, the sensing electrode interface.

In some examples, the network interface 306 can facilitate the communication of information between the medical device controller 300 and one or more other devices or entities over a communications network such as network 806 as shown in FIG. 8. For example, where the medical device controller 300 is included in an ambulatory medical device, the network interface 306 can be configured to communicate with a remote computing device such as a remote server (e.g., remote server 808 as shown in FIG. 8) or other similar computing device. The network interface 306 can include communications circuitry for transmitting data in accordance with a Bluetooth® wireless standard for exchanging such data over short distances to an intermediary device. For example, such an intermediary device can be configured as a base station, a "hotspot" device, a smartphone, a tablet, a portable computing device, and/or other devices in proximity of the wearable medical device including the medical device controller 300. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain examples, the user interface 308 can include one or more physical interface devices such as input devices, output devices, and combination input/output devices and a software stack configured to drive operation of the devices. These user interface elements can render visual, audio, and/or tactile content. Thus, the user interface 308 can receive input or provide output, thereby enabling a user to interact with the medical device controller 300. In certain implementations, the user interface 308 can be configured to provide user interface screen 1000 as shown in FIG. 10D and user interface screen 1018 as shown in FIG. 10E to the user of the medical device controller 300.

The medical device controller 300 can also include at least one rechargeable battery 310 configured to provide power to one or more components integrated in the medical device controller 300. The rechargeable battery 310 can include a rechargeable multi-cell battery pack. In one example implementation, the rechargeable battery 310 can include three or more 2200 mAh lithium ion cells that provide electrical power to the other device components within the medical device controller 300. For example, the rechargeable battery 310 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 300.

The sensor interface 312 can include physiological signal circuitry that is coupled to one or more sensors configured to monitor one or more physiological parameters of the patient. As shown, the sensors can be coupled to the medical device controller 300 via a wired or wireless connection. The sensors can include one or more ECG sensing electrodes 322, and non-ECG physiological sensors 323 such as vibration sensor 324, tissue fluid monitors 326 (e.g., based on ultra-wide band RF devices), and motion sensors (e.g., accelerometers, gyroscopes, and/or magnetometers). In some implementations, the sensors can include a plurality of conventional ECG sensing electrodes in addition to digital sensing electrodes.

The sensing electrodes 322 can be configured to monitor a patient's ECG information. For example, by design, the digital sensing electrodes 322 can include skin-contacting electrode surfaces that may be deemed polarizable or non-polarizable depending on a variety of factors including the metals and/or coatings used in constructing the electrode surface. All such electrodes can be used with the principles, techniques, devices and systems described herein. For example, the electrode surfaces can be based on stainless steel, noble metals such as platinum, or Ag—AgCl.

In some examples, the electrodes 322 can be used with an electrolytic gel dispersed between the electrode surface and the patient's skin. In certain implementations, the electrodes 322 can be dry electrodes that do not need an electrolytic material. As an example, such a dry electrode can be based on tantalum metal and having a tantalum pentoxide coating as is described above. Such dry electrodes can be more comfortable for long term monitoring applications.

Referring back to FIG. 3, the vibration sensors 324 can be configured to detect cardiac or pulmonary vibration information. For example, the vibration sensors 324 can detect a patient's heart valve vibration information. For example, the vibration sensors 324 can be configured to detect cardio-vibrational signal values including any one or all of S1, S2, S3, and S4. From these cardio-vibrational signal values or heart vibration values, certain heart vibration metrics may be calculated, including any one or more of electromechanical activation time (EMAT), average EMAT, percentage of EMAT (% EMAT), systolic dysfunction index (SDI), and left ventricular systolic time (LVST). The vibration sensors 324 can also be configured to detect heart wall motion, for instance, by placement of the sensor in the region of the apical beat. The vibration sensors 324 can include a vibrational sensor configured to detect vibrations from a patient's cardiac and pulmonary system and provide an output signal responsive to the detected vibrations of a targeted organ, for example, being able to detect vibrations generated in the trachea or lungs due to the flow of air during breathing. In certain implementations, additional physiological information can be determined from pulmonary-vibrational signals such as, for example, lung vibration characteristics based on sounds produced within the lungs (e.g., stridor, crackle, etc.). The vibration sensors 324 can also include a multi-channel accelerometer, for example, a three-channel accelerometer configured to sense movement in each of three orthogonal axes such that patient movement/body position can be detected and correlated to detected cardio-vibrations information. The vibration sensors 324 can transmit information descriptive of the cardio-vibrations information to the sensor interface 312 for subsequent analysis.

The tissue fluid monitors 326 can use RF based techniques to assess fluid levels and accumulation in a patient's body tissue. For example, the tissue fluid monitors 326 can be configured to measure fluid content in the lungs, typically for diagnosis and follow-up of pulmonary edema or lung congestion in heart failure patients. The tissue fluid monitors 326 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 326 can transmit information descriptive of the tissue fluid levels to the sensor interface 312 for subsequent analysis.

In certain implementations, the cardiac event detector 316 can be configured to monitor a patient's ECG signal for an occurrence of a cardiac event such as an arrhythmia or other similar cardiac event. The cardiac event detector can be configured to operate in concert with the processor 318 to execute one or more methods that process received ECG signals from, for example, the sensing electrodes 322 and determine the likelihood that a patient is experiencing a cardiac event. The cardiac event detector 316 can be implemented using hardware or a combination of hardware and software. For instance, in some examples, cardiac event detector 316 can be implemented as a software component that is stored within the data storage 304 and executed by the processor 318. In this example, the instructions included in the cardiac event detector 316 can cause the processor 318 to perform one or more methods for analyzing a received ECG signal to determine whether an adverse cardiac event is occurring. In other examples, the cardiac event detector 316 can be an application-specific integrated circuit (ASIC) that is coupled to the processor 318 and configured to monitor ECG signals for adverse cardiac event occurrences. Thus, examples of the cardiac event detector 316 are not limited to a particular hardware or software implementation.

In some implementations, the processor 318 includes one or more processors (or one or more processor cores) that each are configured to perform a series of instructions that result in manipulated data and/or control the operation of the other components of the medical device controller 300. In some implementations, when executing a specific process (e.g., cardiac monitoring), the processor 318 can be configured to make specific logic-based determinations based on input data received and be further configured to provide one or more outputs that can be used to control or otherwise inform subsequent processing to be carried out by the processor 318 and/or other processors or circuitry with which processor 318 is communicatively coupled. Thus, the processor 318 reacts to specific input stimulus in a specific way and generates a corresponding output based on that input stimulus. In some example cases, the processor 318 can proceed through a sequence of logical transitions in which various internal register states and/or other bit cell states internal or external to the processor 318 can be set to logic high or logic low. As referred to herein, the processor 318 can be configured to execute a function where software is stored in a data store coupled to the processor 318, the software being configured to cause the processor 118 to proceed through a sequence of various logic decisions that result in the function being executed. The various components that are described herein as being executable by the processor 318 can be implemented in various forms of specialized hardware, software, or a combination thereof. For example, the processor 318 can be a digital signal processor (DSP) such as a 24-bit DSP. The processor 318 can be a multi-core processor, e.g., having two or more processing cores. The processor 318 can be an Advanced RISC Machine (ARM) processor such as a 32-bit ARM processor or a 64-bit ARM processor. The processor 318 can execute an embedded operating system, and include services provided by the operating system that can be used for file system manipulation, display & audio generation, basic networking, firewalling, data encryption and communications.

As noted above, an ambulatory medical device such as a WCD can be designed to include a digital front-end where analog signals sensed by skin-contacting electrode surfaces of a set of digital sensing electrodes are converted to digital signals for processing. Typical ambulatory medical devices with analog front-end configurations use circuitry to accommodate a signal from a high source impedance from the sensing electrode (e.g., having an internal impedance range from approximately 100 Kiloohms to one or more Megaohms). This high source impedance signal is processed and transmitted to a monitoring device such as processor 318 of the controller 300 as described above for further processing. In certain implementations, the monitoring device, or another similar processor such as a microprocessor or another dedicated processor operably coupled to the sensing electrodes, can be configured to receive a common noise signal from each of the sensing electrodes, sum the common noise signals, invert the summed common noise signals and feed the inverted signal back into the patient as a driven ground using, for example, a driven right leg circuit to cancel out common mode signals.

Figure 11A:
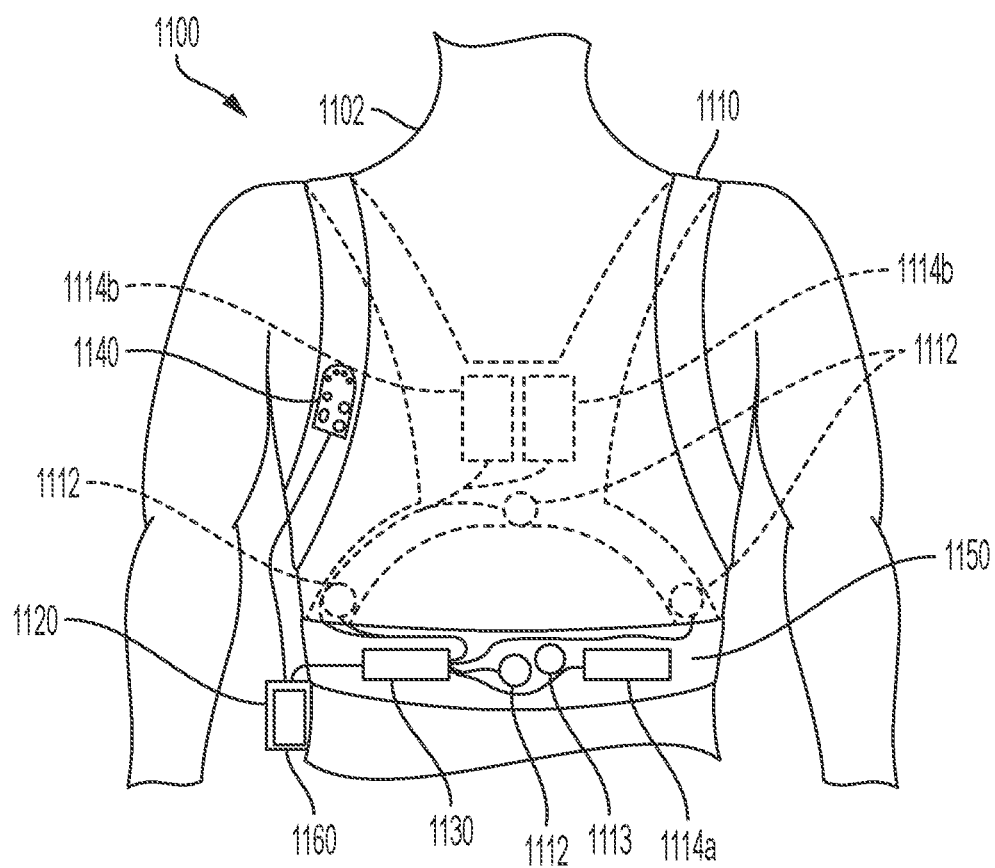

FIG. 11A illustrates an example medical device 1100 that is external, ambulatory, and wearable by a patient 1102, and configured to implement one or more configurations described herein. For example, the medical device 1100 can be a non-invasive medical device configured to be located substantially external to the patient. Such a medical device 1100 can be, for example, an ambulatory medical device that is capable of and designed for moving with the patient as the patient goes about his or her daily routine. For example, the medical device 1100 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 1100 can include one or more of the following: a garment 1110, one or more ECG sensing electrodes 1112, one or more non-ECG physiological sensors 1113, one or more therapy electrodes 1114a and 1114b (collectively referred to herein as therapy electrodes 1114), a medical device controller 1120 (e.g., controller 300 as described above in the discussion of FIG. 3), a connection pod 1130, a patient interface pod 1140, a belt 1150, or any combination of these. In some examples, at least some of the components of the medical device 1100 can be configured to be affixed to the garment 1110 (or in some examples, permanently integrated into the garment 1110), which can be worn about the patient's torso.

The medical device controller 1120 can be operatively coupled to the sensing electrodes 1112, which can be affixed to the garment 1110, e.g., assembled into the garment 1110 or removably attached to the garment, e.g., using hook and loop fasteners. In some implementations, the sensing electrodes 1112 can be permanently integrated into the garment 1110. The medical device controller 1120 can be operatively coupled to the therapy electrodes 1114. For example, the therapy electrodes 1114 can also be assembled into the garment 1110, or, in some implementations, the therapy electrodes 1114 can be permanently integrated into the garment 1110. In an example, the medical device controller 1120 includes a patient user interface 1160 to allow a patient interface with the externally-worn device. For example, the patient can use the patient user interface 1160 to respond to activity related questions, prompts, and surveys as described herein.

Component configurations other than those shown in FIG. 11A are possible. For example, the sensing electrodes 1112 can be configured to be attached at various positions about the body of the patient 1102. The sensing electrodes 1112 can be operatively coupled to the medical device controller 1120 through the connection pod 1130. In some implementations, the sensing electrodes 1112 can be adhesively attached to the patient 1102. In some implementations, the sensing electrodes 1112 and at least one of the therapy electrodes 1114 can be included on a single integrated patch and adhesively applied to the patient's body.

The sensing electrodes 1112 can be configured to detect one or more cardiac signals. Examples of such signals include ECG signals and/or other sensed cardiac physiological signals from the patient. In certain examples, as described herein, the non-ECG physiological sensors 1113 comprise components such as accelerometers, vibrational sensors, RF-based sensors, and other measuring devices for recording additional non-ECG physiological parameters. For example, as described above, the such non-ECG physiological sensors are configured to detect other types of patient physiological parameters and acoustic signals, such as tissue fluid levels, cardio-vibrations, lung vibrations, respiration vibrations, patient movement, etc.

In some examples, the therapy electrodes 1114 can also be configured to include sensors configured to detect ECG signals as well as other physiological signals of the patient. The connection pod 1130 can, in some examples, include a signal processor configured to amplify, filter, and digitize these cardiac signals prior to transmitting the cardiac signals to the medical device controller 1120. One or more of the therapy electrodes 1114 can be configured to deliver one or more therapeutic defibrillating shocks to the body of the patient 1102 when the medical device 1100 determines that such treatment is warranted based on the signals detected by the sensing electrodes 1112 and processed by the medical device controller 1120. Example therapy electrodes 1114 can include metal electrodes such as stainless-steel electrodes that include one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 1114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device to convert the therapeutic medical device into a monitoring medical device for a specific use (e.g., for operating in a monitoring-only mode) or a patient. Alternatively, the optional therapeutic elements can be deactivated (e.g., via a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 11B:
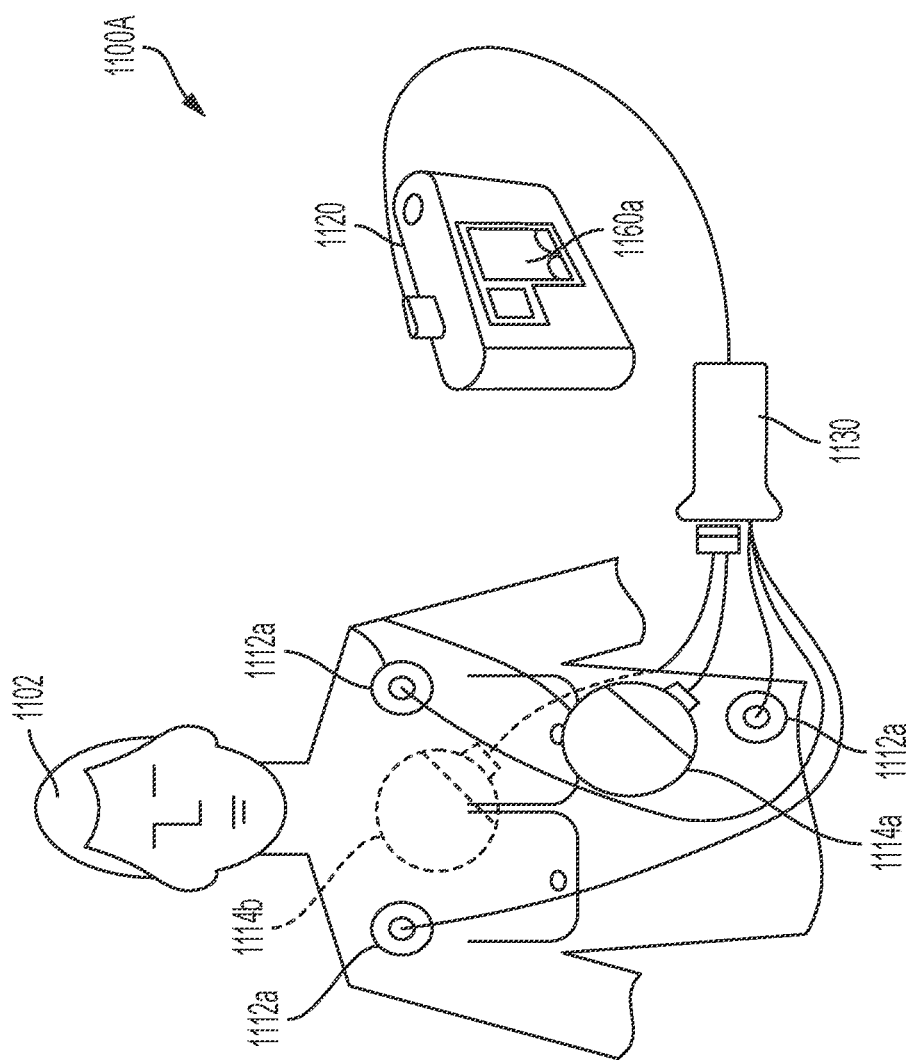

FIG. 11B illustrates a hospital wearable defibrillator 1100A that is external, ambulatory, and wearable by a patient 1102. Hospital wearable defibrillator 1100A can be configured in some implementations to provide pacing therapy, e.g., to treat bradycardia, tachycardia, and asystole conditions. The hospital wearable defibrillator 1100A can include one or more ECG sensing electrodes 1112a, one or more therapy electrodes 1114a and 1114b, a medical device controller 1120 and a connection pod 1130. For example, each of these components can be structured and function as like number components of the medical device 1100. For example, the electrodes 1112a, 1114a, 1114b can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. For example, the front adhesively attachable therapy electrode 1114a attaches to the front of the patient's torso to deliver pacing or defibrillating therapy. Similarly, the back adhesively attachable therapy electrode 1114b attaches to the back of the patient's torso. In an example scenario, at least three ECG adhesively attachable sensing electrodes 1112a can be attached to at least above the patient's chest near the right arm, above the patient's chest near the left arm, and towards the bottom of the patient's chest in a manner prescribed by a trained professional.

A patient being monitored by a hospital wearable defibrillator and/or pacing device may be confined to a hospital bed or room for a significant amount of time (e.g., 75% or more of the patient's stay in the hospital). As a result, a user interface 1160a can be configured to interact with a user other than the patient, e.g., a nurse, for device-related functions such as initial device baselining, setting and adjusting patient parameters, and changing the device batteries.

In some examples, the hospital wearable defibrillator 1100A can further include one or more motion sensors such as accelerometers. For example, an accelerometer can be integrated into one or more of a sensing electrode 1112a (e.g., integrated into the same patch as the sensing electrode), a therapy electrode 1114a (e.g., integrated into the same patch as the therapy electrode), the medical device controller 1120, the connection pod 1130, and various other components of the hospital wearable defibrillator 1100A.

In some implementations, an example of a therapeutic medical device that includes a digital front-end in accordance with the systems and methods described herein can include a short-term defibrillator and/or pacing device. For example, such a short-term device can be prescribed by a physician for patients presenting with syncope. A wearable defibrillator can be configured to monitor patients presenting with syncope by, e.g., analyzing the patient's physiological and cardiac activity for aberrant patterns that can indicate abnormal physiological function. For example, such aberrant patterns can occur prior to, during, or after the onset of syncope. In such an example implementation of the short-term wearable defibrillator, the electrode assembly can be adhesively attached to the patient's skin and have a similar configuration as the hospital wearable defibrillator described above in connection with FIG. 11A.

FIGS. 11C and 11D illustrate example wearable patient monitoring devices with no treatment or therapy functions. For example, such devices are configured to monitor one or more physiological parameters of a patient, e.g., for remotely monitoring and/or diagnosing a condition of the patient. For example, such physiological parameters can include a patient's ECG information, tissue (e.g., lung) fluid levels, cardio-vibrations (e.g., using accelerometers or microphones), and other related cardiac information. A cardiac monitoring device is a portable device that the patient can carry around as he or she goes about their daily routine.

Referring to FIG. 11C, an example wearable patient monitoring device 1100C can include tissue fluid monitors 1165 that use RF based techniques to assess fluid levels and accumulation in a patient's body tissue. Such tissue fluid monitors 1165 can be configured to measure fluid content in the lungs, typically for diagnosis and follow-up of pulmonary edema or lung congestion in heart failure patients. The tissue fluid monitors 1165 can include one or more antennas configured to direct RF waves through a patient's tissue and measure output RF signals in response to the waves that have passed through the tissue. In certain implementations, the output RF signals include parameters indicative of a fluid level in the patient's tissue. In examples, device 1100C may be a cardiac monitoring device that also includes digital sensing electrodes 1170 for sensing ECG activity of the patient. Device 1100C can pre-process the ECG signals via one or more ECG processing and/or conditioning circuits such as an ADC, operational amplifiers, digital filters, signal amplifiers under control of a microprocessor. Device 1100C can transmit information descriptive of the ECG activity and/or tissue fluid levels via a network interface to a remote server for analysis. Additionally, in certain implementations, the device 1100C can include one or accelerometers for measuring motion signals as described herein.

Referring to FIG. 11D, another example wearable cardiac monitoring device 1100D can be attached to a patient via at least three adhesive digital cardiac sensing electrodes 1175 disposed about the patient's torso. Additionally, in certain implementations, the device 1100D can include one or accelerometers integrated into, for example, one or more of the digital sensing electrodes for measuring motion signals as described herein.

Cardiac devices 1100C and 1100D are used in cardiac monitoring and telemetry and/or continuous cardiac event monitoring applications, e.g., in patient populations reporting irregular cardiac symptoms and/or conditions. These devices can transmit information descriptive of the ECG activity and/or tissue fluid levels via a network interface to a remote server for analysis. Example cardiac conditions that can be monitored include atrial fibrillation (AF), bradycardia, tachycardia, atrio-ventricular block, Lown-Ganong-Levine syndrome, atrial flutter, sino-atrial node dysfunction, cerebral ischemia, pause(s), and/or heart palpitations. For example, such patients may be prescribed a cardiac monitoring for an extended period of time, e.g., 10 to 30 days, or more. In some ambulatory cardiac monitoring and/or telemetry applications, a portable cardiac monitoring device can be configured to substantially continuously monitor the patient for a cardiac anomaly, and when such an anomaly is detected, the monitor can automatically send data relating to the anomaly to a remote server. The remote server may be located within a 24-hour manned monitoring center, where the data is interpreted by qualified, cardiac-trained reviewers and/or HCPs, and feedback provided to the patient and/or a designated HCP via detailed periodic or event-triggered reports. In certain cardiac event monitoring applications, the cardiac monitoring device is configured to allow the patient to manually press a button on the cardiac monitoring device to report a symptom. For example, a patient can report symptoms such as a skipped beat, shortness of breath, light headedness, racing heart rate, fatigue, fainting, chest discomfort, weakness, dizziness, and/or giddiness. The cardiac monitoring device can record predetermined physiologic parameters of the patient (e.g., ECG information) for a predetermined amount of time (e.g., 1-30 minutes before and 1-30 minutes after a reported symptom). As noted above, the cardiac monitoring device can be configured to monitor physiologic parameters of the patient other than cardiac related parameters. For example, the cardiac monitoring device can be configured to monitor, for example, cardio-vibrational signals (e.g., using accelerometers or microphones), pulmonary-vibrational signals, breath vibrations, sleep related parameters (e.g., snoring, sleep apnea), tissue fluids, among others.

In some examples, the devices described herein (e.g., FIGS. 11A-11D) can communicate with a remote server via an intermediary or gateway device 1180 such as that shown in FIG. 11D. For instance, devices such as shown in FIGS. 11A-D can be configured to include a network interface communications capability as described herein in reference to, for example, FIG. 3.

Additionally, the devices described herein (e.g., FIGS. 11A-11D) can be configured to include one or more accelerometers as described herein. For example, as noted above in the discussion of FIGS. 1A and 1B, one or more sensors such as accelerometers, vibrational sensors, and RF sensors can be integrated into various components of a wearable device or included as standalone sensors configured to measure various signals for a patient.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the scope of the appended claims. For example, it is to be understood that the present disclosure contemplates that, to the extent possible, one or more features of any embodiment can be combined with one or more features of any other embodiment.

Other examples are within the scope of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

Example Implementations

A medical device controller as described herein can include one or more database tables configured to store wear compliance information. For example, the database tables can include a wear compliance table and a flag table. In some examples, the wear compliance information and flag data can be combined into a single database table. In an example, the database table can store how long the device has been worn using multiple rows for separate wear time periods. The schema for creating such a database table can be as follows:

```
CREATE TABLE wear-compliance (
  wcompIdMain INTEGER PRIMARY KEY,
  wcompId INTEGER, //-- ID of current wear period
  wearTimeStart DATETIME, //-- Start of wear period
  wearTimeEnd DATETIME, //-- End of wear period
```

```
  wearTimeUpdate BOOLEAN, //-- if 1, midnight crossing event
occurred, and record is ended
  ECGnoiseFlagMask INTEGER, //-- If this flag is ON there is noise in
the ECG signal, and the current session is not reliable
  ECGdetectorFlagMask INTEGER //-- if this flag is ON, confirms that
wear compliance is based on ECG data
);
```

In some examples, a wear compliance process as described herein can use ECG signal detection and monitoring for determining compliance. For example, observing valid ECG data on at least one ECG channel can provide an indication of wear compliance. In various sample implementations, a processor of a medical device controller as described herein can be configured to implement such a feature as represented by the following pseudocode:

When the belt is connected and the detection system is activated, the compliance monitoring module activates compliance tracking.

Monitor ECG-channel-1 and ECG-channel-2
    ECGs are captured differentially via 4 ECG electrodes (e.g., predetermined bandwidth of 1 MHz-10 kHz, or 10 MHz-5 kHz) for some common mode noise rejection.
    Before digitization, ECG signals are passed into a bandpass filter (0.1 Hz-60 Hz).
    ECG signals are amplified in a dynamic amplifier.
    For example, amount of amplification is controlled (e.g., every 2, 5, seconds, 7 seconds, 10 seconds, 15 seconds, or other dynamic duration depending on rhythm). The amount of amplification is controlled to ensure that the ECG signal detection module (including arrhythmia detection module) and noise detection modules receive the ECG signal samples at the optimal levels.

The processor can be further configured to determine wear compliance based upon a valid ECG signal. For example, the processor can be configured to implement such a feature as represented in the following pseudocode:

Validate ECG signal
    Detect a predetermined QRS wave on at least one of the ECG channels for a predetermined duration. Process finds the QRS complex based on the dual criteria of the amplitude and duration of QRS complex. In an example, use Pan Tompkins to detect QRS. After a predetermined duration of time, called "WearTimePreOnPeriod" (e.g., 5 seconds of QRS signals or other pre-configured value, or dynamically changing value) initiate wear time ("wearTimeStart"),
Dynamic changes to WearTimePreOnPeriod duration: If the signal is noisy (as indicated by ECGnoiseFlagMask), then the predetermined duration of time is extended. For example, extended to around 10 seconds to allow for more ECG samples to be collected.
(Alternative step 1:) Dynamic changes to predetermined duration WearTimePreOnPeriod: If QRS samples are detected for a preset portion of the WearTimePreOnPeriod duration. For example, the preset portion may be set to 80%. This means that if during 80% of the WearTimePreOnPeriod the dual criteria is met, then compliance tracking is initiated (WearTimeStart).
Otherwise, the WearTimePreOnPeriod duration is extended by an additional period, for example, 3 seconds.

Above dynamic check is then repeated for the extended WearTimePreOnPeriod duration. The WearTimePreOnPeriod resets when the total duration reaches a predetermined maximum (e.g., 15 seconds).

When a predetermined duration of time, called "WearTimeGoesOffperiod" (e.g., 5 seconds or other pre-configured value, or dynamically changing value), passes, during which a threshold level of QRS signals are not detected, then compliance monitoring module indicates that compliance tracking is paused ("WearTimeEnd").

Example of dynamic changes to predetermined duration WearTimeGoesOffperiod: If QRS samples are not detected for a preset portion of the WearTimeGoesOffperiod duration. For example, the preset portion may be set to 80%. This means that if during 80% of the Wear TimeGoesOffperiod the dual criteria is not met, then compliance tracking is paused (WearTimeEnd).

Otherwise, the Wear TimeGoesOffperiod duration is extended by an additional period, for example, 3 seconds.

The above dynamic check is repeated for the extended WearTimeGoesOffperiod duration.

The WearTimeGoesOffperiod resets when the total duration reaches a predetermined maximum (e.g., 15 seconds). In this situation, it means that the ECG signal is still good, and patient compliance information indicates patient is wearing the device properly.

Checks if midnight crossing has occurred. If so, compliance tracking routine updates the records to split the one which is crossing midnight into two records.

For the prior 24 hour period, compliance module records how many hours and minutes cumulatively patient has worn the device. For example, in Fig. X, patient wore from 00:00 hours to 08:00 hours, and then from 10:00 hours to 23:00 hours. The overall cumulative duration for the 24-hour period is thus 22 hours.

When the belt is disconnected or system shuts down which means detection system is deactivated, compliance monitoring also pauses (wearTimeEnd).

Figure 12:
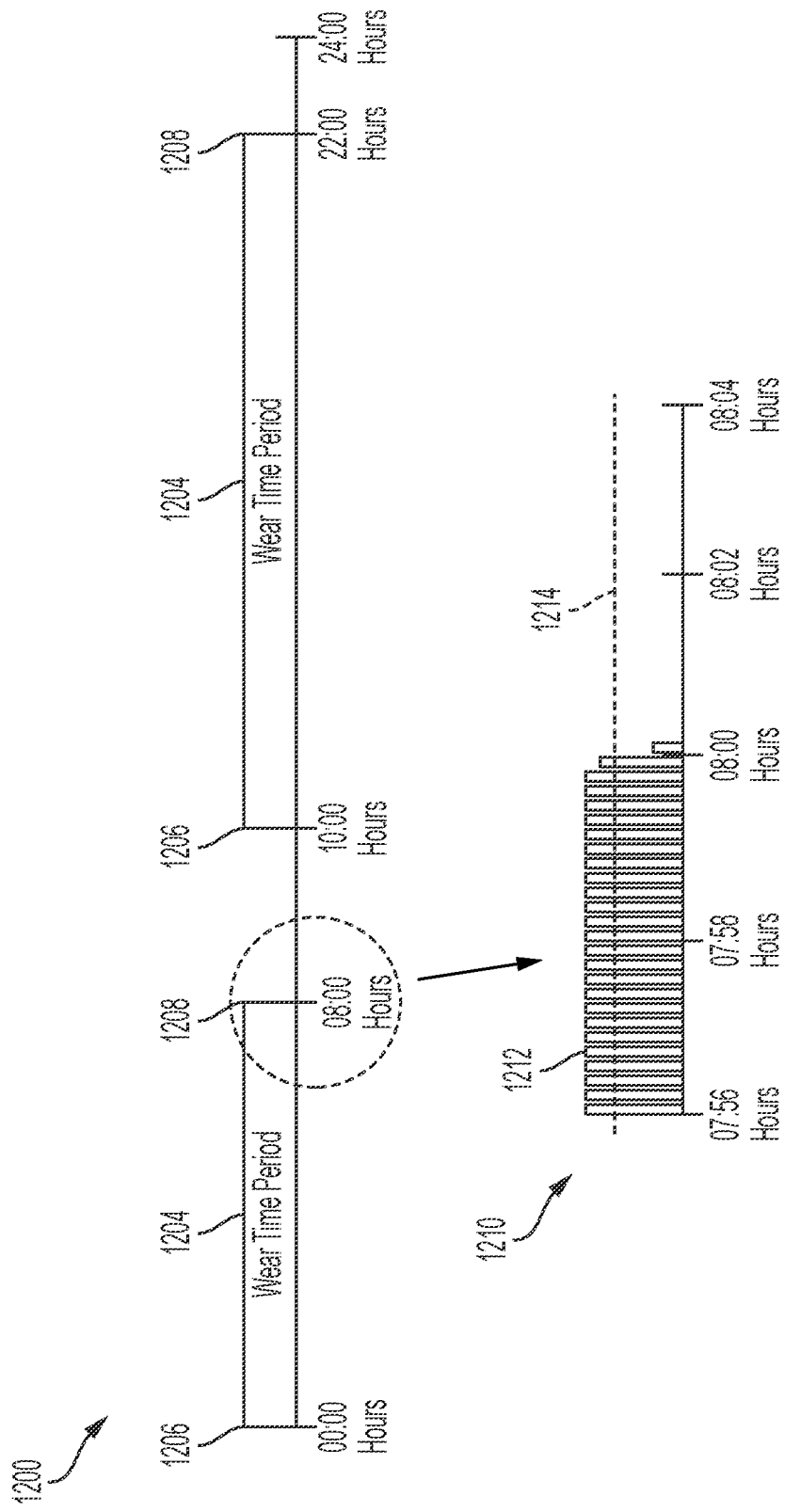
FIG. 12 illustrates a sample timing diagram depicting wear time periods for a patient and corresponding onset and offset events, in accordance with an example of the present disclosure.

FIG. 12 illustrates a sample timing diagram 1200 illustrating a visual representation of wear compliance information for a patient over a period of time. In this example, diagram 1200 includes a timeline that represents a 24 hour period, from 00:00 hours to 24:00 hours. During the time period, the timeline includes various information related to wear compliance for a patient such as wear time periods 1204, recorded onset events 1206, and recorded offset events 1208. Based upon the information shown in diagram 1200, a physician, patient, or other similar reviewer can quickly determine what portion of the time period the patient was wearing the medical device.

As further shown in FIG. 12, the diagram 1200 includes a sample detailed view 1210 of a recorded offset event 1208. As shown in the detailed view 1210, a series of measured R-waves 1212 are measured during the wear time period 1204. The magnitude of the R-waves 1212 stays above a minimum R-wave magnitude threshold 1214 until the timeline approaches 08:00 hours. As the timeline approaches 08:00 hours, the magnitude of the measured R-waves 1212 begins to drop and crosses threshold 1214 at 08:00 hours. As such, at 08:00 hours, the processor running the compliance monitoring process as described herein can record an offset event 1208 ending the wear time period 1204. The processor can then continue to monitor for an onset event 1206 that indicates that the patient is wearing the medical device once again.

In some examples, a medical device such as the wearable medical devices as described herein can be configured to inject or otherwise apply an electrical signal to a patient's body. By monitoring for and measuring this electrical signal, a processor can determine whether the patient is wearing the medical device and, as such, determine wear compliance. For example, a processor of a medical device controller can be configured to implement such a feature as represented in the following pseudocode:

Cause a low level AC signal (called wear-time signal) to be applied to the body, e.g., via a therapy electrode. Predetermined frequency, e.g., 800 Hz signal. Can be in a range of, e.g., 100 Hz to 1 MHz.

Detect the wear-time signal in hardware with a highpass filter and store the resulting samples in an accumulator. A WearTimeStart detection flag can be set when the output of the accumulator is compared to a predetermined threshold (wear-time signal accumulator threshold).

The output of the accumulator should stay above the predetermined threshold for a dynamic duration as described below.

After a predetermined duration of time, WearTimePreOnPeriod (e.g., 5 seconds of accumulator output staying above threshold or other pre-configured value, or dynamically changing value) initiate wear time (WearTimeStart).

Example 1 of dynamic changes to WearTimePreOnPeriod duration: If the signal is noisy (as indicated by ECGnoiseFlagMask), then the predetermined duration of time is extended. For example, extended to around 10 seconds to allow for more time to detect additional wear-time signal samples in order determine if wear-time signal accumulator threshold is met.

Example 2 of dynamic changes to predetermined duration WearTimePreOnPeriod: If wear-time signal samples are detected for a preset portion of the WearTimePreOnPeriod duration. For example, the preset portion may be set to 80%. This means that if during 80% of the WearTimePreOnPeriod the wear-time accumulator threshold is met, then compliance tracking is initiated (WearTimeStart). Otherwise, the WearTimePreOnPeriod duration is extended by an additional period, for example, 3 seconds. The above dynamic check is then repeated for the extended WearTimePreOnPeriod duration. The WearTimePreOnPeriod resets when the total duration reaches a predetermined maximum (e.g., 15 seconds).

When a predetermined duration of time, WearTimeGoesOffperiod (e.g., 5 seconds or other pre-configured value, or dynamically changing value), passes, during which the wear-time signal accumulator threshold is not met, then compliance monitoring module indicates that compliance tracking is paused (WearTimeEnd).

Example of dynamic changes to predetermined duration WearTimeGoesOffperiod: If wear-time signal accumulator threshold is not met for a preset portion of the WearTimeGoesOffperiod duration. For example, the preset portion may be set to 80%. This means that if during 80% of the WearTimeGoesOffperiod the wear-time signal accumulator threshold is not met, then compliance tracking is paused (WearTimeEnd). Otherwise, the WearTimeGoesOffperiod duration is extended by an additional period, for example, 3 seconds. The above dynamic check is repeated for the extended WearTimeGoesOffperiod duration. The WearTimeGoesOffperiod resets when the total duration reaches a predetermined maximum (e.g., 15 seconds). In this situation, it means that the wear-time signal accumulator threshold has been met, and patient compliance information indicates patient is wearing the device properly.

Compliance module checks if midnight crossing has occurred hours). If so, compliance tracking routine updates the records to split the one which is crossing midnight into two records.

For the prior 24 hour period, compliance module records how many hours and minutes cumulatively patient has worn the device.

When the belt is disconnected, or system shuts down which means detection system is deactivated, compliance monitoring also pauses (wearTimeEnd).

Figure 13:
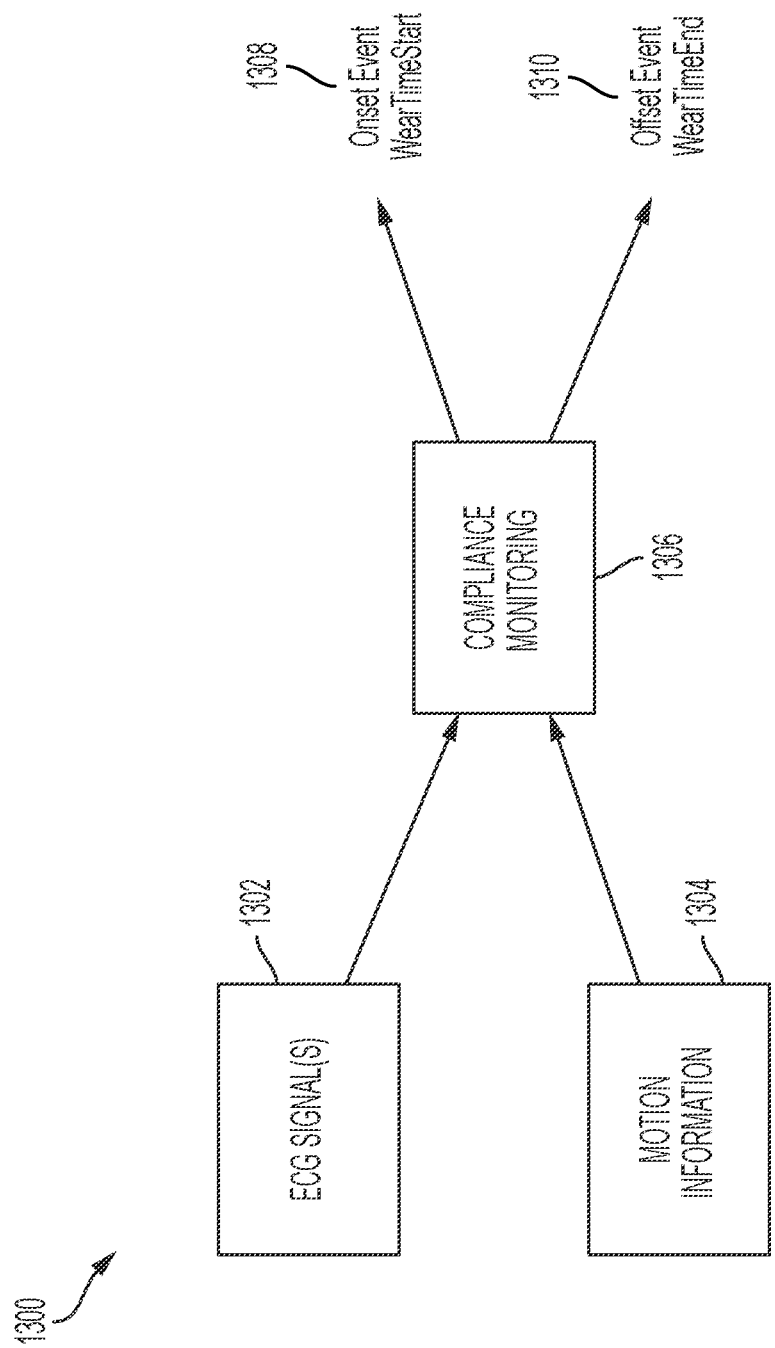
FIG. 13 illustrates a sample input/output diagram for a compliance monitoring process, in accordance with an example of the present disclosure.

As described herein, in certain implementations a compliance monitoring process can include both physiological signals such as ECG signals as well as motion information such as the output of one or more accelerometers as inputs. For example, as shown in FIG. 13, sample input/output diagram 1300 includes one or more ECG signals 1302 as well as motion information 1304 as inputs to the compliance monitoring process 1306. A processor can be configured to implement compliance monitoring process 1306 to process the inputs to produce one or more outputs. For example, the process 1306 can be configured to output an output 1308 that includes an indication of an identified onset event as well as a positive value for variable wearTimeStart as described herein. Similarly, the process can be configured to output an output 1310 that includes an indication of an identified offset event as well as a positive value for variable wearTimeEnd as described herein. In certain implementations, when a testing period is used to confirm whether an onset event or an offset event has occurred, the outputs 1308 and 1310 can also include an indication of when the onset event and/or offset event begins. In examples, the processor can be further configured to implement one or more additional features as represented in the following pseudocode:

If motion information (ACC signal) indicates that the patient is walking, running, climbing stairs, or otherwise moving.
  Confidence threshold for such motion is high (e.g., above 0.75, 0.8 or other preset value, or dynamically changing value)
  Then, WearTimeStart can be set.
  In optional implementation, the ECG signal detection module (see above detail) should also output flag agreeing that WearTimeStart can be set. When both ACC signal detection module and ECG signal detection module agree, WearTimeStart can be set.
If ACC signal does not indicate that patient is performing one of walking, running, climbing stairs, or otherwise moving
  For example, confidence threshold for motion (as determined above) is low
  Period of day is predetermined SleepPeriod=ON (e.g., configurable, default set between 10 PM and 6 AM)
  Check heart rate data for validation of whether patient is sleeping
  If ACC signal and heart rate data indicates patient is asleep, then WearTimeStart can be set.
    In an optional embodiment, the ECG signal detection module (see above detail) should also output flag agreeing that WearTimeStart can be set. When both ACC signal detection module, heart rate data, and ECG signal detection module agree, WearTimeStart can be set.
If ACC signal does not indicate patient is performing one of walking/running/climbing stairs, AND SleepPeriod is not ON
  The ECG signal detection module (see above detail) is used as described above to output flag indicating when WearTimeStart can be set.

In addition to the variables listed in relation to the database table above and described herein, other similar variables can be monitored and recorded in one or more database tables described herein. For example, variable "totalHoursOfUse" can be recorded and include data representing first and last wear date segments in the calculation. In examples, variable "averageDailyUse" can be recorded and can include wear date segments on days which segments sum above the minimum daily threshold for daily use. In examples, variable "totalDays" can be recorded and can include the total number of days the patient has worn the medical device. In examples, variable "totalPatientUsePercent" can be recorded and can include a percentage of time the device was worn for a requested date range. In examples, variable "firstWearDate" can be recorded and can include the first wear date. In examples, variable "lastWearDate" can be recorded and can include the last wear date. In examples, variable "calendarDate" can be recorded and can include a calendar date. In examples, variable "dailyCompliance" can be recorded and can include first and last wear date segments when the patient exceeded the minimum daily threshold. In examples, variable "totalSeconds" can be recorded and can include the combined wear duration of all segments within a given calendar date. In example, variable "compliancePercentage" can be recorded and can include a percent of wear time of the medical device for a single day by the patient. Variables as described herein are provided by way of example only for illustrative purposes and are not intended to limit the scope of the database tables as described herein.

The above wear compliance detection processes reference heart rate data. Heart rate for use with compliance monitoring can be determined using one or more detection methods or processes. For example, heart rate detection implementations can include, but are not limited to, one or more of the following:

Analysis of ECG time signal: Heart rate is assessed by measuring the duration between two ECG complexes.
Derivative Based Detector: To detect the complex, a derivative filter is being employed to accentuate the complex. The output of the filter is then being compared to a dynamic threshold to determine if ECG complex is detected.
QRS detector: To detect heart rate, a detector analyzes ECG signal slope to detect QRS complex presence. This is accomplished by applying a differential filter. An ECG signal from ADC is first bandpass filtered (2 Hz-20 Hz) to remove baseline wandering and high frequency noise. The output of this bandpass filter is then fed to the QRS detector, which will do slope analysis. The output of QRS detector will be a binary value that equals to one if it is detecting a QRS complex and zero otherwise. QRS rate is assessed by measuring the period between two successive peaks of an ECG signal and comparing the output with an adaptive threshold.

Axis Detector: To detect the complex, a complex match filter operation is performed to find similarity between captured ECG and incoming ECG. The idea behind axis detector is to perform waveform feature analysis. The analysis starts by capturing ECG waveform from both channels. The acquired waveform are being compared to incoming ECG via a complex match filter. When enough similarity between captured ECG and incoming ECG is present, a match is detected. The matched complexes per minute provide an indicated of heart rate.

Analysis of ECG spectrum: Heart rate can be measured by decomposing ECG signal into its spectrum. This method is suitable for ventricular tachycardia/fibrillation where ECG time signal analysis often had difficulty in assessing heart rate. An ECG signal to be analyzed is decimated from 200 Hz to 25 Hz. Spectrum analyzer can decompose this decimated ECG into its spectrum. Spectral analysis is accomplished by calculating energy distribution in the spectrum. Tachycardia or fibrillation will often result in a spectrum which tends to concentrate at a specific frequency corresponding to heart rate. In examples, spectral analysis can be performed once every second. For example, index to largest peak magnitude between 2 Hz and 6 Hz is determined, thus indicating the fundamental frequency. A percentage of power in the fundamental frequency s determined. If this power is over a predetermined threshold, then rate can be determined based on the fundamental frequency (e.g., inverse of frequency value).

What is claimed is:

1. A wearable defibrillator for providing patient wear compliance information, the wearable defibrillator comprising:
   an adhesive patch, configured to be adhesively applied to a skin of a patient, the adhesive patch having disposed thereon
      a plurality of electrodes that, when the adhesive patch is adhered to the skin, are configured to be continuously coupled externally to the patient for an extended period of time, the plurality of electrodes configured to monitor electrical activity on the skin of the patient and provide a therapeutic shock to the patient in response to detection of a cardiac arrhythmia based on the monitored electrical activity, and
      at least one motion sensor and associated circuitry configured to generate at least one motion signal based upon movement of the patient;
   a user interface configured to receive user input indicating that the patient has put on the wearable defibrillator; and
   at least one processor operably coupled to the plurality of electrodes and the at least one motion sensor and associated circuitry, the at least one processor configured to
      receive a control signal from the user interface indicating that the user input has been provided;
      after receiving the control signal from the user interface, receive at least one electrical signal based on the monitored electrical activity on the skin of the patient from the plurality of electrodes,
      record a wear onset event based on the control signal from the user interface, the at least one electrical signal and the at least one motion signal indicating that the patient is wearing the wearable defibrillator,
      record a wear offset event based on one or more of the at least one electrical signal or the at least one motion signal indicating that the patient is not wearing the wearable defibrillator, and
      output a graphical representation comprising information regarding the patient's wear compliance based on the recorded wear onset event and the recorded wear offset event.

2. The wearable defibrillator of claim 1, further comprising a display operably coupled to the at least one processor, and wherein the at least one processor is configured to provide, via the display, the graphical representation comprising the information regarding the patient's wear compliance.

3. The wearable defibrillator of claim 1, further comprising a network interface operably coupled to the at least one processor, and wherein the at least one processor is configured to transmit the information regarding the patient's wear compliance to a remote server.

4. The wearable defibrillator of claim 1, wherein to record the wear onset event comprises to:
   detect one or more ECG signals based on the at least one electrical signal;
   determine whether the one or more ECG signals satisfy one or more validity criteria; and
   if the one or more ECG signals satisfy at least one criterion of the one or more validity criteria, record the wear onset event.

5. The wearable defibrillator of claim 4, wherein the one or more validity criteria comprise at least one ECG parameter derived from the one or more ECG signals satisfying a validity threshold.

6. The wearable defibrillator of claim 5, wherein the at least one ECG parameter comprises one or more of:
   R-peak amplitude and satisfying the validity threshold comprises identifying at least five consecutive R-peak amplitudes that each exceed an amplitude threshold; or
   QRS complex width and satisfying the validity threshold comprises measuring at least five consecutive QRS complex widths that are each between 0.05 seconds and 0.15 seconds.

7. The wearable defibrillator of claim 1, wherein to record the wear onset event comprises to:
   detect a skin-sensor interface impedance level based on the at least one electrical signal at one or more of the plurality of electrodes;
   determine whether the impedance level is within an acceptable impedance range; and
   if the impedance level is within the acceptable impedance range, record the wear onset event; and
   wherein to record the wear offset event comprises to
      determine whether the impedance level is no longer within the acceptable impedance range, and
      record the wear offset event based on determining that the impedance level is no longer within the acceptable impedance range.

8. The wearable defibrillator of claim 7, wherein the acceptable impedance range comprises at least one of a range of 20 ohms to 250 ohms, a range of 250 ohms to 1 kiloohm, and a range of 1 kiloohm to 20 kiloohms.

9. The wearable defibrillator of claim 1, wherein to record the wear onset event comprises to:
   determine whether the at least one motion signal indicates movement of the patient and the wearable defibrillator;
   if the at least one motion signal indicates movement of the patient and the wearable defibrillator, record the wear onset event; and if the at least one motion signal indicates no movement of the patient and the wearable defibrillator, detect one or more ECG signals based on the at least one electrical signal and record the wear onset event based upon analysis of the one or more ECG signals.

10. The wearable defibrillator of claim 1, wherein to record the wear offset event comprises to:
   detect a change in the at least one electrical signal indicating an invalid ECG signal; and
   record the wear offset event based upon the invalid ECG signal.

11. The wearable defibrillator of claim 1, wherein to record the wear offset event comprises to:
   determine that one or more of the plurality of electrodes or the at least one motion sensor and associated circuitry have been disconnected from the wearable defibrillator; and
   record the wear offset event upon determining that the one or more of the plurality of electrodes or the at least one motion sensor and associated circuitry have been disconnected.

12. The wearable defibrillator of claim 1, wherein the graphical representation comprises one or more of:
   an indication of patient wear compliance relative to patient wear non-compliance;
   an indication of recorded changes in wear compliance for the patient;
   a timeline illustrating the recorded wear onset event and the recorded wear offset event, wherein the timeline further illustrates a total time the wearable defibrillator was worn by the patient and a total time the wearable defibrillator was not worn by the patient over a user-selectable period of time; or
   one or more user-selectable interface controls configured to provide access to recorded ECG information for one or more of the wear onset event, the wear offset event, or a period of time when the patient was wearing the wearable defibrillator.

13. The wearable defibrillator of claim 1, the at least one processor being further configured to output a notification of the patient's wear compliance, wherein to output the notification of the patient's wear compliance comprises to:
   compare the patient's wear compliance to one or more notification criteria; and
   if the patient's wear compliance satisfies at least one criterion of the one or more notification criteria, output the notification.

14. The wearable defibrillator of claim 13, wherein the one or more notification criteria comprise one or more of the patient failing to wear the wearable defibrillator for a certain percentage of a period of time or a recorded change in the patient's wear compliance that exceeds a compliance change threshold.

15. A wearable defibrillator for providing patient wear compliance information, the wearable defibrillator comprising:
   a plurality of electrodes configured to be continuously coupled externally to a patient for an extended period of time, the plurality of electrodes configured to monitor electrical activity on a skin of the patient and provide a therapeutic shock to the patient in response to detection of a cardiac arrhythmia based on the monitored electrical activity;
   at least one motion sensor and associated circuitry configured to generate at least one motion signal based upon movement of the patient;
   a user interface configured to receive user input indicating that the patient has put on the wearable defibrillator; and
   at least one processor operably coupled to the user interface, the plurality of electrodes and the at least one motion sensor and associated circuitry, the at least one processor configured to
      receive a control signal from the user interface indicating that the user input has been provided;
      after receiving the control signal from the user interface, receive at least one electrical signal based on the monitored electrical activity on the skin of the patient from the plurality of electrodes,
      determine a current time of day;
      record a wear onset event based on the control signal from the user interface, the at least one electrical signal, the at least one motion signal, and the current time of day, the wear onset event indicating that the patient is wearing the wearable defibrillator,
      record a wear offset event based on the at least one electrical signal, the at least one motion signal, and the current time of day, the wear offset event indicating that the patient is not wearing the wearable defibrillator, and
      output a graphical representation comprising information regarding the patient's wear compliance based on the recorded wear onset event and the recorded wear offset event.

16. The wearable defibrillator of claim 15, wherein to determine the current time of day comprises to determine whether the patient has historically been in an active state or an inactive state based upon the current time of day.

17. The wearable defibrillator of claim 16, the at least one processor being further configured to record at least one of the wear onset event or the wear offset event based upon the at least one electrical signal if the patient has historically been in the inactive state at the current time of day.

18. The wearable defibrillator of claim 16, the at least one processor being further configured to record at least one of the wear onset event or the wear offset event based upon the at least one electrical signal and the at least one motion signal if the patient has historically been in the active state at the current time of day.

19. The wearable defibrillator of claim 16, the at least one processor being further configured to determine whether the patient has historically been in the active state or the inactive state based upon the current time of day and historical patient activity information recorded by the wearable defibrillator.

20. The wearable defibrillator of claim 15, further comprising a display operably coupled to the at least one processor, and wherein the at least one processor is configured to provide, via the display, the graphical representation comprising the information regarding the patient's wear compliance.

* * * * *